US012630579B2

(12) United States Patent
Wang et al.

(10) Patent No.: US 12,630,579 B2
(45) Date of Patent: May 19, 2026

(54) PROTEOLYSIS TARGETING COMPOUND WITH TISSUE TARGETING CAPABILITY AND USE THEREOF

(71) Applicant: TAI BI DI PHARMACEUTICAL TECHNOLOGY (SHIJIAZHUANG) CO. LTD, Hebei (CN)

(72) Inventors: Jinxu Wang, Hebei (CN); Xiangdong Su, Hebei (CN); Mingjie Bai, Hebei (CN)

(73) Assignee: TAI BI DI PHARMACEUTICAL TECHNOLOGY (SHIJIAZHUANG) CO. LTD, Hebei (CN)

( * ) Notice: Subject to any disclaimer, the term of this patent is extended or adjusted under 35 U.S.C. 154(b) by 818 days.

(21) Appl. No.: 17/922,514

(22) PCT Filed: Apr. 29, 2021

(86) PCT No.: PCT/CN2021/090962

§ 371 (c)(1),
(2) Date: Oct. 31, 2022

(87) PCT Pub. No.: WO2021/219077

PCT Pub. Date: Nov. 4, 2021

(65) Prior Publication Data

US 2024/0270780 A1 Aug. 15, 2024

(30) Foreign Application Priority Data

Apr. 29, 2020 (CN) ......................... 202010354369.8

(51) Int. Cl.

| | |
|---|---|
| ***C07H 15/26*** | (2006.01) |
| ***A61K 31/7056*** | (2006.01) |
| ***A61K 31/7064*** | (2006.01) |
| ***A61P 35/00*** | (2006.01) |

(52) U.S. Cl.

CPC ......... *C07H 15/26* (2013.01); *A61K 31/7056* (2013.01); *A61K 31/7064* (2013.01); *A61P 35/00* (2018.01)

(58) Field of Classification Search

None

See application file for complete search history.

(56) References Cited

U.S. PATENT DOCUMENTS

| | | | | |
|---|---|---|---|---|
| 9,938,264 | B2 * | 4/2018 | Crews | ..................... A61P 43/00 |
| 2012/0157509 | A1 | 6/2012 | Hadwiger et al. | |
| 2015/0291562 | A1 | 10/2015 | Crew et al. | |
| 2016/0045607 | A1 | 2/2016 | Crew et al. | |
| 2019/0175612 | A1 | 6/2019 | Pillow et al. | |
| 2022/0089570 | A1 | 3/2022 | Crew et al. | |

FOREIGN PATENT DOCUMENTS

| | | | |
|---|---|---|---|
| CN | 103492568 | A | 1/2014 |
| CN | 106458993 | A | 2/2017 |
| CN | 108136044 | A | 6/2018 |
| CN | 109152843 | A | 1/2019 |
| WO | 2009073809 | A2 | 6/2009 |

OTHER PUBLICATIONS

International Search Report for Corresponding International Application No. PCT/CN2021/090962, 10 pages.

Written Opinion for Corresponding International Application No. PCT/CN2021/090962, 10 pages.

* cited by examiner

*Primary Examiner* — Traviss C McIntosh, III

(74) *Attorney, Agent, or Firm* — DINSMORE & SHOHL LLP

(57) ABSTRACT

The present invention is based on the discovery of a proteolysis targeting compound having tissue targeting capability and use thereof, relating to medicinal products, and to such a compound or a pharmaceutically acceptable salt thereof, a stereoisomer, a solvate, or a polymorph. The compound is a proteolysis targeting chimera (PROTAC) with specific tissue targeting ability. The compound structure comprises three parts, i.e., A-BD-CON, wherein the part A is a PROTAC, one end of the structure thereof is a target protein ‘binding ligand, and the other end is a ubiquitin ligase ligand; and the part CON is a ligand of an asialoglycoprotein receptor (ASGPR), enabling the specific tissue targeting function. The compound enriches in liver tissue and is able to target cells in the tissue. The invention achieves improved druggability of the PROTAC with higher solubility and cellular membrane permeability, therefore produces enhanced pharmaceutical effect on the specific target tissue.

11 Claims, 6 Drawing Sheets

Integration Results

Signal 1: DAD1 B, Sig=254,4 Ref=off

| # | R.T. | Type | Height | Height% | Width | Area | Area % |
|---|---|---|---|---|---|---|---|
| 1 | 0.946 | MM | 3.355 | 0.225 | 0.121 | 24.287 | 0.415 |
| 2 | 1.668 | MM | 27.324 | 1.836 | 0.069 | 113.711 | 1.942 |
| 3 | 2.134 | MF | 1441.100 | 96.855 | 0.065 | 5584.934 | 95.401 |
| 4 | 2.423 | FM | 10.647 | 0.716 | 0.140 | 89.456 | 1.528 |
| 5 | 2.965 | MM | 5.471 | 0.368 | 0.127 | 41.763 | 0.713 |

Signal 2: MSD1 TIC, MS File

| # | R.T. | Type | Height | Height% | Width | Area | Area % |
|---|---|---|---|---|---|---|---|
| 1 | 2.158 | MM | 89812.414 | 100.000 | 0.084 | 450906.594 | 100.000 |

PROTEOLYSIS TARGETING COMPOUND WITH TISSUE TARGETING CAPABILITY AND USE THEREOF

CROSS-REFERENCE TO RELATED APPLICATIONS

This application is the U.S. National Stage of PCT/CN2021/090962 filed on Apr. 29, 2021, which claims priority to Chinese Patent Application 202010354369.8 filed on Apr. 29, 2020, the entire content of both are incorporated herein by reference in their entirety.

FIELD OF THE INVENTION

The present invention relates to the field of medicinal products and in particular to a compound or a pharmaceutically acceptable salt, stereoisomer, solvate or polymorph thereof. The compound is a proteolysis targeting chimera (PROTAC) having with the specific tissue targeting ability. The structure of the compound comprises three parts, i.e., A-BD-CON, wherein the part A is a PROTAC, one end of the structure thereof is a target protein ‘binding ligand, and the other end is a ubiquitin ligase ligand; and the part CON is a ligand of an asialoglycoprotein receptor (ASGPR), having a function of enabling the specific tissue targeting function of the PROTAC. The invented compound further achieves the functions of enriching in liver tissues and is able to targeting cells in the tissue. The invention achieves improved druggability on the basis of the PROTAC having a high medicine making difficulty, and with improves the higher solubility of the PROTAC, and cellular membrane permeability, therefore produces enhanced and the pharmaceutical effect on a the specific target tissue, thus generally improving the medicine making properties.

BACKGROUND OF THE INVENTION

Cancer is a disease with high morbidity and mortality worldwide, posing a serious threat to human health and has become one of the important social problems faced by countries around the world. Liver cancer is the fourth most common tumor in China, with an annual increase of about 460,000 cases and the second highest mortality tumor in China (mortality rate of 26/100,000). In the world, there are more than 840,000 new liver cancer cases every year, and China accounts for about 50% of the world’s new liver cancer cases every year. Lacking effective treatment for liver cancer, the five-year survival rate of the disease is only 10%. Effective ways of prevention and control of liver cancer are in great need.

Hepatitis is another major liver disease, and with hepatitis B as the major subtype in China and other east Asian countries. At present, there are about 90 million hepatitis B virus carriers in China. According to the World Health Organization, only 8% of hepatitis B patients in the world have been under antiviral therapy, and about 10% in China. Ubiquitin-mediated proteolysis is among the most important down regulations of proteins in cells. Ubiquitin-mediated proteolysis pathway can degrade 80%~90% of ubiquitinated proteins in cells, and is involved in regulating cell cycle, proliferation, apoptosis, metastasis, gene expression and signal transduction, almost all life activities. This process occurs under the synergistic action of ubiquitin activating enzyme E1, ubiquitin conjugating enzyme E2 and ubiquitin ligase E3. After ubiquitination, the substrate protein is degraded in the proteasome. Since ubiquitin ligase E3 has specific recognition ability to the substrate protein, ubiquitin mediated proteolysis is specific. PROTACs are essentially heterobifunctional small molecule compounds structurally comprised of three parts, i.e. an ubiquitin ligase E3 ligand and a target protein binding ligand linked by a linker. PROTACs pull the target protein closer to the E3 in the cell, forming target protein-PROTACs-E3 enzyme. The target protein is tagged with ubiquitinated protein through the E3 ubiquitin ligase, which starts the powerful ubiquitinated hydrolysis process in the cell, and specifically degrades the target protein via the ubiquitin proteasome pathway to achieve the goal of treating diseases.

CN108601764A disclosed a series of VHL ligand structures for use in PROTAC as E3 ubiquitin ligase ligands.

Being different from “occupancy driven” mode of the traditional drug (that is, it needs to occupy the active site of the target protein continuously to block its function), PROTAC only needs to provide binding activity to trigger binding of the target protein to E3 ligase and thus cause degradation when it contacts with the target protein, which is called “event driven”. Long time and high intensity binding to the target protein is not required. Therefore, PROTAC can target traditionally undruggable targets, such as proteins with smooth surface that lack small molecule binding regions. Many targets that cannot be targeted with small molecules or antibodies can be targeted with PROTAC technology. PROTAC molecules can induce ubiquitination and degradation of target proteins only by binding to the surface of target proteins for a short time. This process is not limited by the traditional balanced occupancy, and is more similar to a catalytic behavior, which can be reused.

PROTAC has the following advantages in theory: the dosage is small, a catalytic level is enough, and the safety dose range is wide; drug resistance caused by target protein mutation/overexpression is overcome; and it is affinity independent and has high selectivity; and can clearance of protein accumulation.

Despite of the advantages mentioned above, PROTACs have the limitation in druggability. PROTAC molecular weight is generally above 700, breaking the drug-like rules in traditional small molecule pharmaceutical chemistry. They violate small molecule drug-like rules either in terms of molecular weight or complexity, so there inevitably exist many challenges in druggability, such as water solubility, permeability, PK/PD, etc. Off-target toxicity is also of common concern. PROTAC involves in an event driven catalytic reaction. Whether it affects on the expression of target proteins in normal tissues is unclear.

The asialoglycoprotein receptor (ASGPR) is an endocytosis receptor specifically expressed in hepatocytes, and can specifically recognize and bind non-reducing D-galactose (β-D-galactose, Gal) or N-acetylgalactosamine (GalNAc) that are terminal glycosyls of N-linked asialoglycoprotein, especially trimeric and quadruplex glycoproteins. In recent years, breakthroughs have been made in the liver targeted delivery of nucleic acid drugs using GalNAc, a high affinity ligand of ASGPR, as a targeting molecule. For example, by connecting the conjugated part containing terminal galactose or its derivatives to nucleic acid, the nucleic acid molecule can bind ASGPR and thus target liver cells. For example, see WO2009/073809, WO2011/104169 and WO2012/083046. However, applications and researches on other aspects of ASGPR ligands have not been reported yet.

SUMMARY OF THE INVENTION

In order to overcome the above-mentioned defects of PROTAC compounds in the prior art, the present invention provides inventively a combination of the ligand of the asialoglycoprotein receptor (ASGPR) with PROTAC compounds. The inventors find that using a specially designed linker surprisingly improves the solubility of the compound, the cellular permeability and biological effect on the liver tissue, and achieves the compound enriching effect in liver tissue and targeting to cells. The compounds can be decomposed into PROTAC and ASGPR ligands through cell endocytosis and lysosomal functions. The ASGPR receptor is recycled back to the cell surface. PROTAC can degrade the target protein. The present invention achieves the improvement of the transmembrane transport of PROTAC, lead to better efficacy in liver tissue, and generally improved druggability.

The present invention provides a compound or a pharmaceutically acceptable salt, stereoisomer, solvate or polymorph thereof. The compound is a proteolysis targeting chimera having improved solubility, tissue targeting ability and better druggability.

The structure of the compound comprises three parts: A-BD-CON, wherein the part A is a proteolysis targeting chimera (PROTAC), one end of which is a target protein binding ligand and the other end is a ubiquitin ligase ligand; and the part CON is a ligand of an asialoglycoprotein receptor (ASGPR), which has the comprehensive function of improving solubility, enabling targeting of PROTAC to specific tissues and cells and improving the medicinal product properties.

The present invention is realized through the following aspects:

In a first aspect, the present invention provides a compound of following formula or a pharmaceutically acceptable salt, stereoisomer, solvate or polymorph thereof, the compound consisting of following three parts:

A-BD-CON wherein CON is a ligand of asialoglycoprotein receptor (ASGPR), and

A has a formula of LGP-Y—Z-LK-LGE, wherein:

LGP is a target protein binding ligand,

LGE is an E3 ubiquitin ligase ligand;

Y and Z are independently selected from the group consisting of a covalent bond, $CH_2$, C1-C4 alkyl substituted methylene, NH, C1-C4 alkyl substituted nitrogen atom, O or S; and Z is selected from the group consisting of a covalent bond, $CH_2$ and C1-C4 alkyl substituted methylene when Y is selected from the group consisting of O, S, NH or C1-C4 alkyl substituted nitrogen atom; or Y is selected from the groups consisting of a covalent bond, $CH_2$ and C1-C4 alkyl substituted methylene when Z is selected from the group consisting of O, S, NH or C1-C4 alkyl substituted nitrogen atom;

LK is connected with LGP through Y—Z at one end thereof and is connected with LGE through covalent bond at the other end thereof, and LK is selected from following structural units:

a.

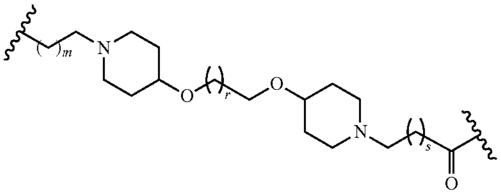

-continued

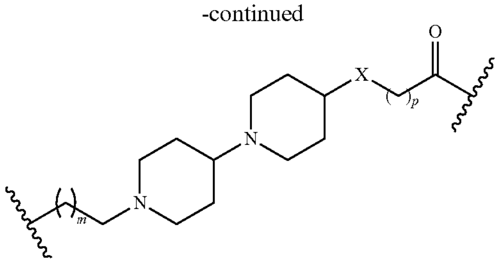

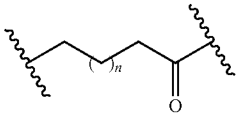

b.

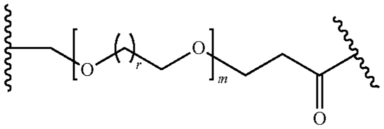

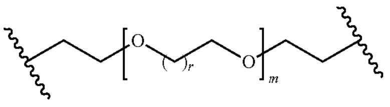

c.

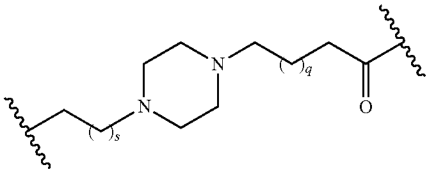

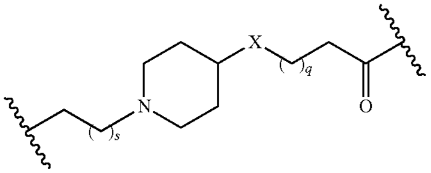

d.

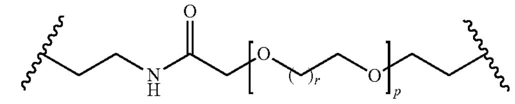

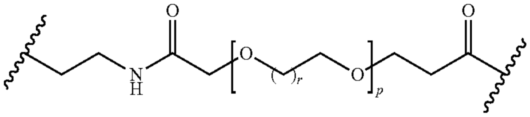

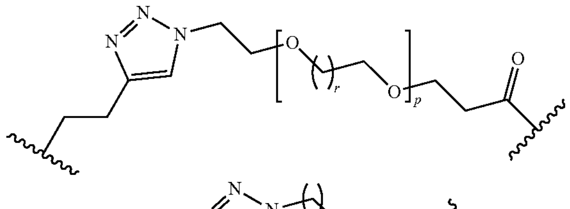

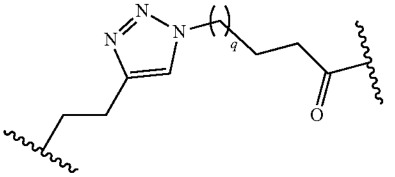

wherein m is an integer of 0-5; n is an integer of 0-20; p is an integer of 0-4; q is an integer of 0-20; r is an integer of 1-3; and s is an integer of 1-5; and X is selected from the groups consisting of $CH_2$, O, S and $NR^1$, wherein $R^1$ is selected from the groups consisting of H, C1-6 alkyl, C1-6 haloalkyl, or C1-6 alkoxy substituted C1-6 alkyl;

BD is a linker of A and CON and has formula of Q-LN, wherein Q is capable of being degraded and broken under acidic conditions by hydrolase in endosome or lysosomal in cells to release A; and Q is a structure selected from the group consisting of hydrazone, urea, oxime, disulfide, thioether, amide, ester (carboxylic acid ester, phosphate ester, pyrophosphate ester, carbonate ester, sulfate ester, sulfonic acid ester, amino sulfonic acid ester, methylene sulfonic acid ester, or carbamate), and

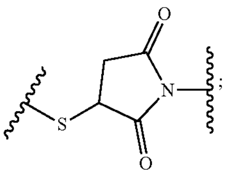 [SMILES: *SC1CC(=O)N(*)C1=O]

and LN is a linker of Q and CON and is selected from a carbon chain of 3-20 carbon atoms, and any $CH_2$ in the carbon chain is optionally substituted by O, NH, or C(O).

In a second aspect, LGE in the compound described in the first aspect is a ligand of ubiquitinated E3 enzyme, preferably a ligand of Von Hippel-Lindau tumor suppressor (pVHL), and more preferably a structure of following formula,

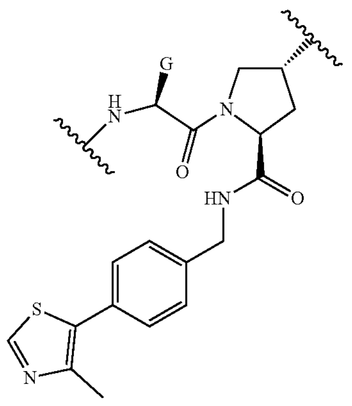

with one end being connected to LK and the other end being connected to Q, wherein LK and Q are the same as defined in claim 1; and wherein G is selected from the group consisting of C1-C10 alkyl, C3-C10 cycloalkyl, and 3-10 membered heterocyclic alkyl containing 1-3 heteroatoms selected from O, N and S, preferably is isopropyl, tertiary butyl, cyclohexyl or tetrahydropyran; and more preferably is tertiary butyl.

In a third aspect, the compound described in the first and second aspects is represented by the following formula:

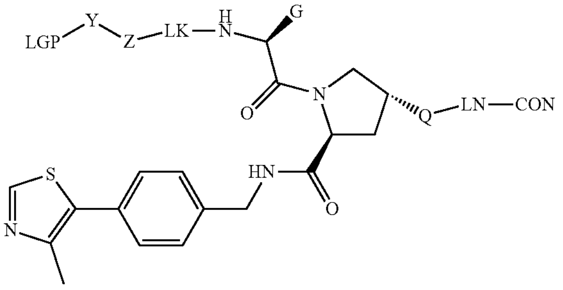

wherein Q is selected from the following structural units:

a.

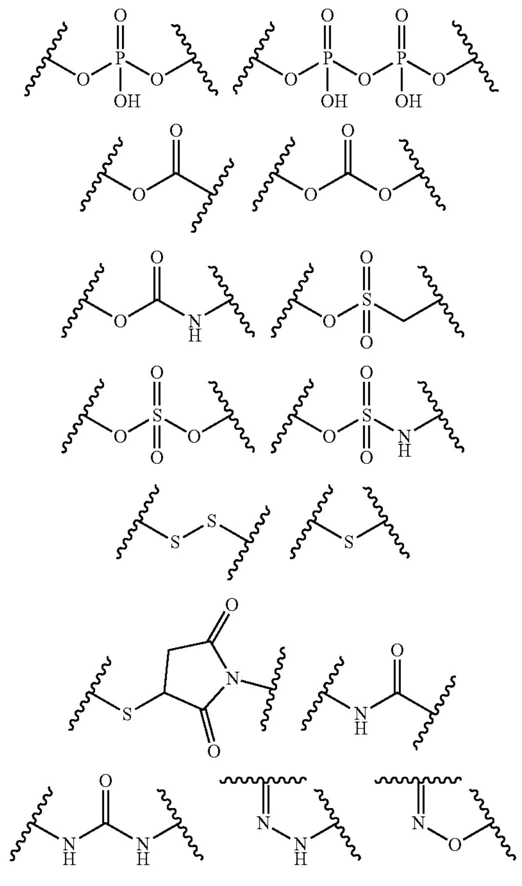

wherein LN is selected from the following structural units:

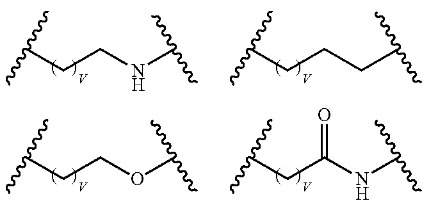

-continued

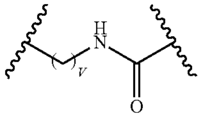

wherein V is an integer of 3-15, and preferably is an integer of 5-12, G in the formula is selected from the group consisting of C1-C10 alkyl, C3-C10 cycloalkyl, and 3-10 membered heterocyclic alkyl containing 1-3 heteroatoms selected from O, N and S, preferably is isopropyl, tertiary butyl, cyclohexyl or tetrahydropyran; and more preferably is tertiary butyl, Y and Z are the same as defined in the first aspect, and LK is independently selected from the same structural units as the LK in the first aspect.

In a fourth aspect, CON in the compounds described in the first to third aspects has a structure of following formula:

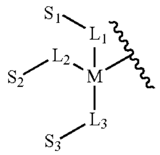

wherein S1-S3 are independently selected from the following structural units of: galactose, galactosamine, glucose, glucosamine, mannose, mannosamine and lactose acid, in the form of D-configuration or L-configuration;

wherein S1-S3 are respectively connected to L1-L3 through alpha glycosidic bond or beta glycosidic bond;

wherein L1-L3 are independently selected from the following structures of: chemical bond, aliphatic carbon chains of C3-C15, and aliphatic carbon chains of C3-C15 interrupted by one or more groups selected from O, S, NH or carbonyl at any position therein;

wherein M is selected from C, N, O, S and P(═O) and connected with LN via a covalent bond; and wherein S1-L1, S2-L2, or S3-L3 is optionally absent independently.

In a fifth aspect, CON in the compound described in the first to fourth aspects is selected from the following structures:

CON-1 i.

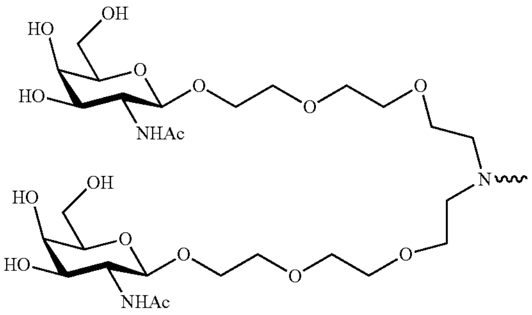

CON-2

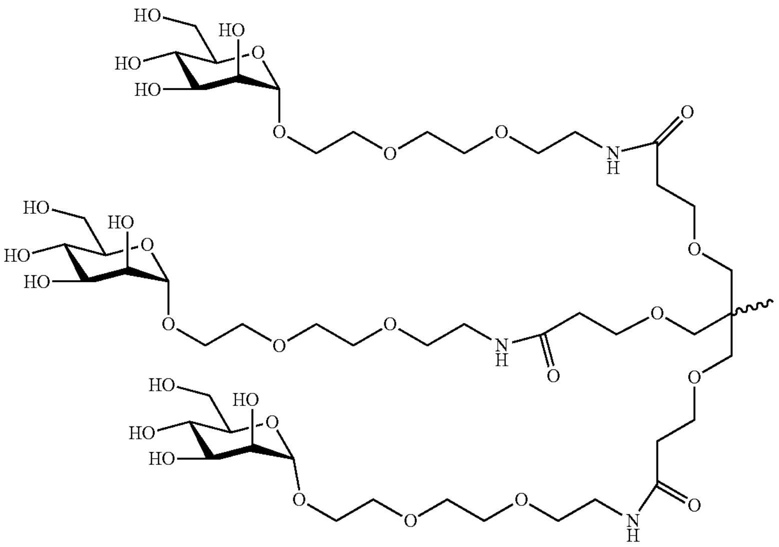

-continued
CON-3
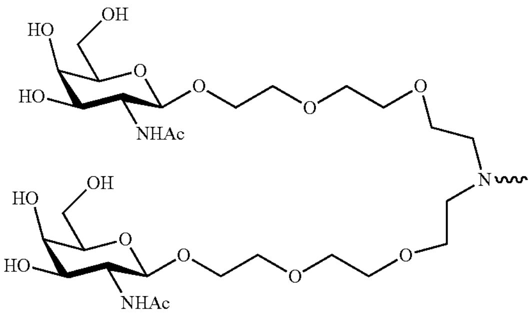
CON-4
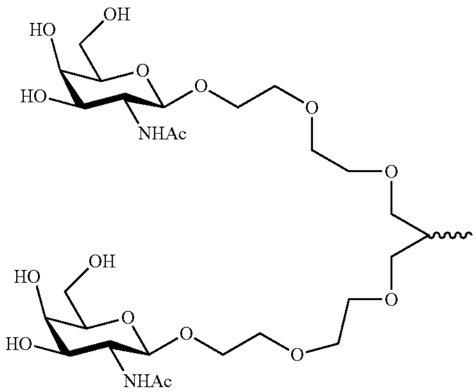
CON-5
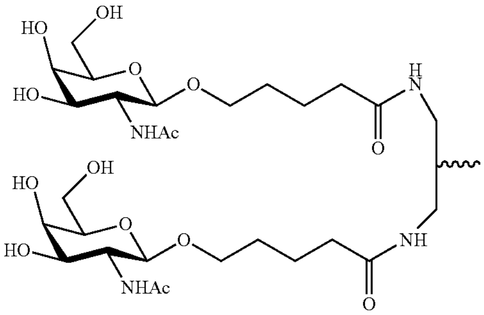
CON-6
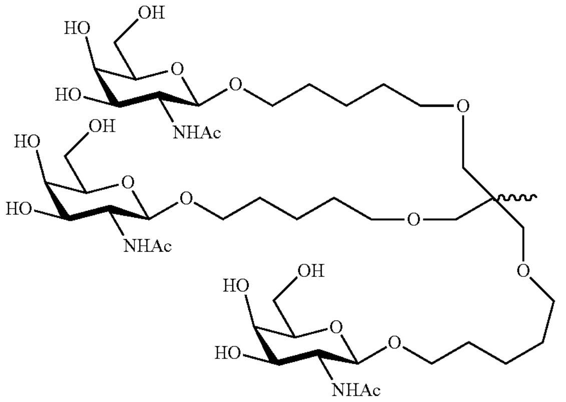
CON-7
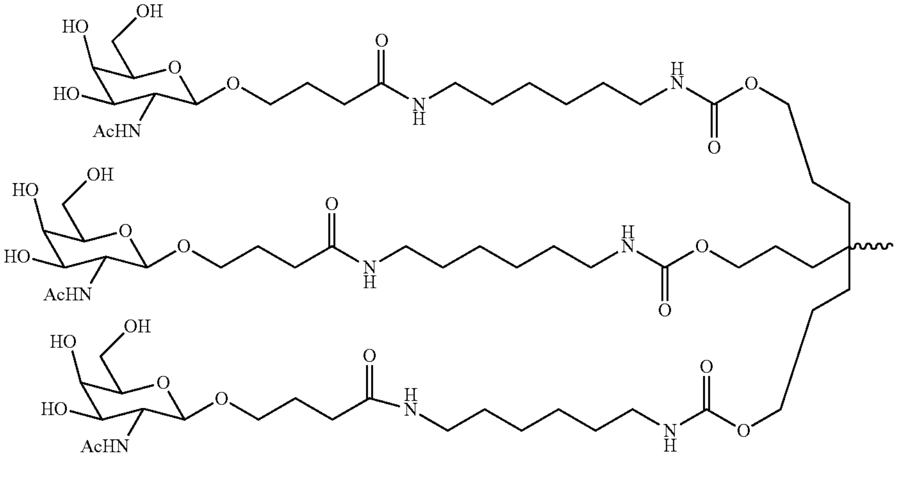

-continued
CON-8
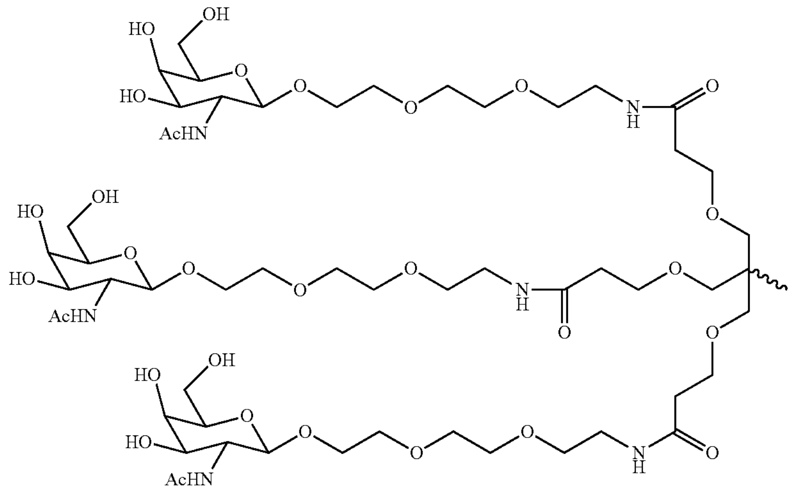
CON-9
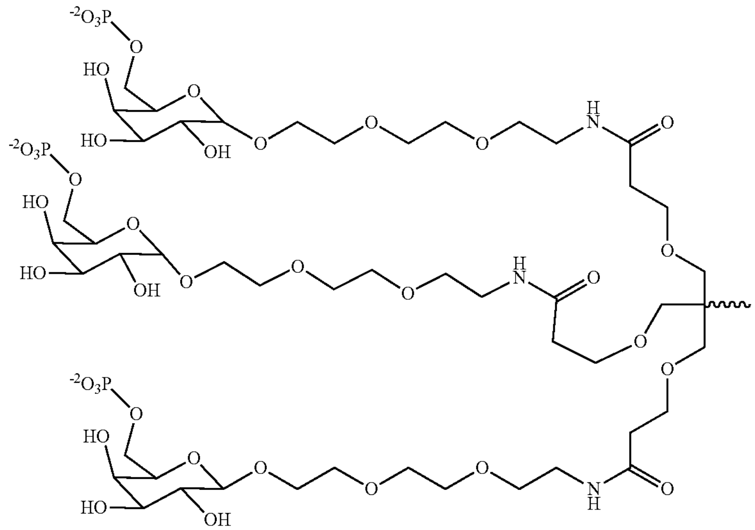
CON-10
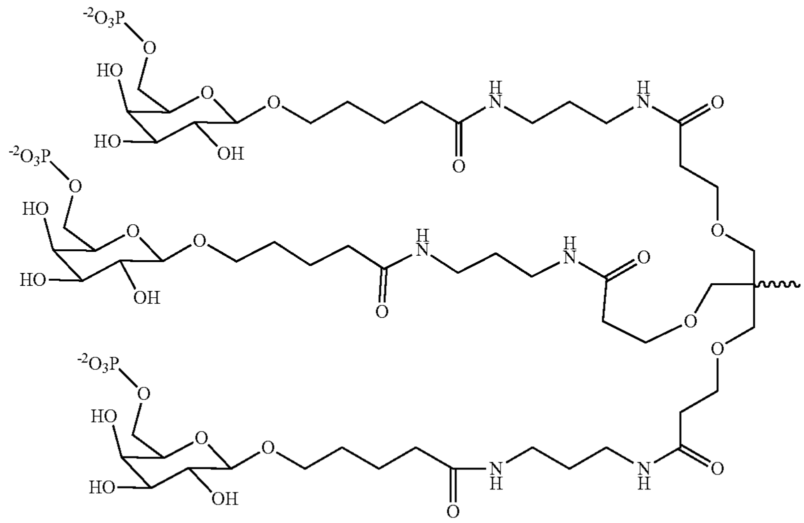

-continued
CON-11
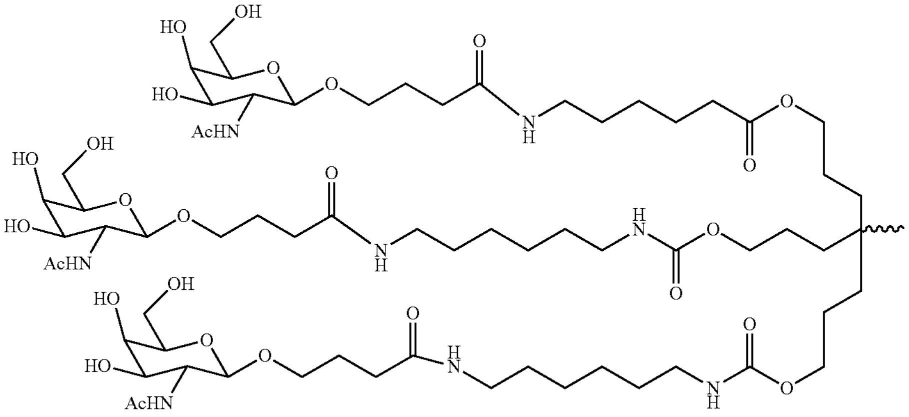
CON-12
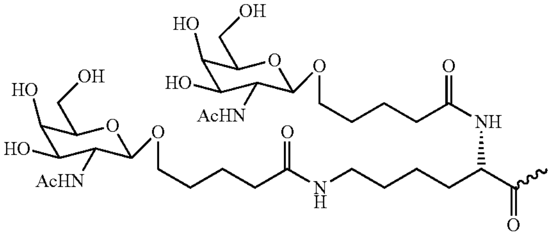
CON-13
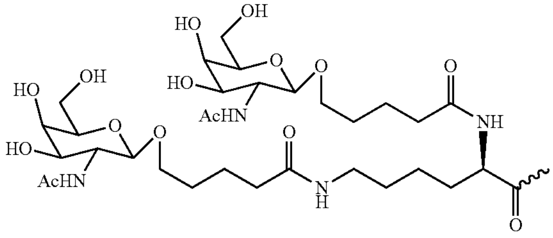
CON-14
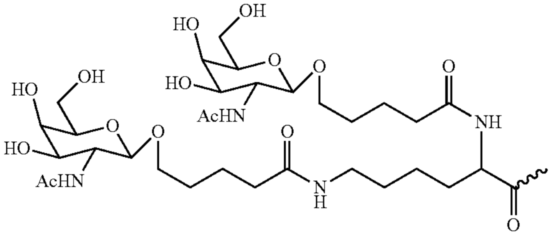
CON-15
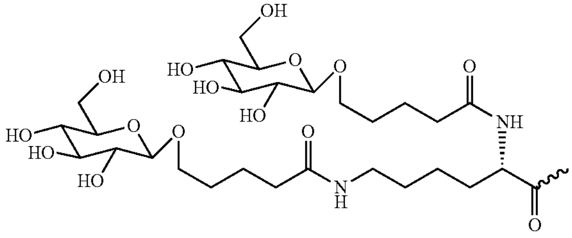
CON-16
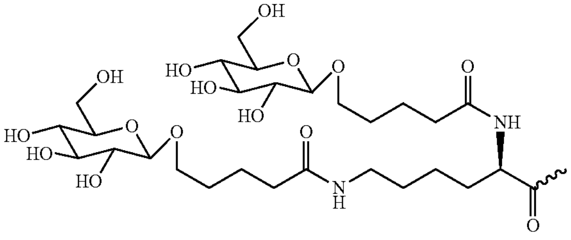
CON-17
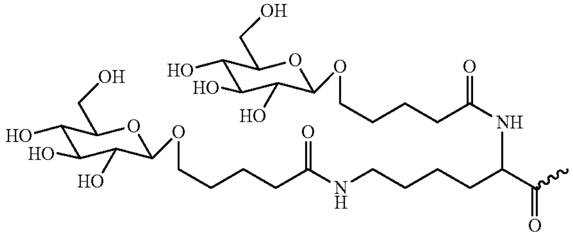
CON-18
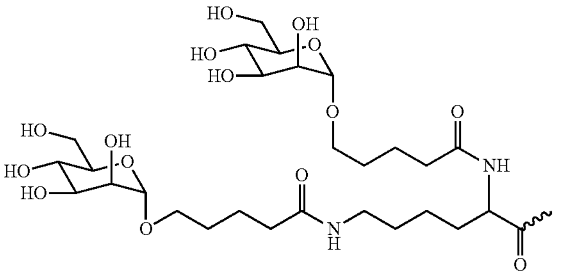
CON-19
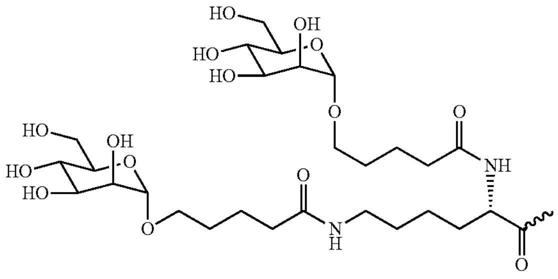

-continued
CON-20
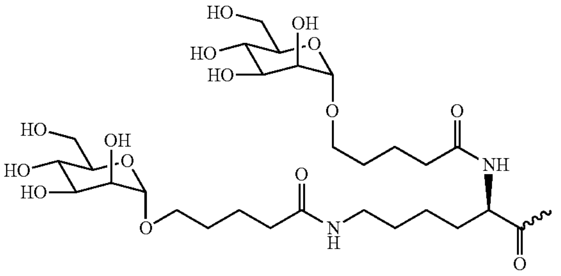
CON-21
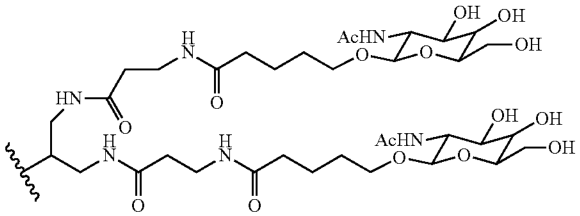
CON-22
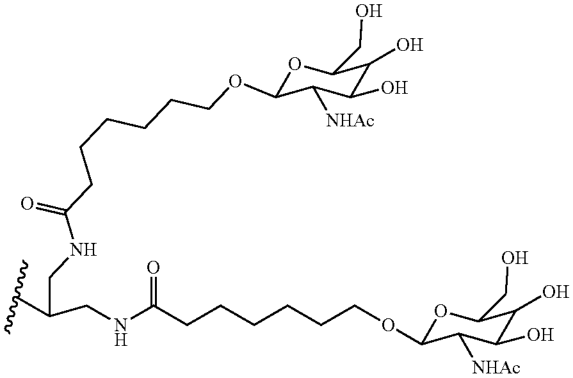
CON-23
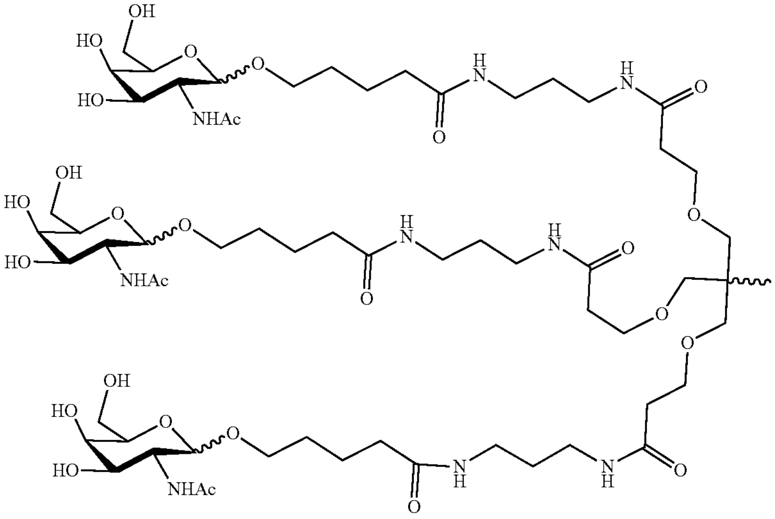

-continued
CON-24
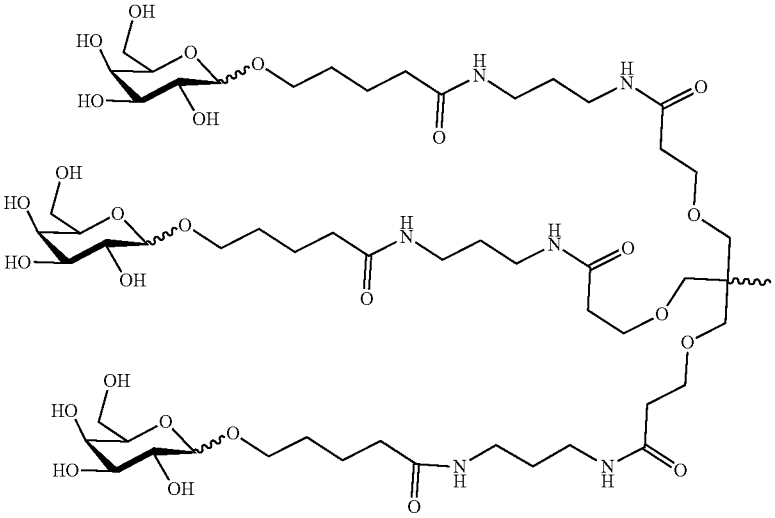
CON-25
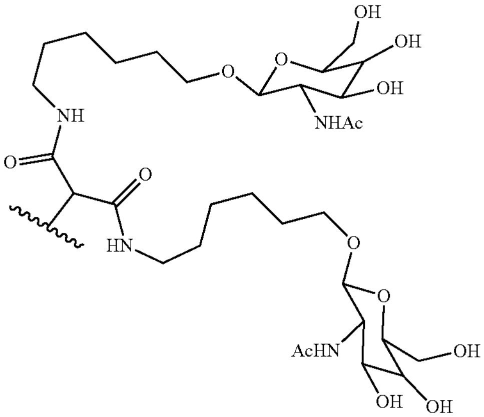
CON-26
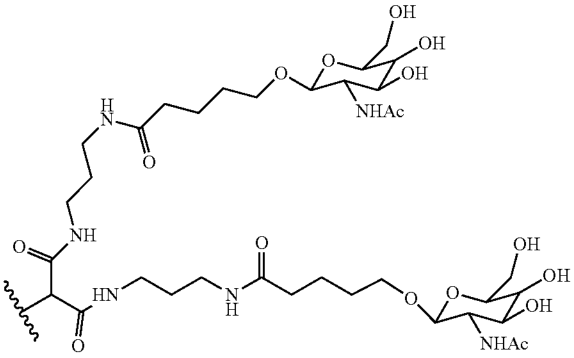
CON-27
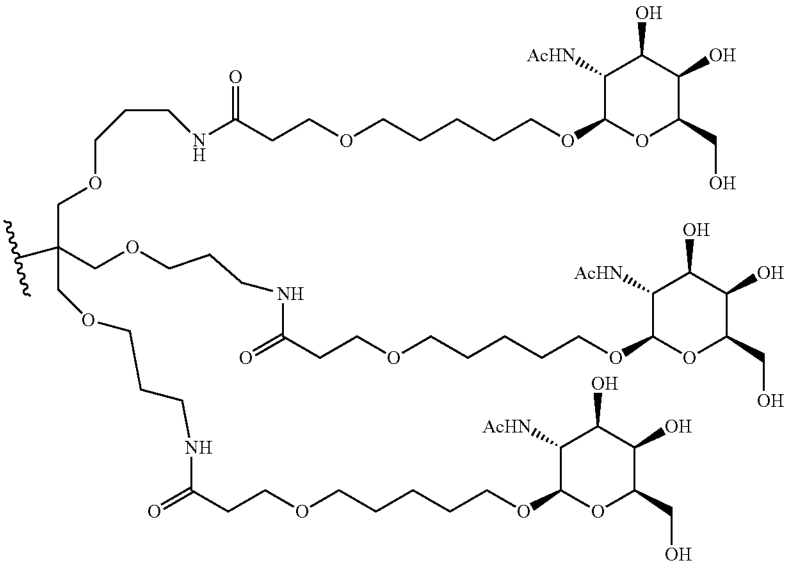

-continued
CON-28
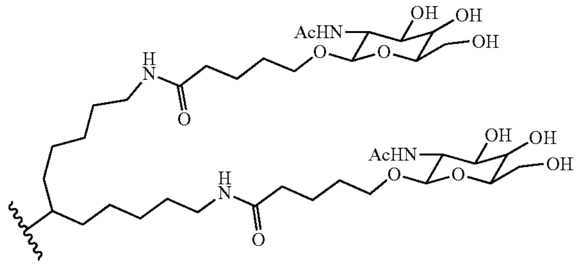
In a sixth aspect, LGP in the compound described in the first to third aspects is selected from the following structural units:
LGP-1
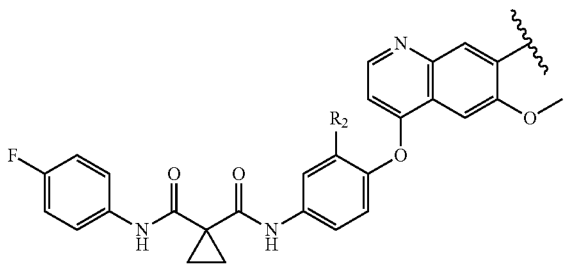
LGP-2
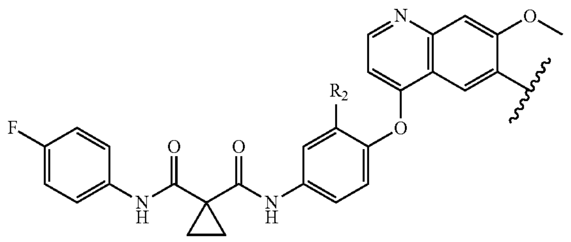
LGP-3
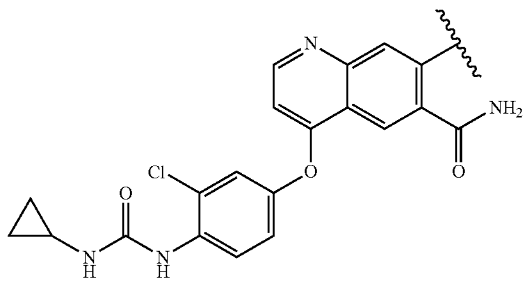
LGP-4
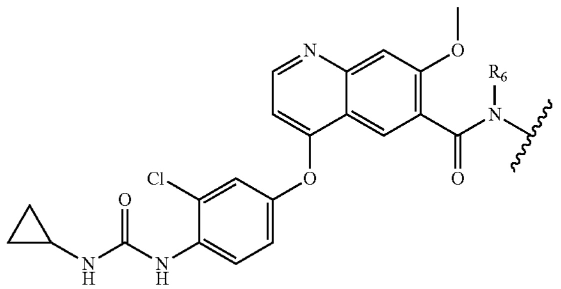
-continued
LGP-5
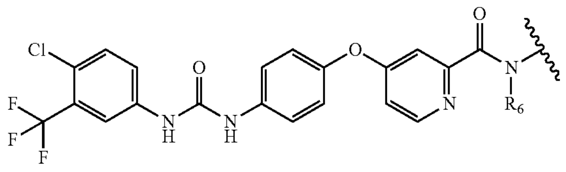
LGP-6
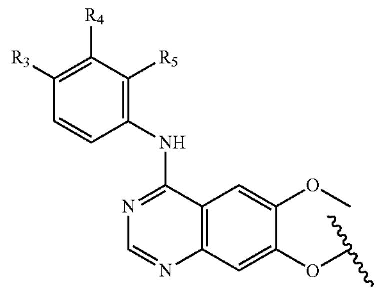
LGP-7
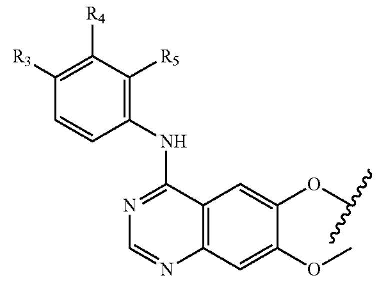
LGP-8
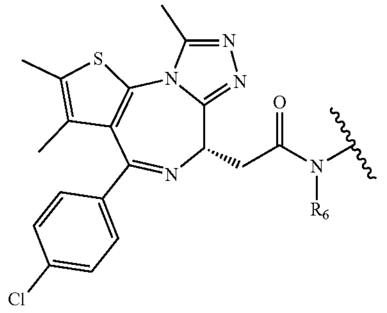

-continued

LGP-9

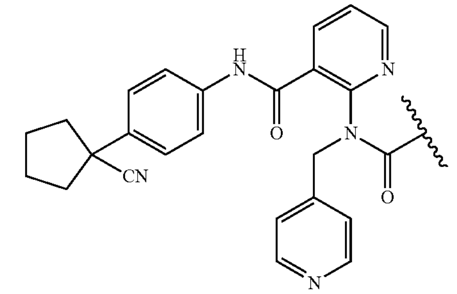

LGP-10

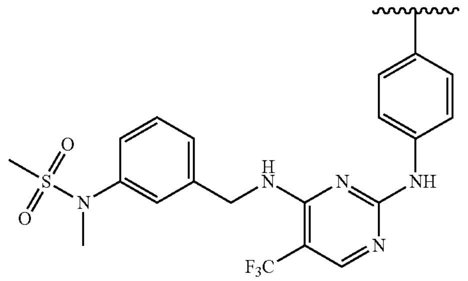

LGP-11

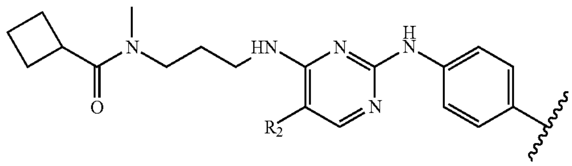

LGP-12

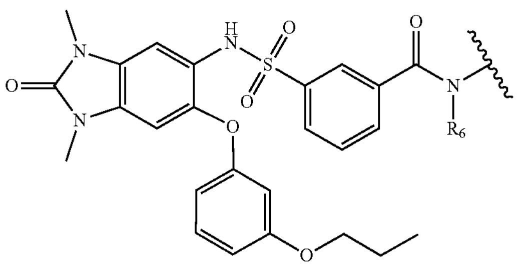

LGP-13

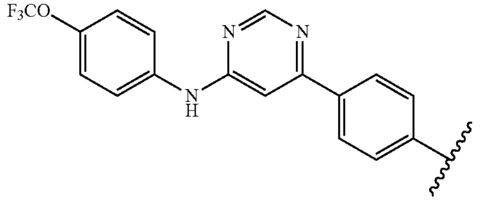

LGP-14

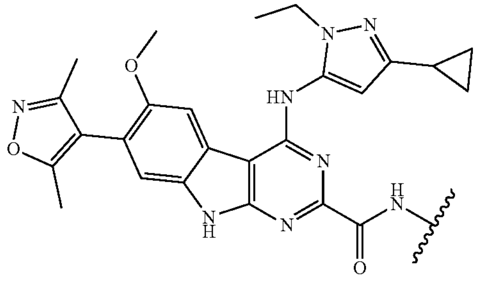

-continued

LGP-15

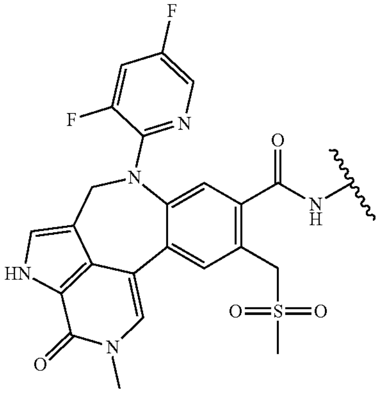

wherein R2-R5 are independently selected from the group consisting of H, F, Cl, Br, C1-4 alkyl, and C1-4 alkoxy; R6 is selected from the group consisting of H, C1-4 alkyl and C1-4 alkoxy.

In a seventh aspect, LGP in the compounds of any one of the above aspects is a ligand of cancer associated targets, microbial associated targets, immune diseases associated targets, neurodegenerative diseases associated targets or metabolic diseases associated targets.

In an eighth aspect, a binding target of LGP in the compounds of any one of the above aspects is selected from the group consisting of kinases, transcription factors, epigenetic reading frames, microtubule-associated proteins, microbial-associated proteins, and so on.

In a ninth aspect, a binding target of LGP in the compounds of any one of the above aspects is selected from the group consisting of EGFR, VEGFR, FGFR, PDGFR, Raf, Braf, RET, FLT, c-Kit, MET, ACVR, ALK, AKT, AhR, AURKA, AR, RAR, ER, BCL, BCR-ABL, BET, BMPR, BLK, BTK, BRD, CDK, CK, CHEK1, CTNNB1, DDR, DHODH, RAS, EED, ESR1, CRABP, CRBN, HER2, HER3, HMGCR, Htt, GNA11, GNA1, GNAS, NQO, TROP, eIF4E, ERK, ERG, ETV, ERRα, EZH2, FAK, IDH1/2, IGF1R, IRAK4, JAK, MEK, MELK, LTK, FKBP, MDM2, HDAC, MER, MCL, MTOR, PAR, PBRM, PCAF, PDE, PD-1, PD-L1, PTK, PARP, PDXK, PLK, PKB, MAPK, PI3K, Pirin, RIPK, Rpn13, PRC, P38, TGFβ, AFP, NTRK, NHE, CEA, SOAT1, SNCA, SYK, RNF43, DLK1, gp96, SGK, SMAD, SMO, SFB, SHP, SIK, SRC, STAT3, TBK, TYK3, TRIM, NS3, IRAK4, PCAF, GCN5, Sirt2, Tau, TUB, Weel, ZAK or their combined targets.

In a tenth aspect, LGP in the compounds of any one of the above aspects is selected from the group consisting of Hsp90 inhibitors, kinase inhibitors, phosphatase inhibitors, MDM2 inhibitors, compounds targeting proteins containing human BET bromodomain, HDAC inhibitors, human lysine methyltransferase inhibitors, compounds targeting RAF receptors, compounds targeting FKBP, angiogenesis inhibitors, immunosuppressive compounds, compounds targeting aryl hydrocarbon receptors, compounds targeting androgen receptors, compounds targeting estrogen receptors, compounds targeting thyroid hormone receptors, compounds targeting HIV protease, compounds targeting HIV integrase, compounds targeting HCV protease, and compounds targeting acyl protein thioesterase 1 and/or 2.

In an eleventh aspect, LGP in the compounds of any one of the above aspects is selected from the group consisting of: sorafenib, lenvatinib, regorafenib, cabozantinib, apatinib, refametinib, carboplatin, cisplatin, oxaliplatin, everolimus, pemetrexed disodium, erlotinib, dasatinib, imatinib, sunitinib, osimertinib, ibrutinib, alecinix, crizotinib, entrectinib, afatinib, axtintib, ceritinib, larotrectinib, brigatinib, neratinib, trametinib, lapatinib, neratinib, fluorouracil, 5-FU, etoposide, gemcitabine, decitabine, capecitabine, doxorubicin, epirubicin, vincristine, temozolomide, vincristine, ifosfamide, mitoxantrone, gefitinib, bortezomib, paclitaxel, docetaxel, pegylated interferon α-2a, interferon α-2a, pegylated interferon α-2b, interferon α-2b, azacitidine, cytarabine, cyclocytidine, irinotecan, topotecan, vidarabine, idoxuridine (IDU), trifluridine, bromovinyldeoxyuridine, magnesium glycyrrhizinate, glycyrrhizic acid, glutathione, polyene phosphatidyl choline, ademetionine, ursodeoxycholic acid, and ulinastatin.

In a twelfth aspect, the compound is selected from the following structures:

WG-1
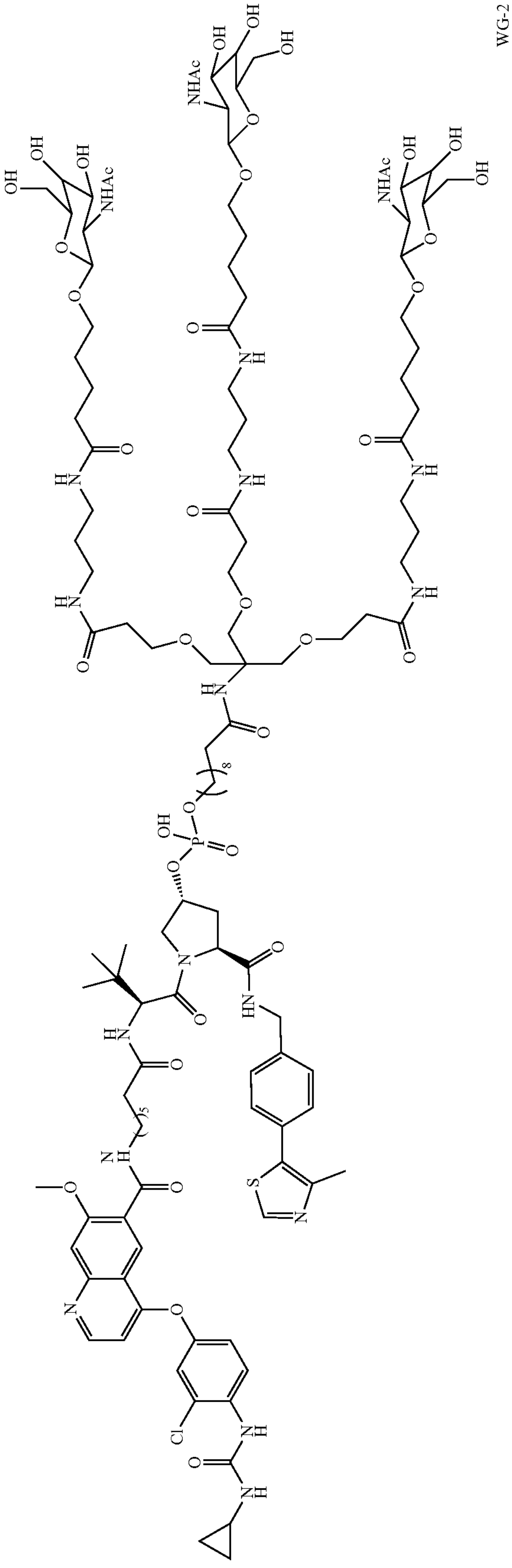
WG-2
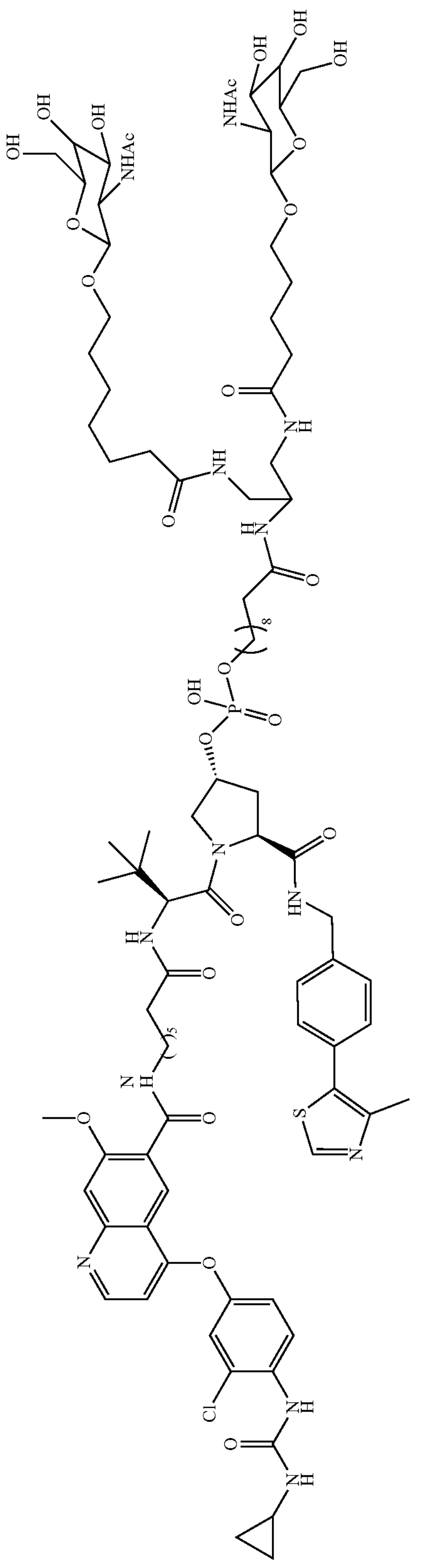

-continued
WG-3
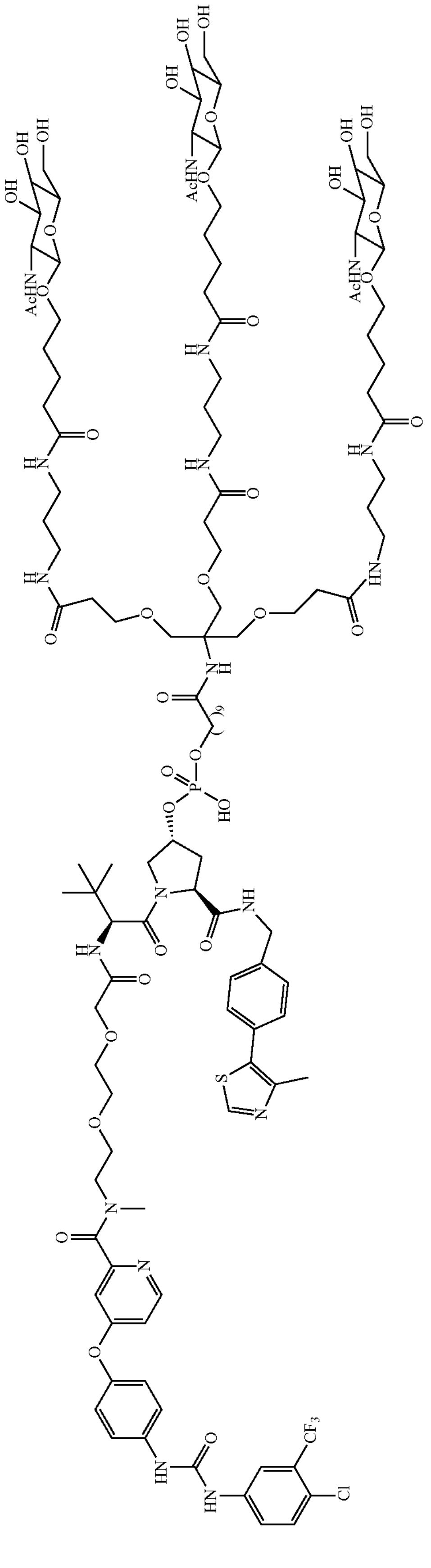

-continued
WG-4
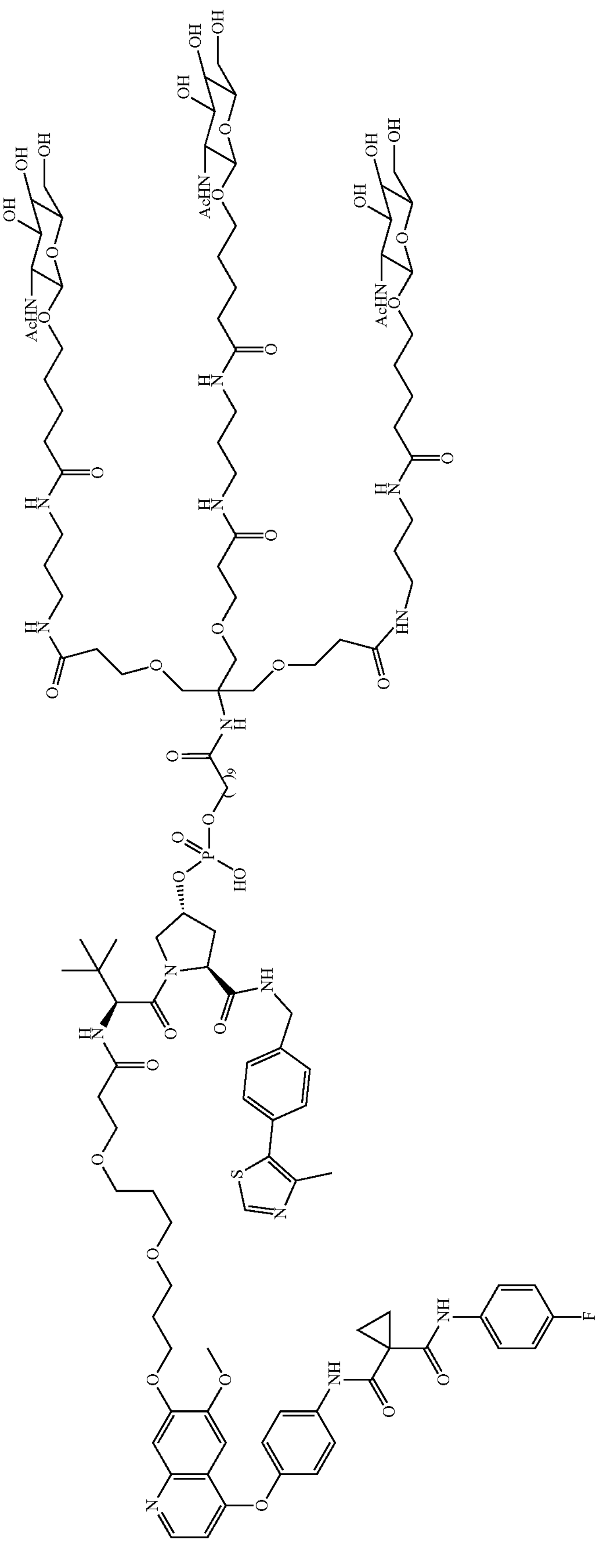

-continued
WG-5
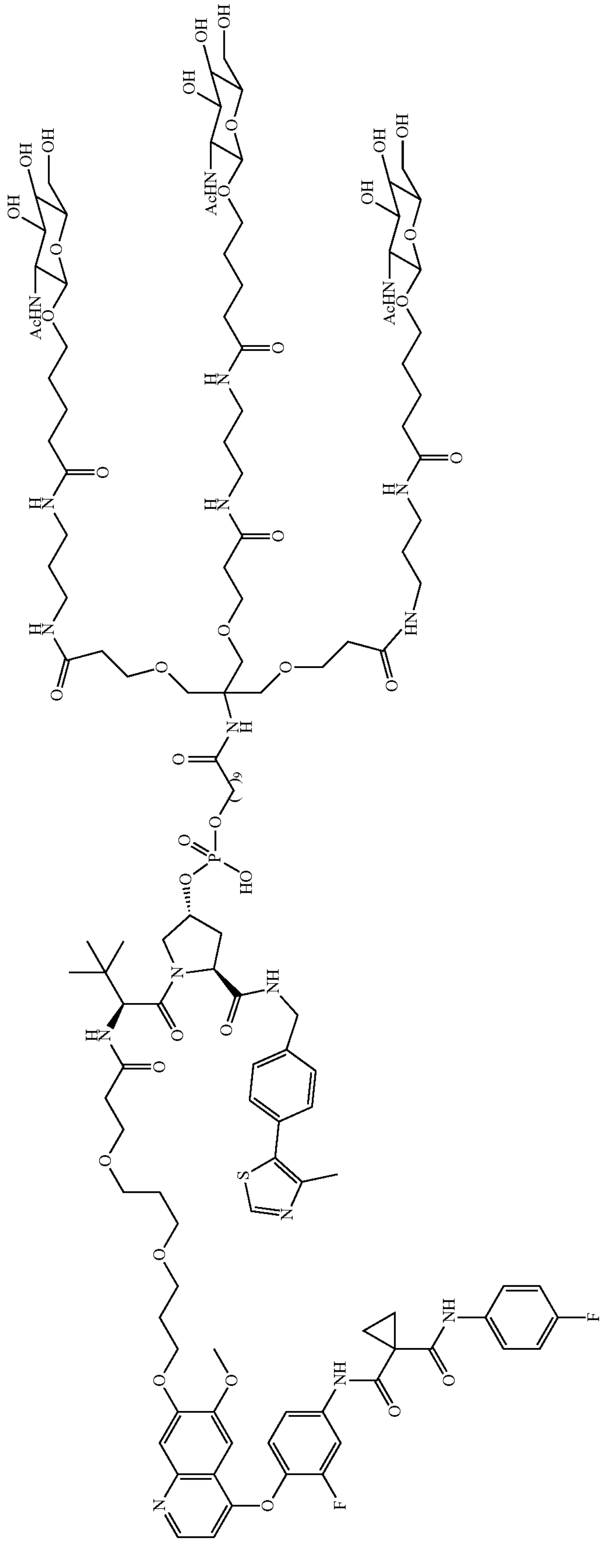

-continued
WG-6
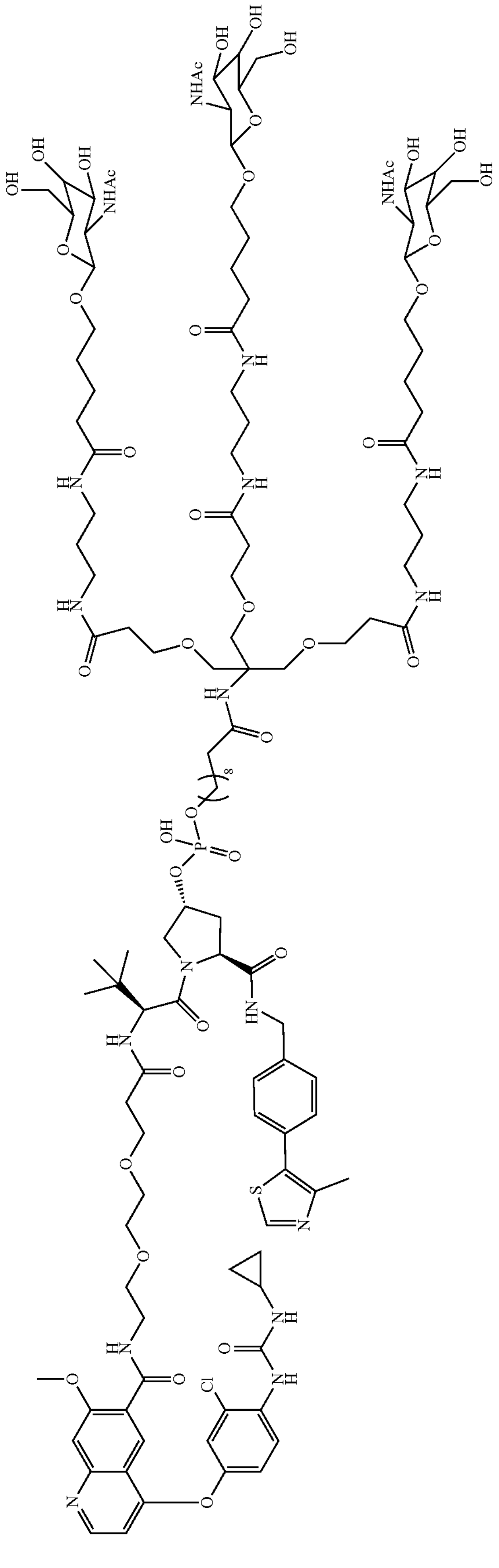
WG-7
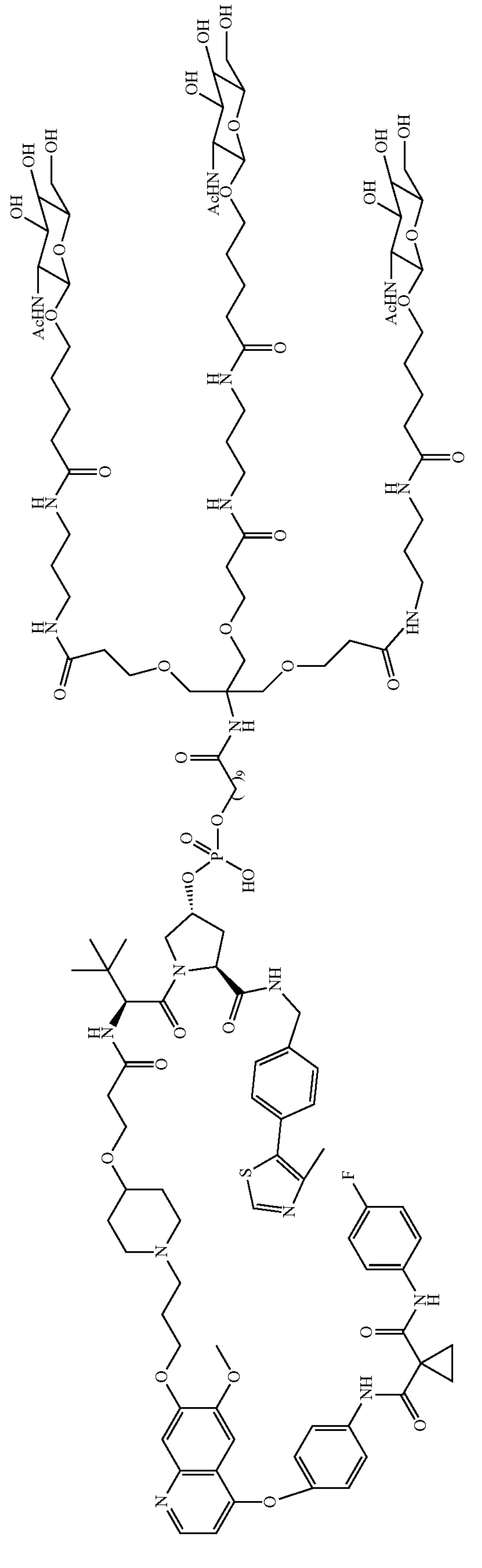

-continued
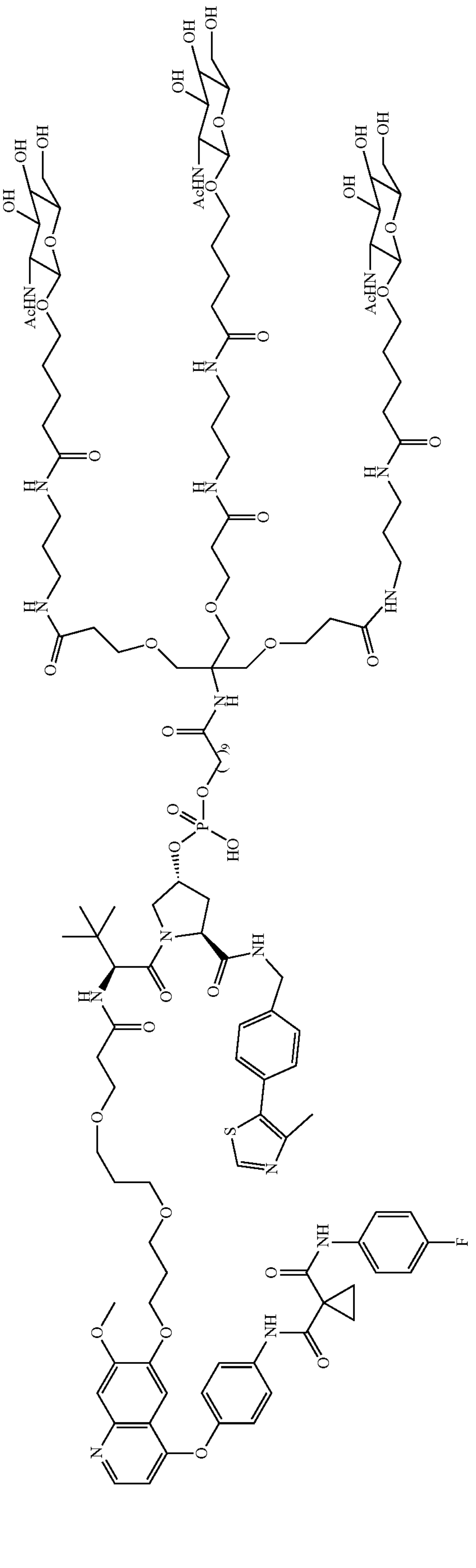
WG-8
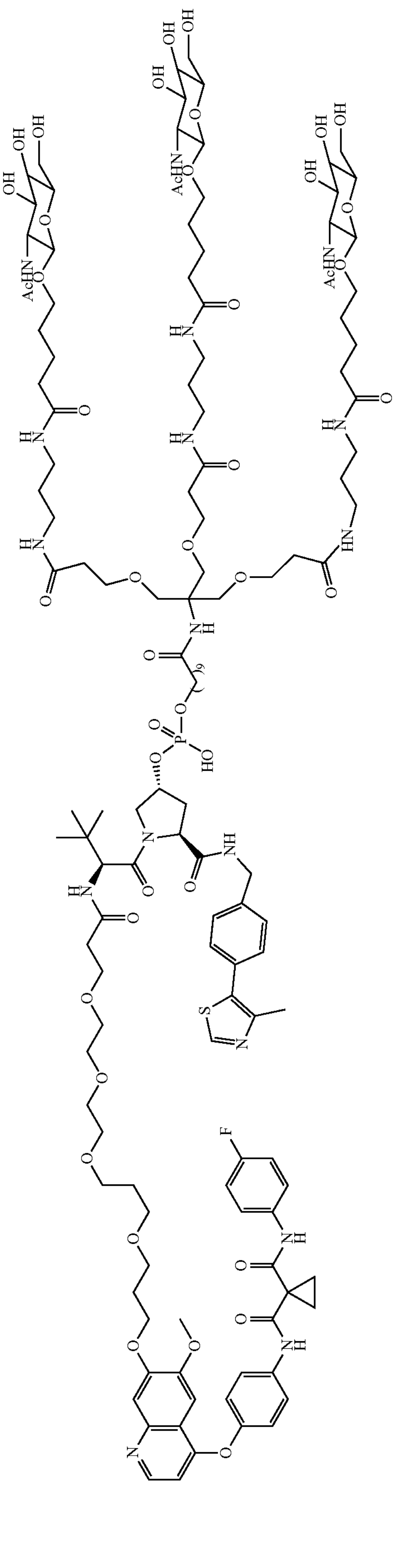
WG-9

-continued
WG-10
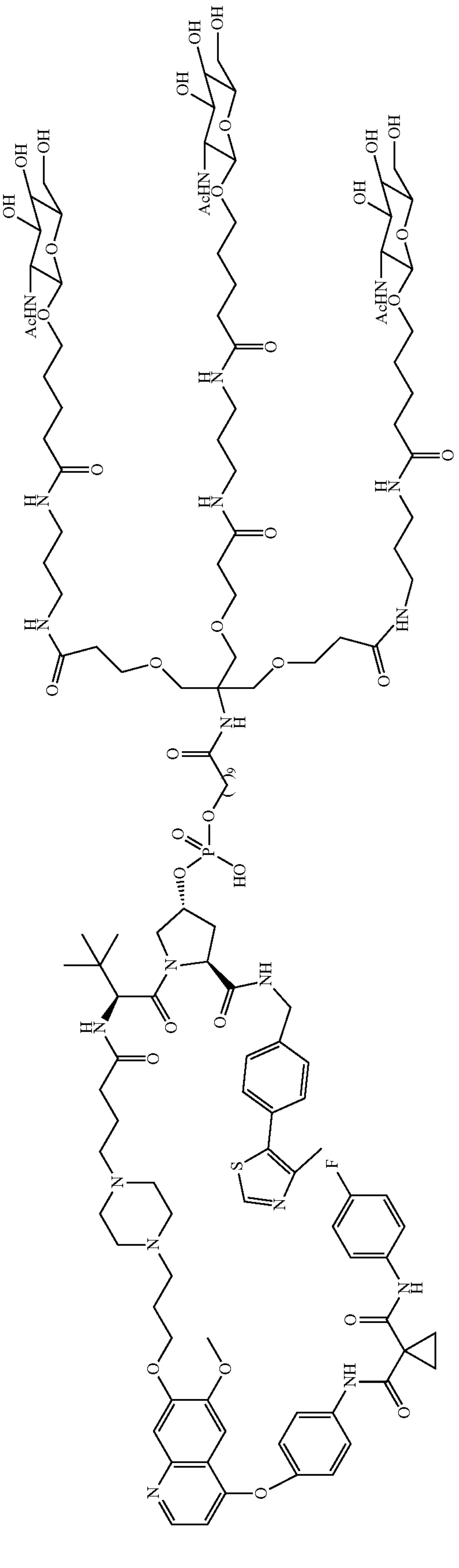
WG-11
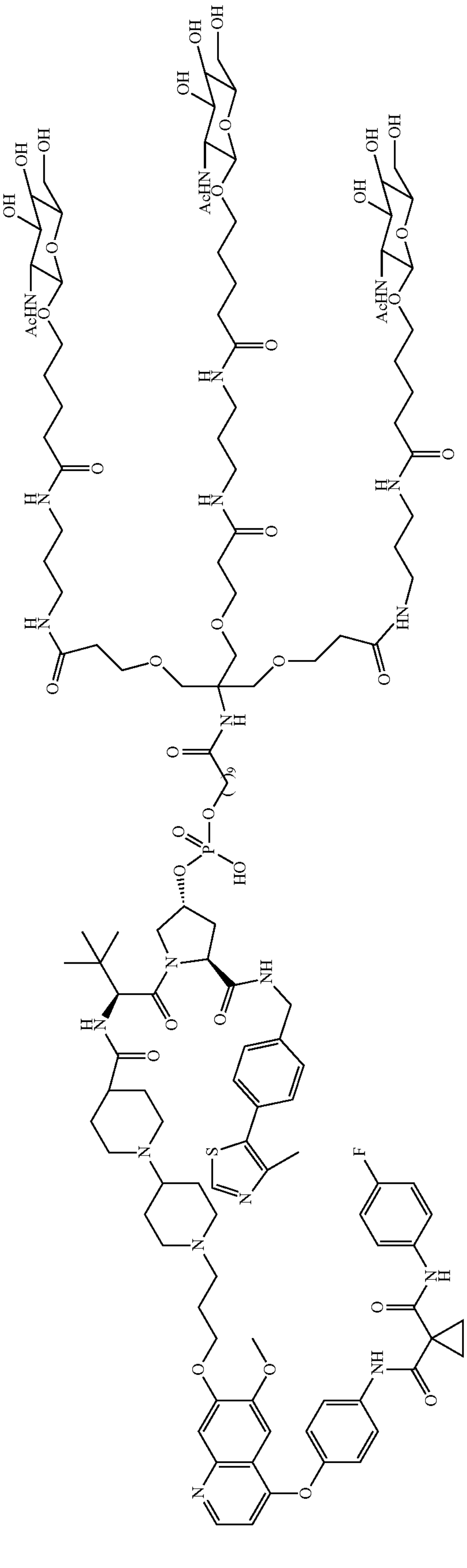

-continued
WG-12
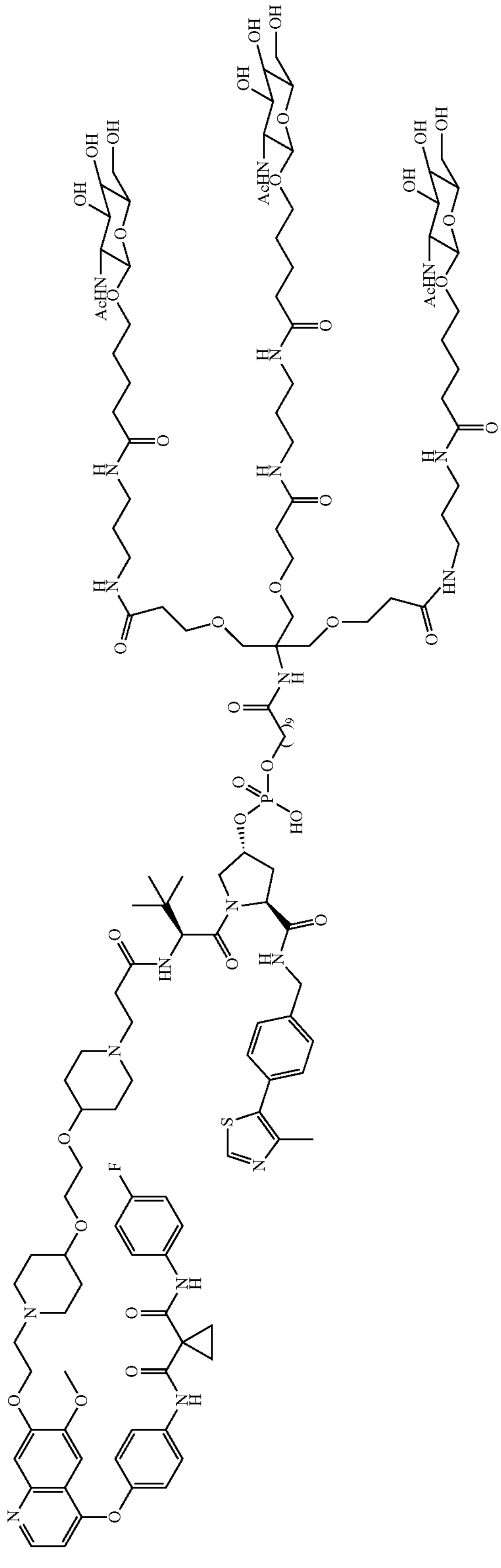
WG-13
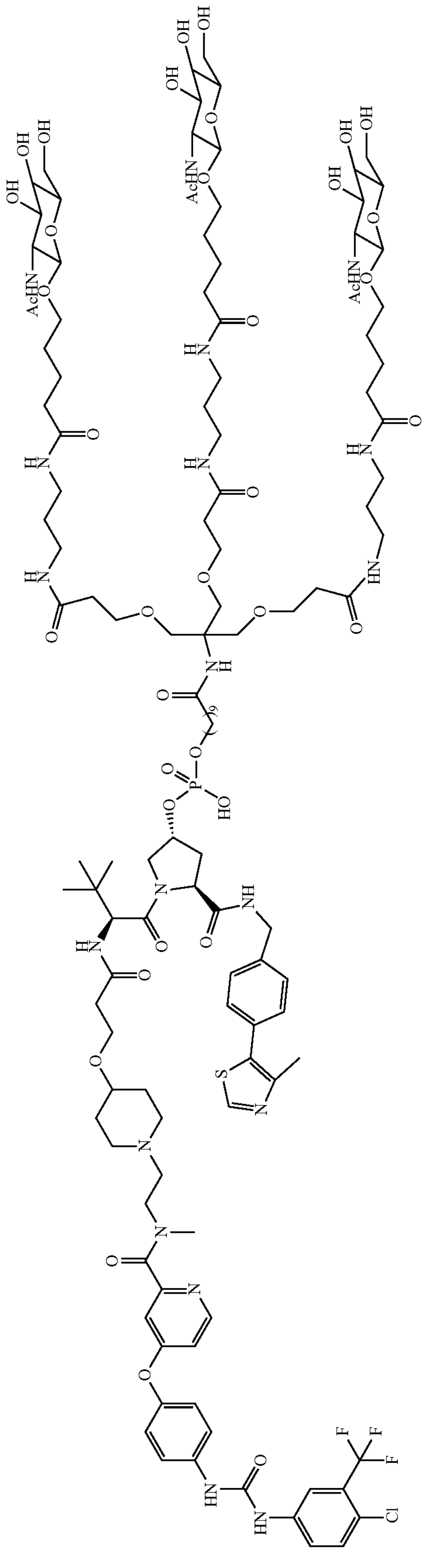

-continued
WG-14
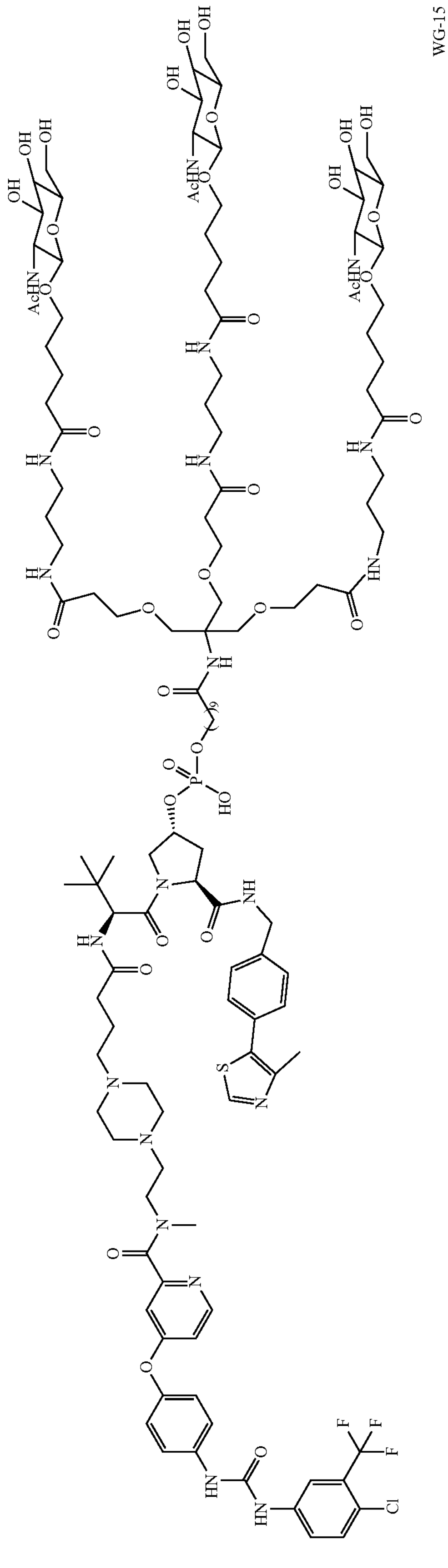
WG-15
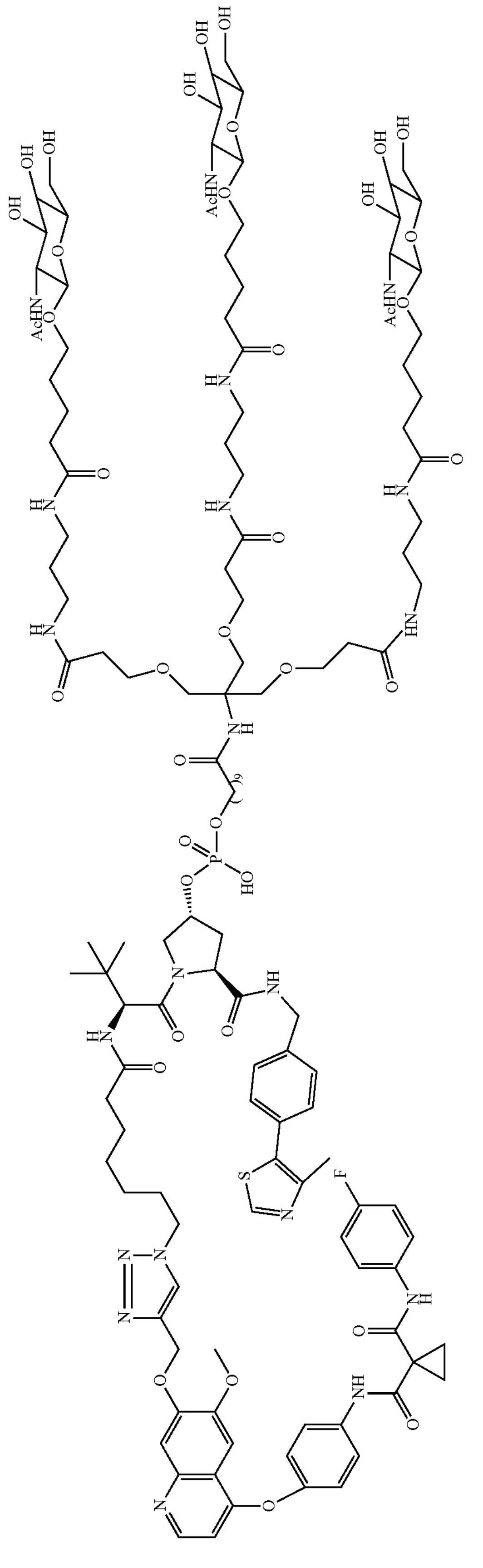

-continued
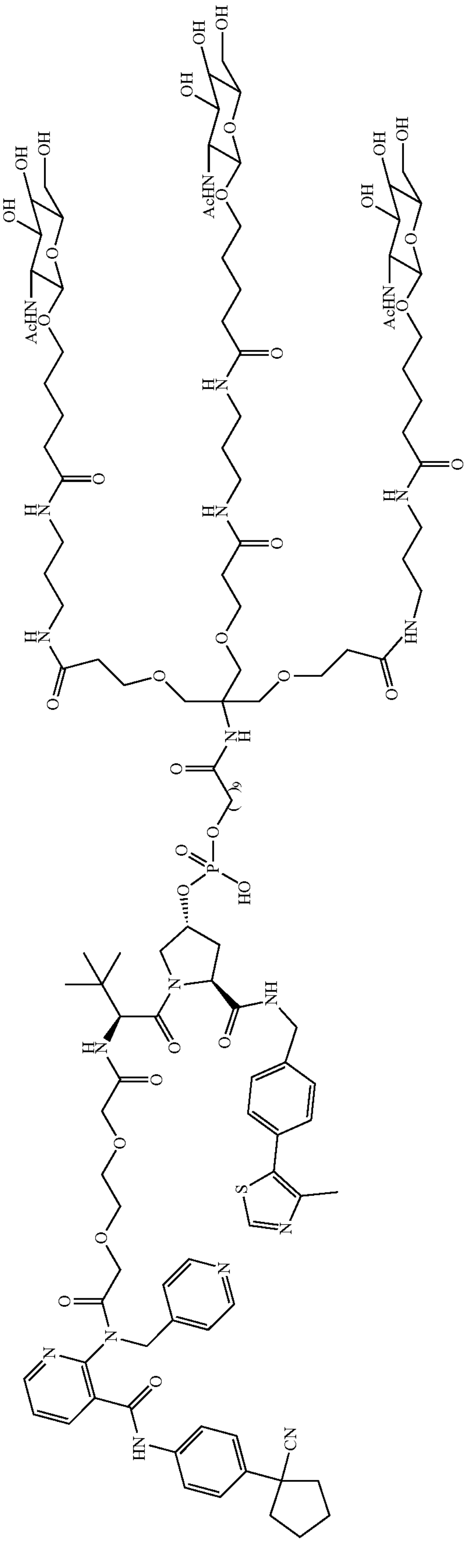
WG-16
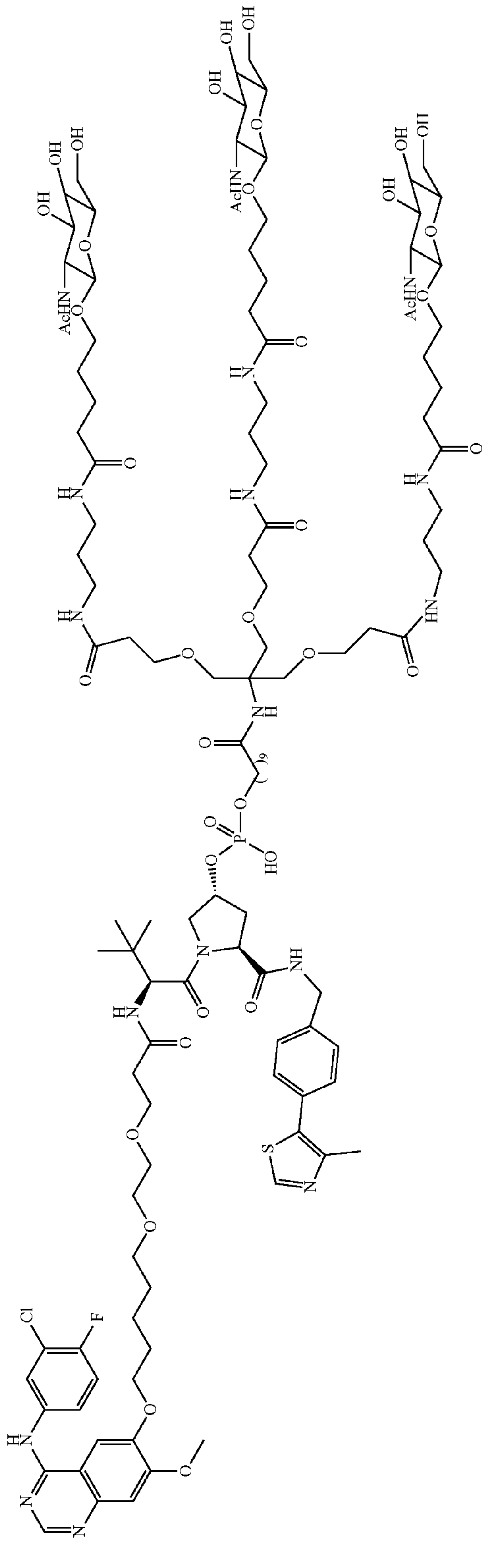
WG-17

-continued
WG-18
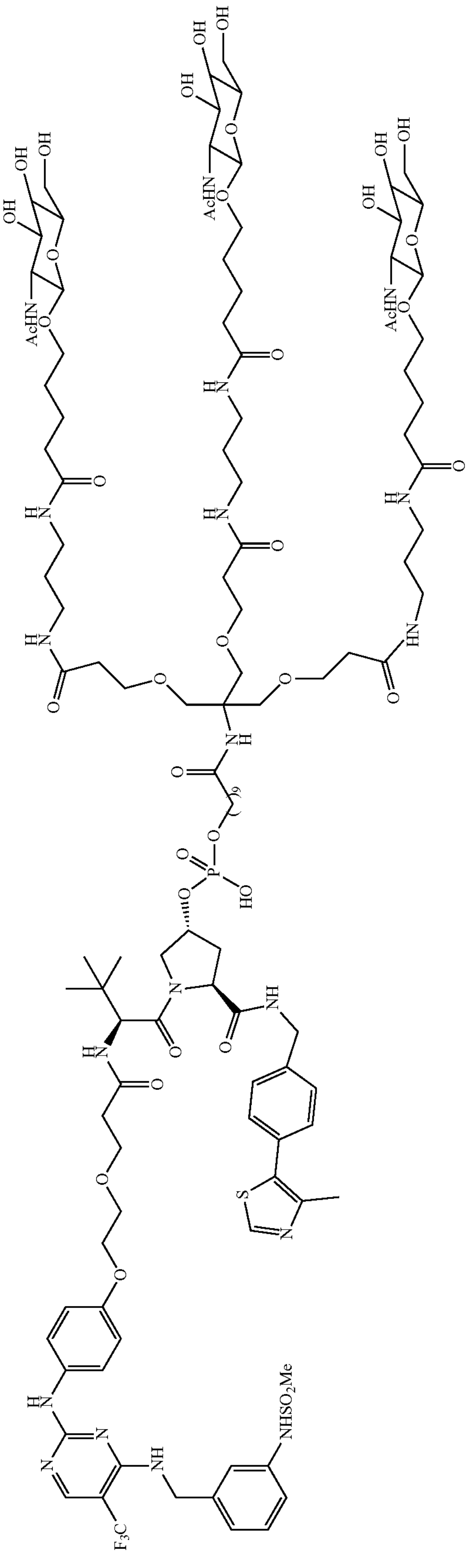
WG-19
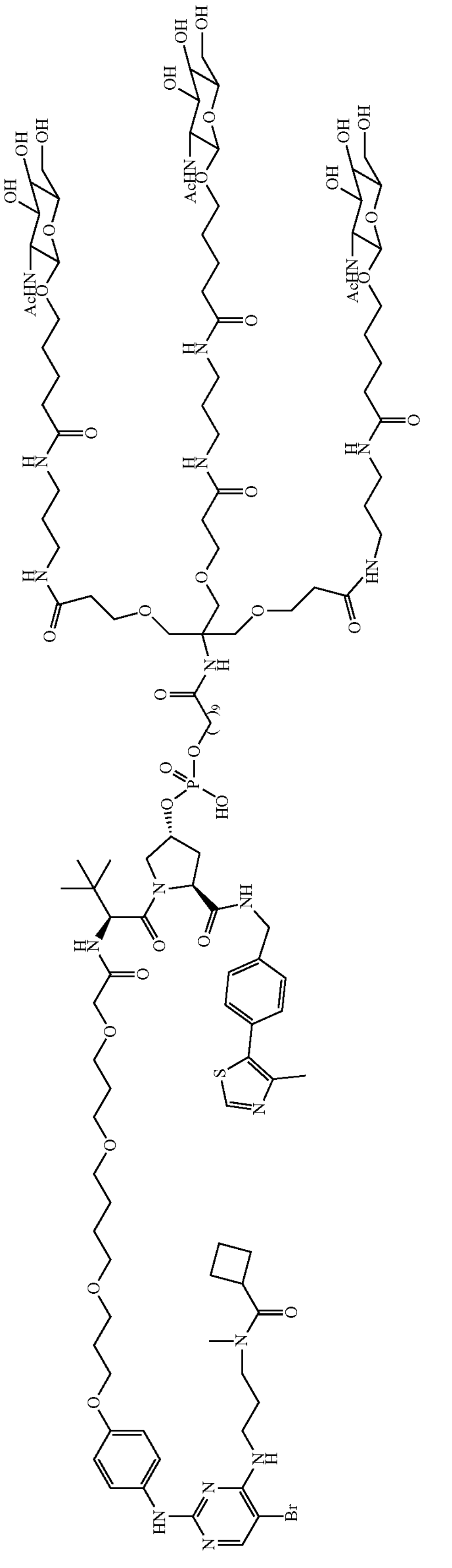

-continued
WG-20
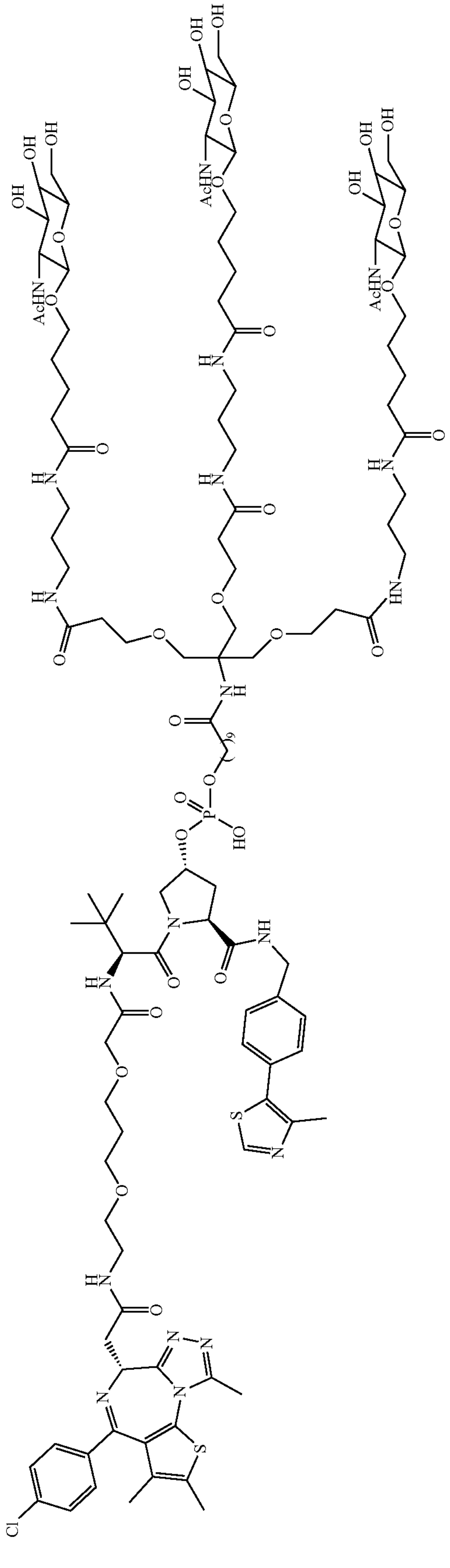
WG-21
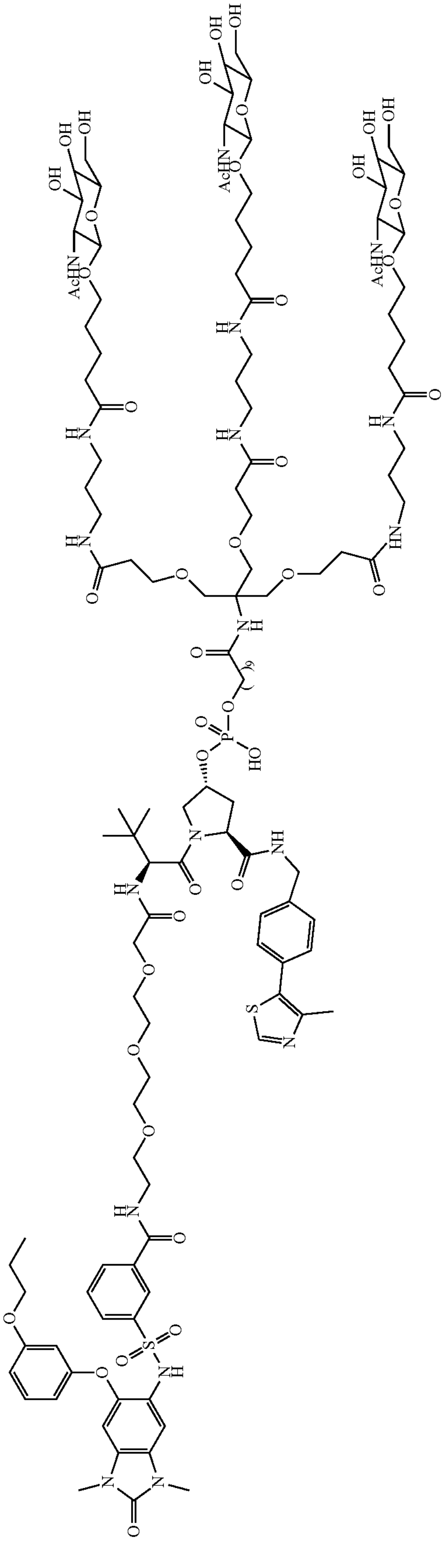

-continued
WG-22
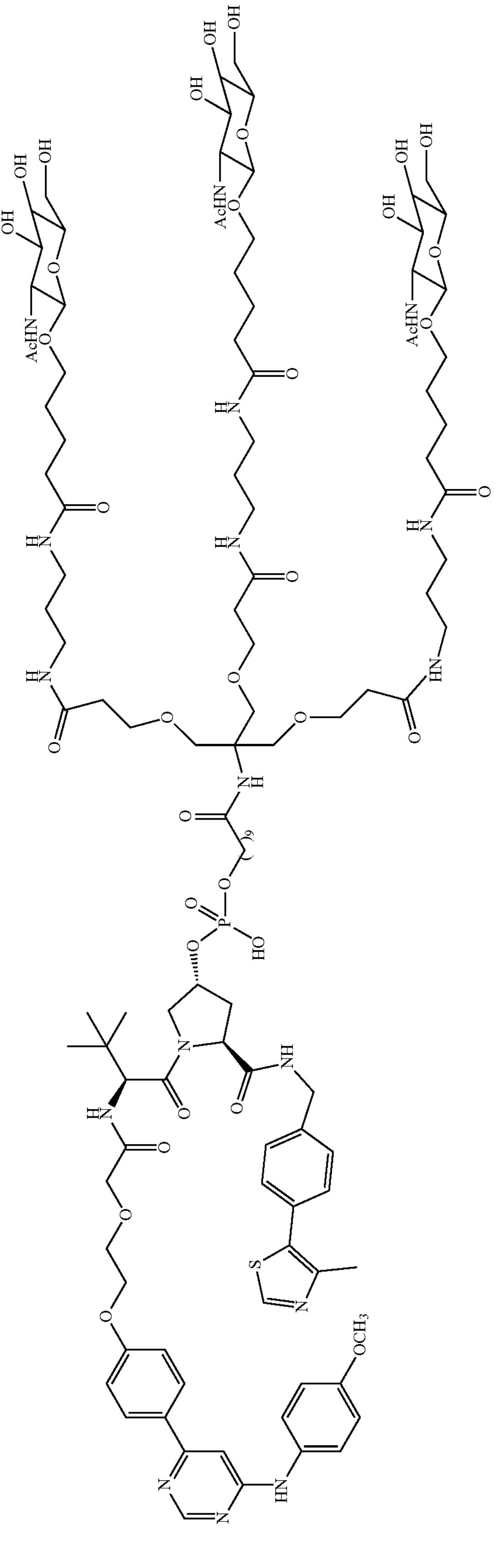

-continued
WG-23
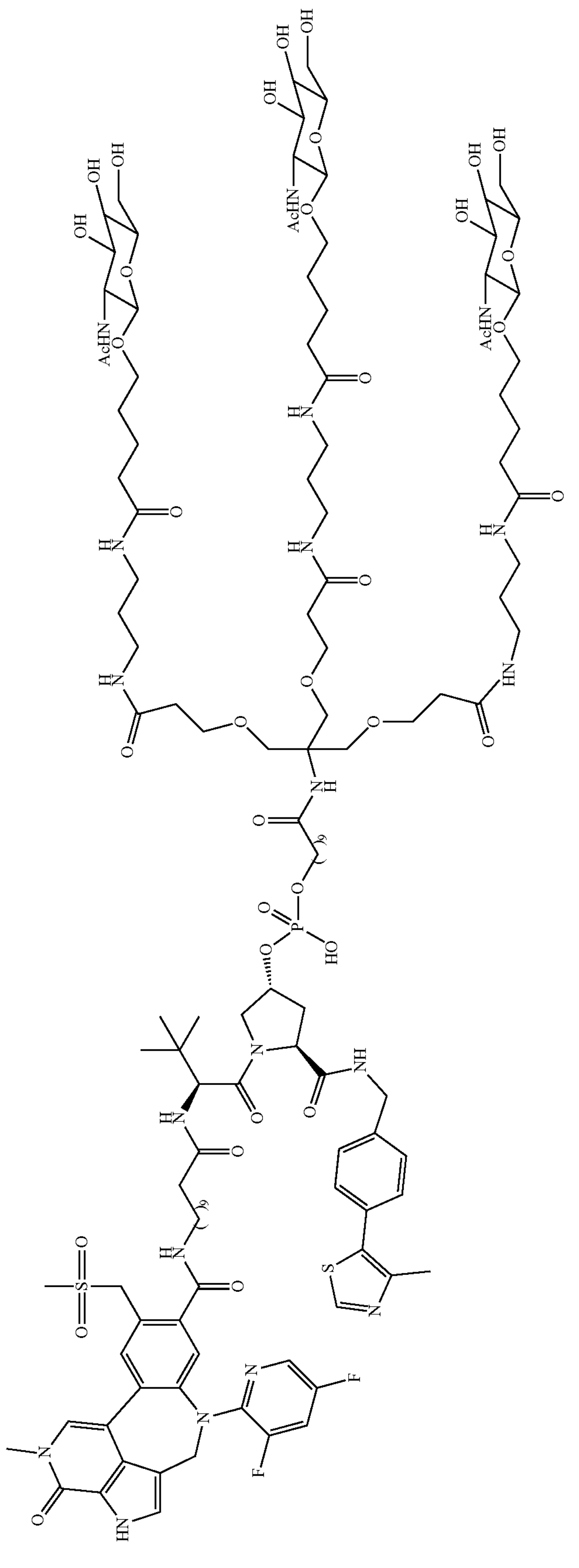

-continued
WG-24
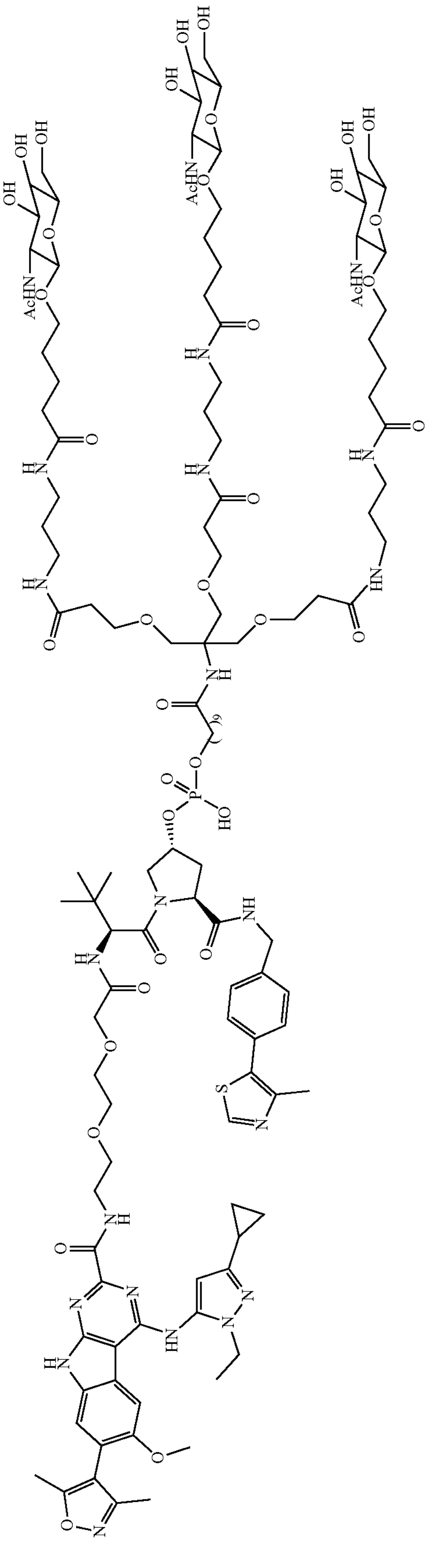
WG-25
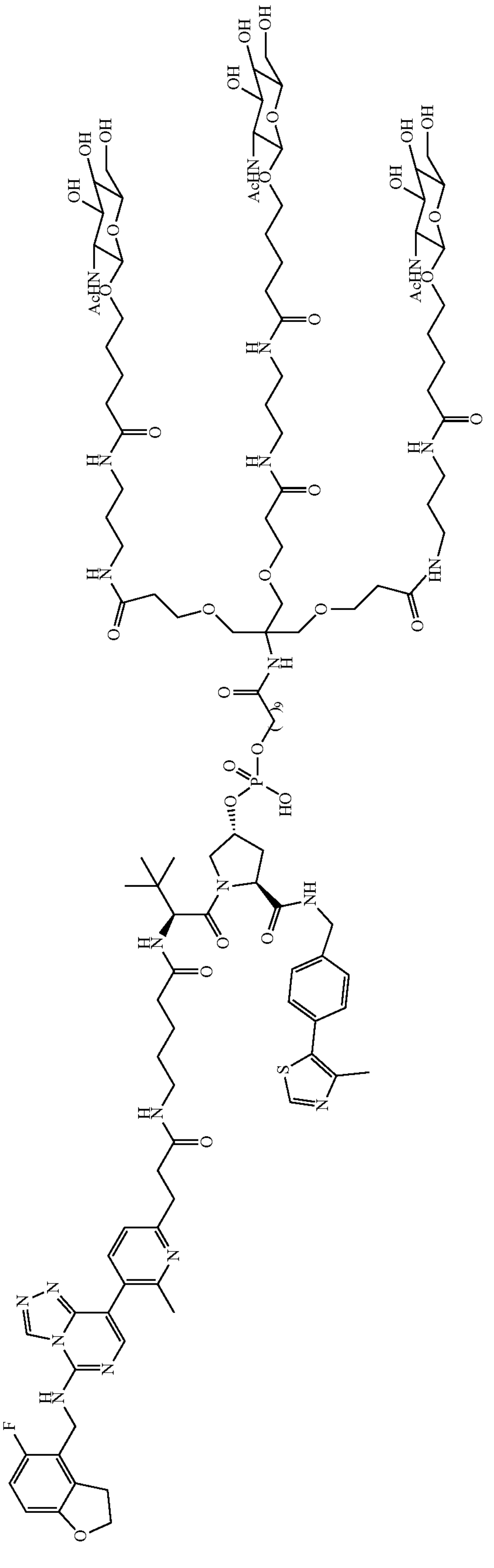

Preferably, the compound is selected from WG-1, WG-2, WG-3, WG-4, WG-5, and WG-6.

In a thirteenth aspect, the present invention provides a pharmaceutical composition of any one of the aforementioned compounds.

In a fourteenth aspect, the present invention provides use of any one of the above compounds and pharmaceutical compositions thereof in the manufacture of a medicament for treating tumors, preferably for treating liver cancer.

In a fifteenth aspect, the present invention provides use of any one of the above compounds and pharmaceutical compositions thereof in the manufacture of a medicament for treating liver diseases, preferably for treating hepatitis.

Unless otherwise defined, all terms (including technical terms and scientific terms) used in the present invention have the same meanings as those commonly understood by those skilled in the art to which the present invention belongs.

DETAILED DESCRIPTION OF THE INVENTION

Figure 1:
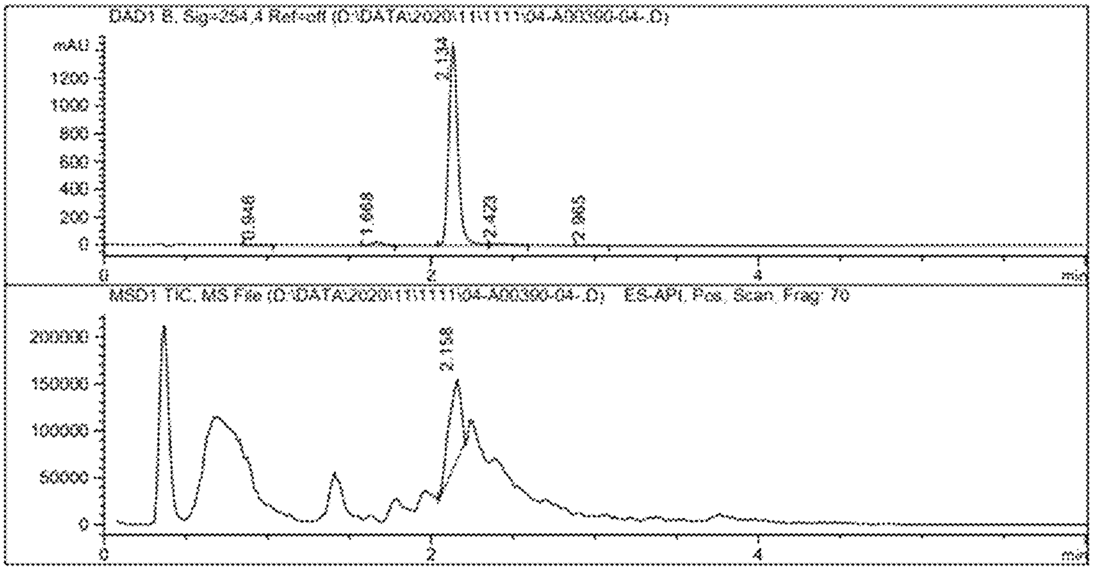
FIG. 1 shows HPLC chromatogram of WG-1 (00300639)
Figure 2:
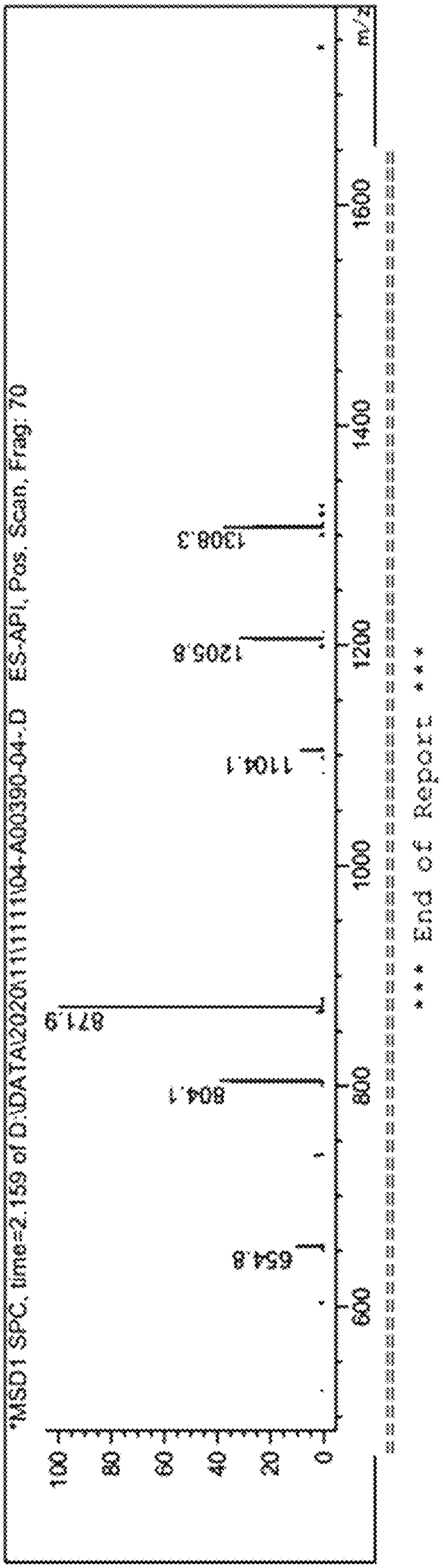
FIG. 2 shows LC/MS chromatogram of WG-1 (00300639)
Figure 3:
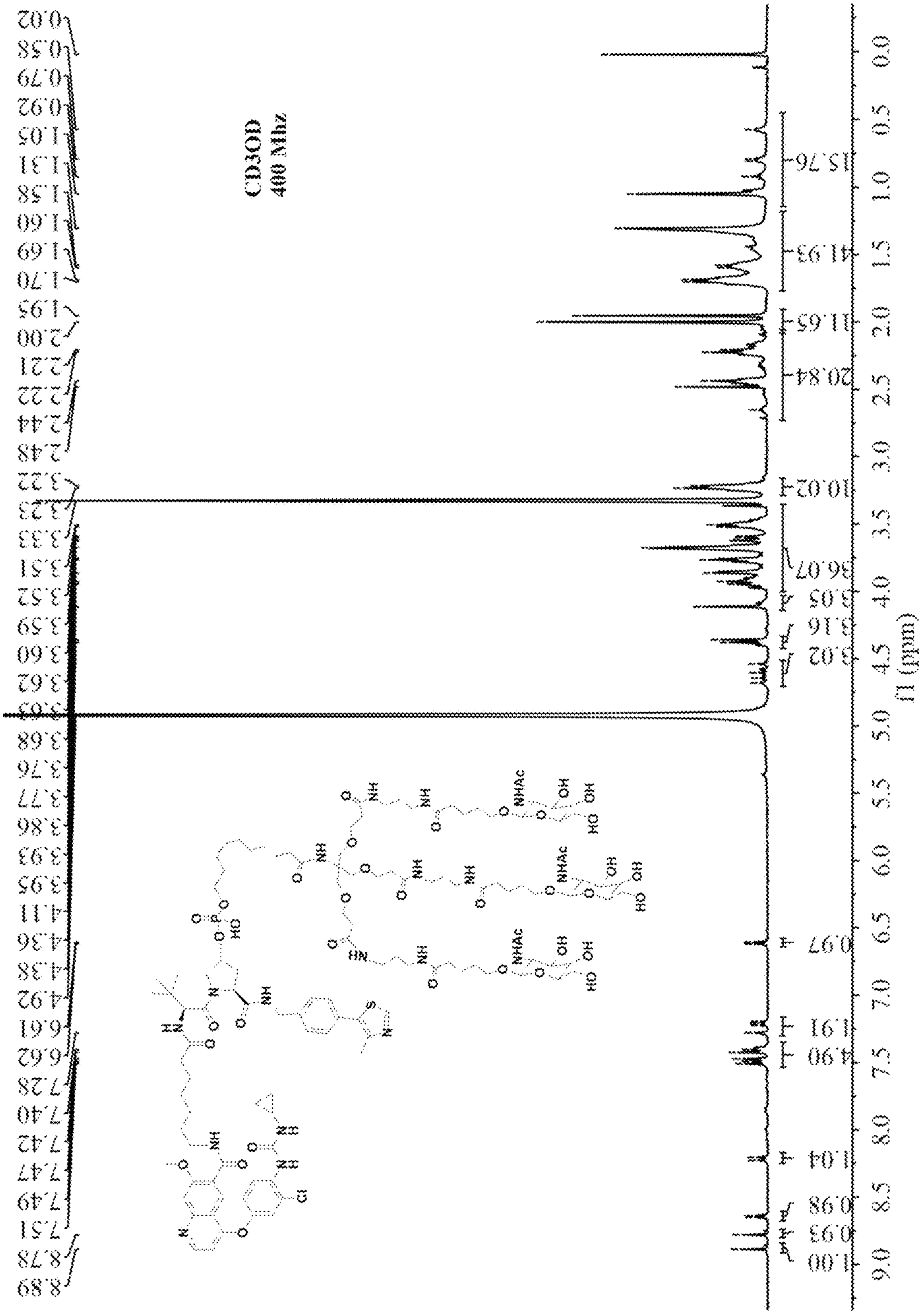
FIG. 3 shows $^{1}$HNMR spectrum of WG-1 (00300639)
Figure 4:
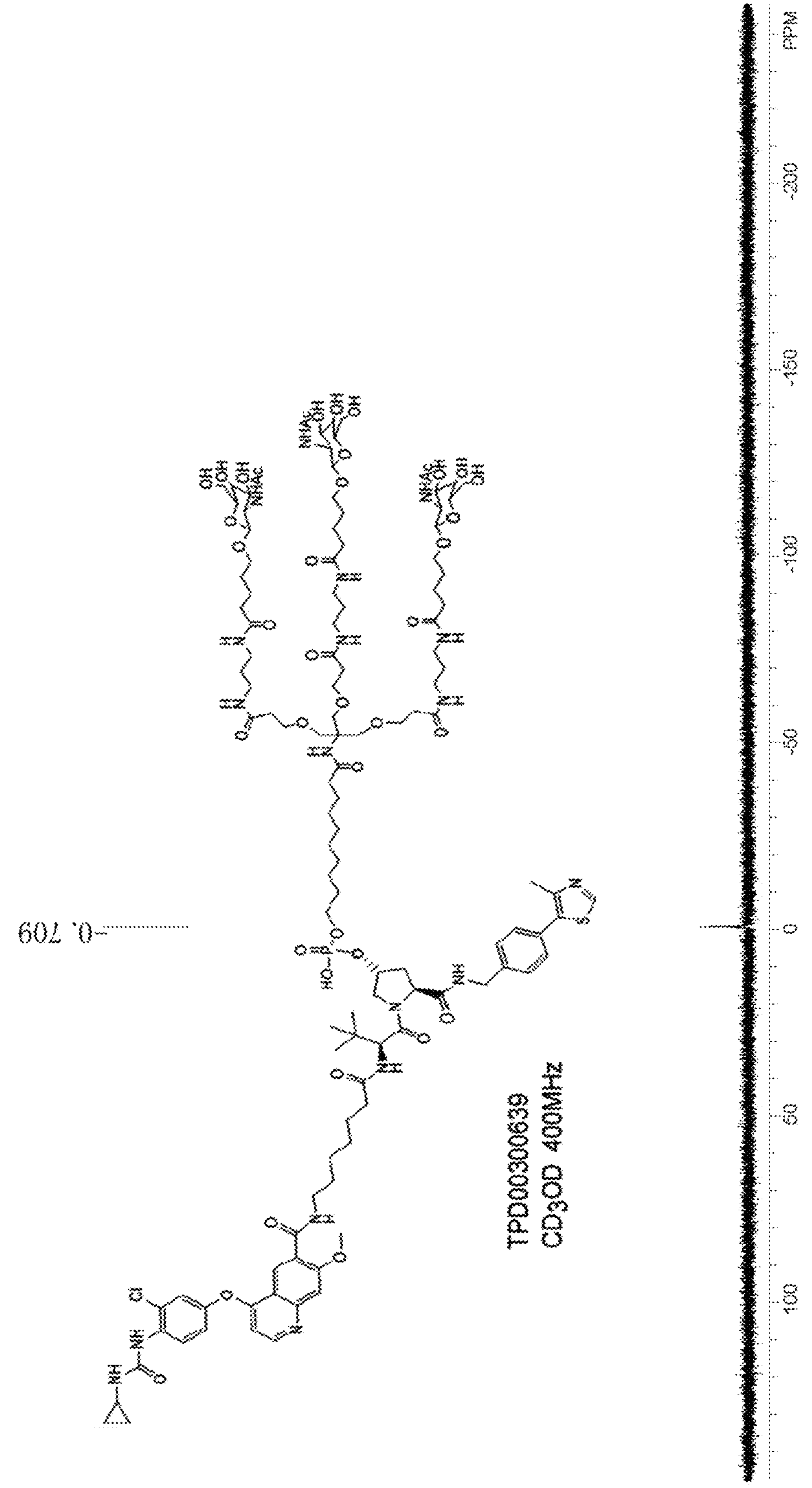
FIG. 4 shows $^{31}$PNMR spectrum of WG-1 (00300639)

The present application will be further illustrated with reference to drawings and following embodiments. However, these embodiments are only for more clearly illustrating, rather than limiting the present invention in any form. The present invention could be implemented in a variety of different ways disclosed herein.

The present invention describes the materials and experimental methods used in the experiment in a general and specific way. Although many materials and operation methods used for the purpose of the present invention are well known in the art, the present invention is still described herein as much detail as possible. In the following, unless otherwise specified, the materials and experimental methods used are well known in the art.

WG series compounds can be synthesized through the following process or by similar route. Among all compounds, WGint4 is the compound A in the general formula of the present invention, which needs to be synthesized individually. WGint8 is the compound CON in the general formula of the present invention, which can be synthesized by referring to the existing technology or purchased from the supplier. Other procedures are share similar routes.

WG-1 (00300639) is exemplified by the following synthesis route:

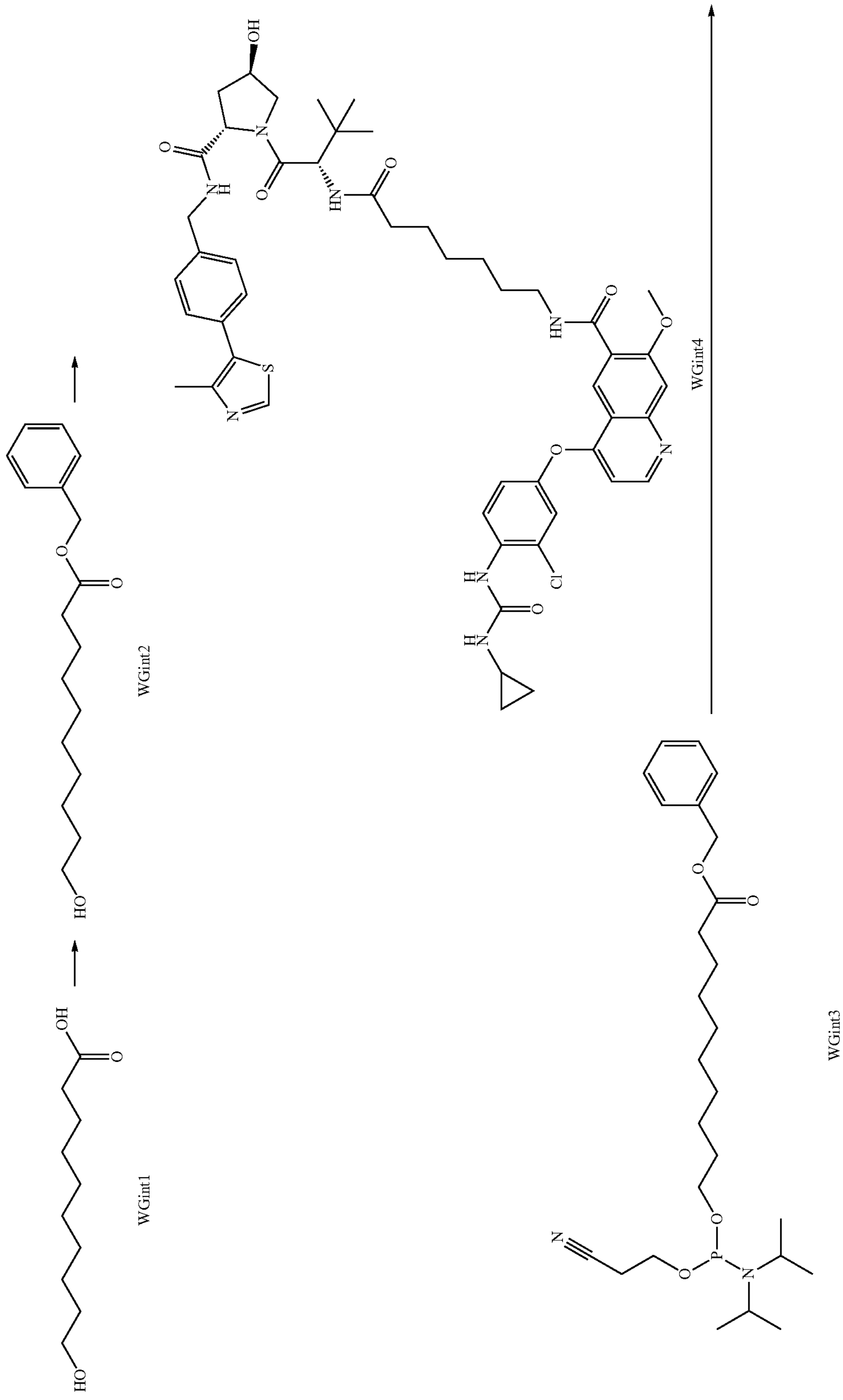
WGint1
WGint2
WGint3
WGint4

-continued
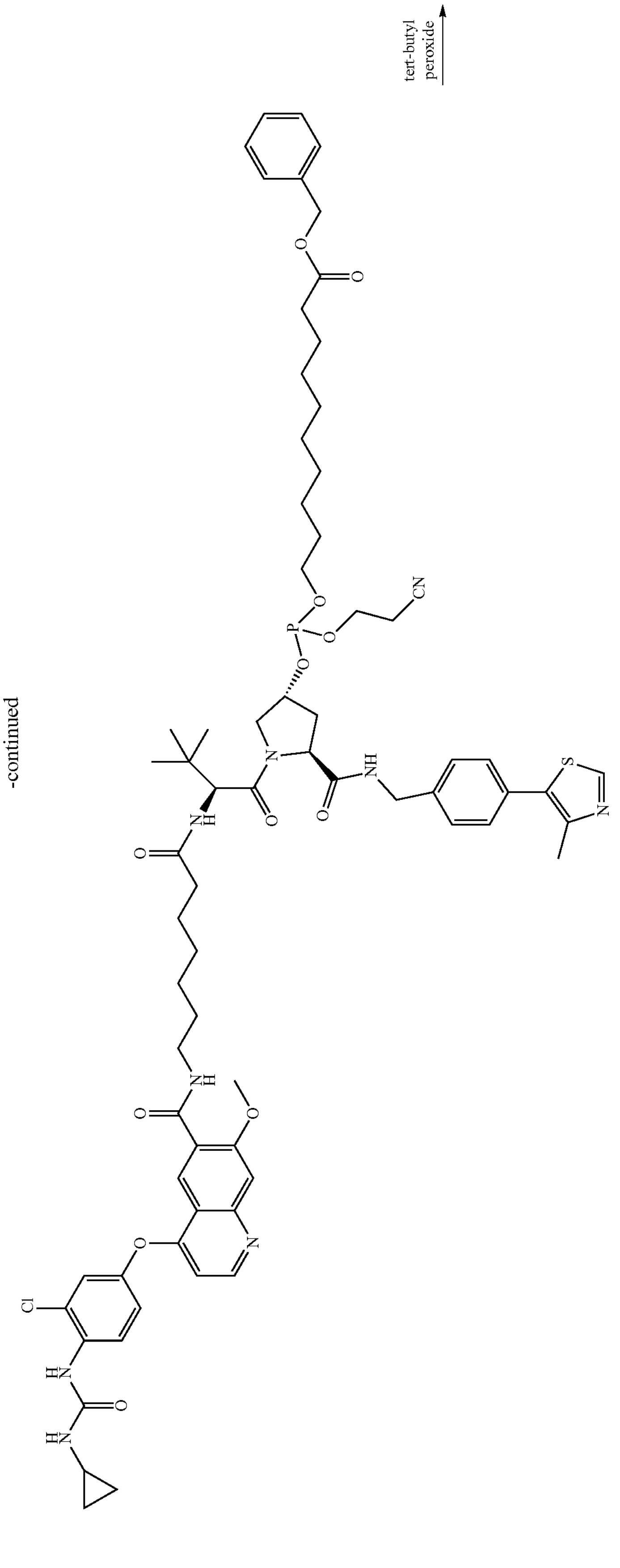
WGint5

-continued
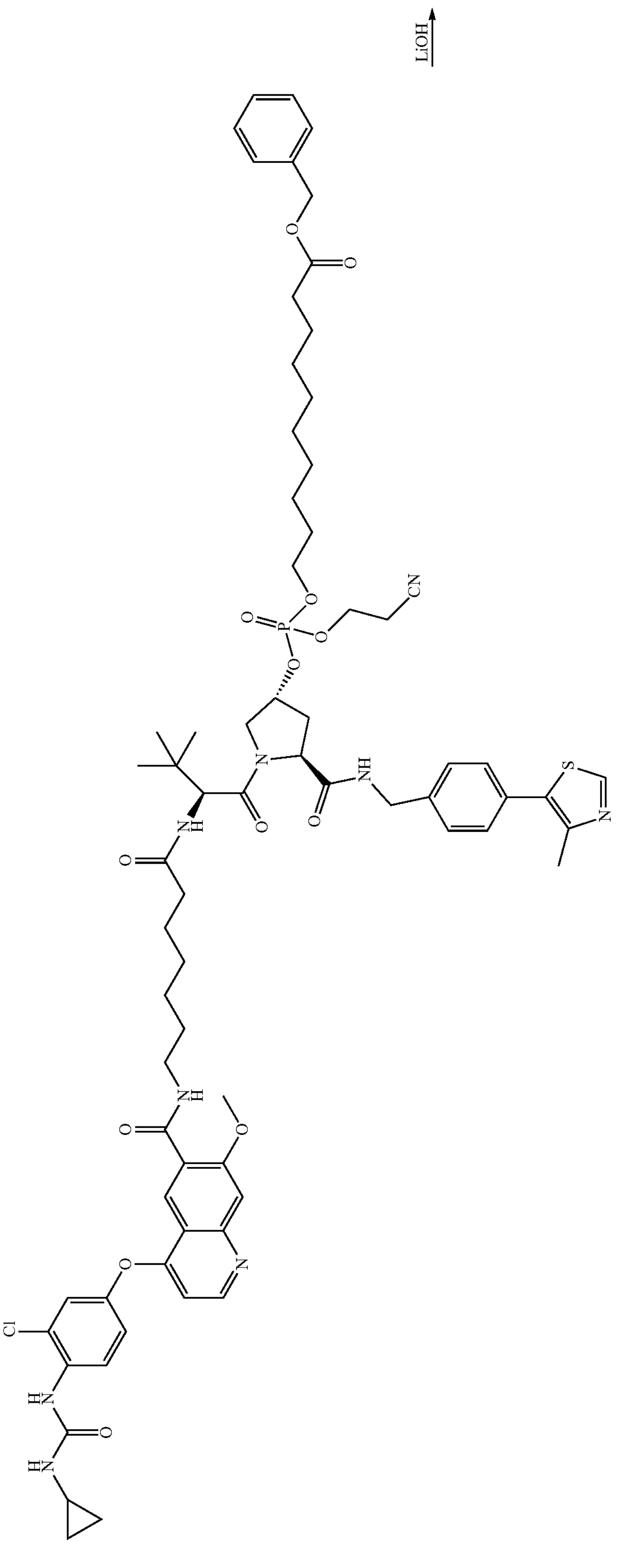
WGint6

-continued
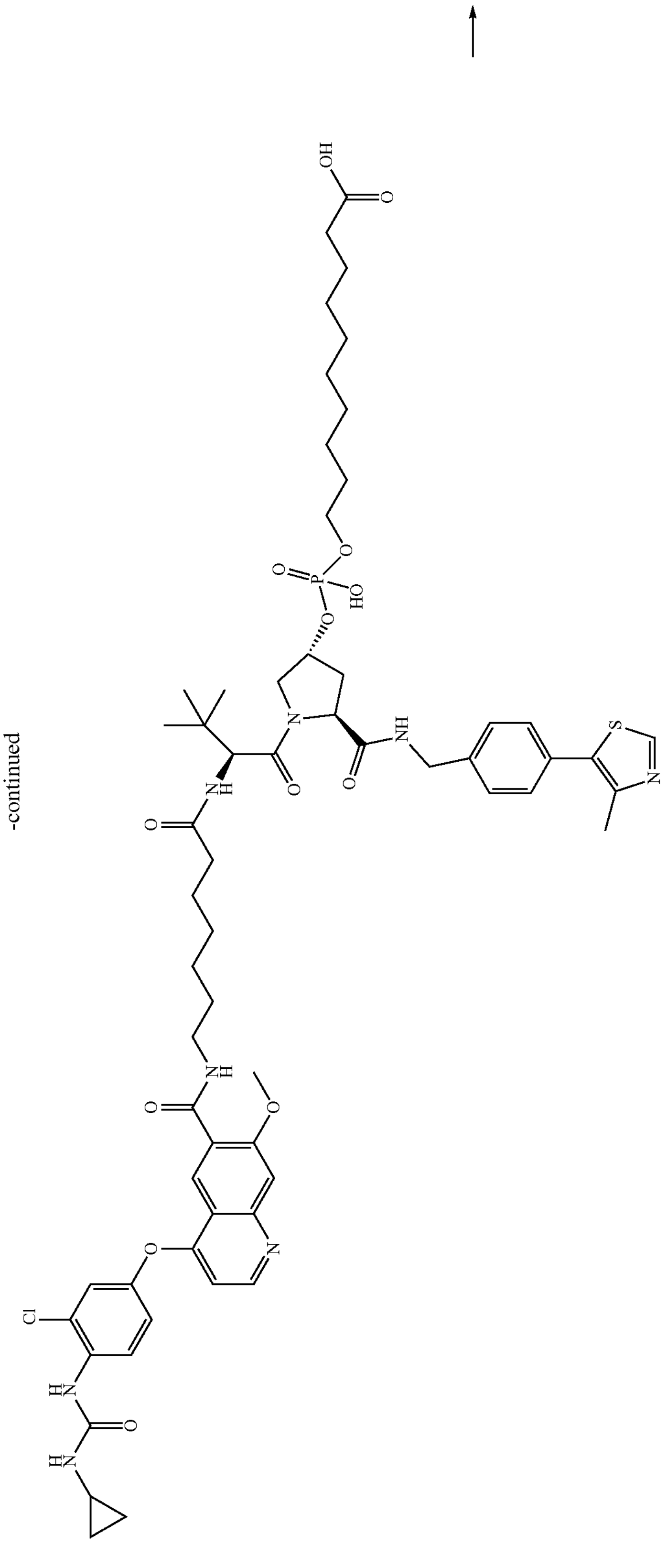
WGint7

-continued
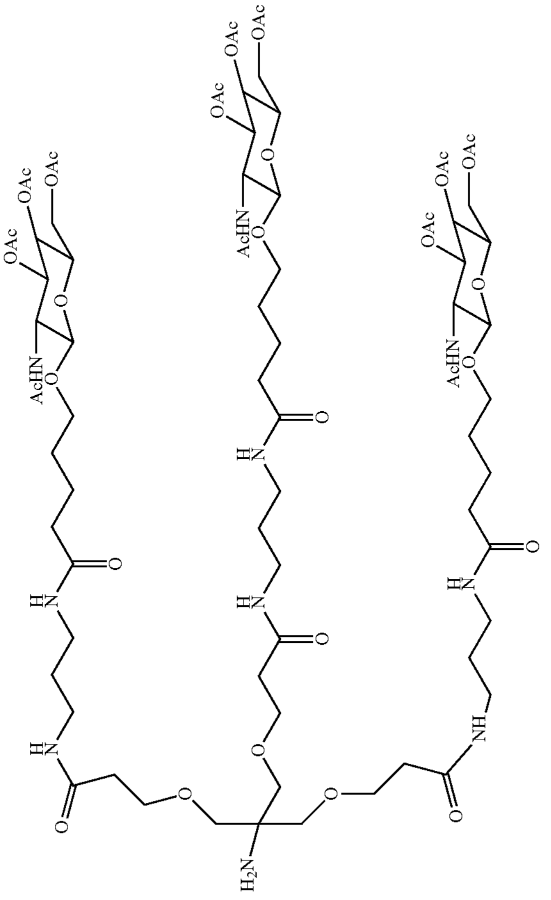
WGint8
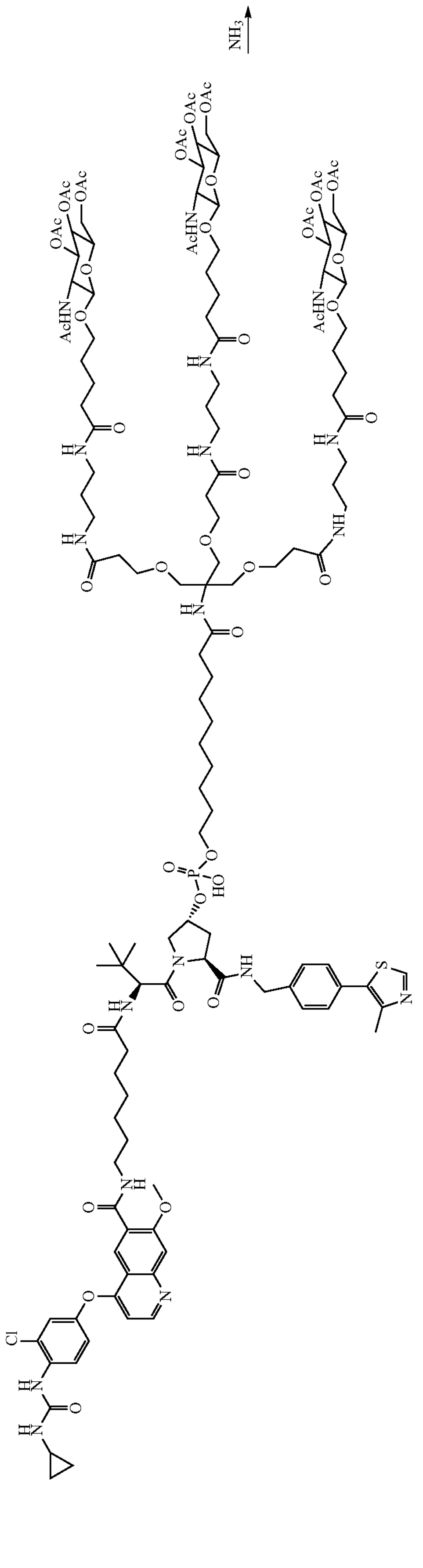
WGint9

-continued
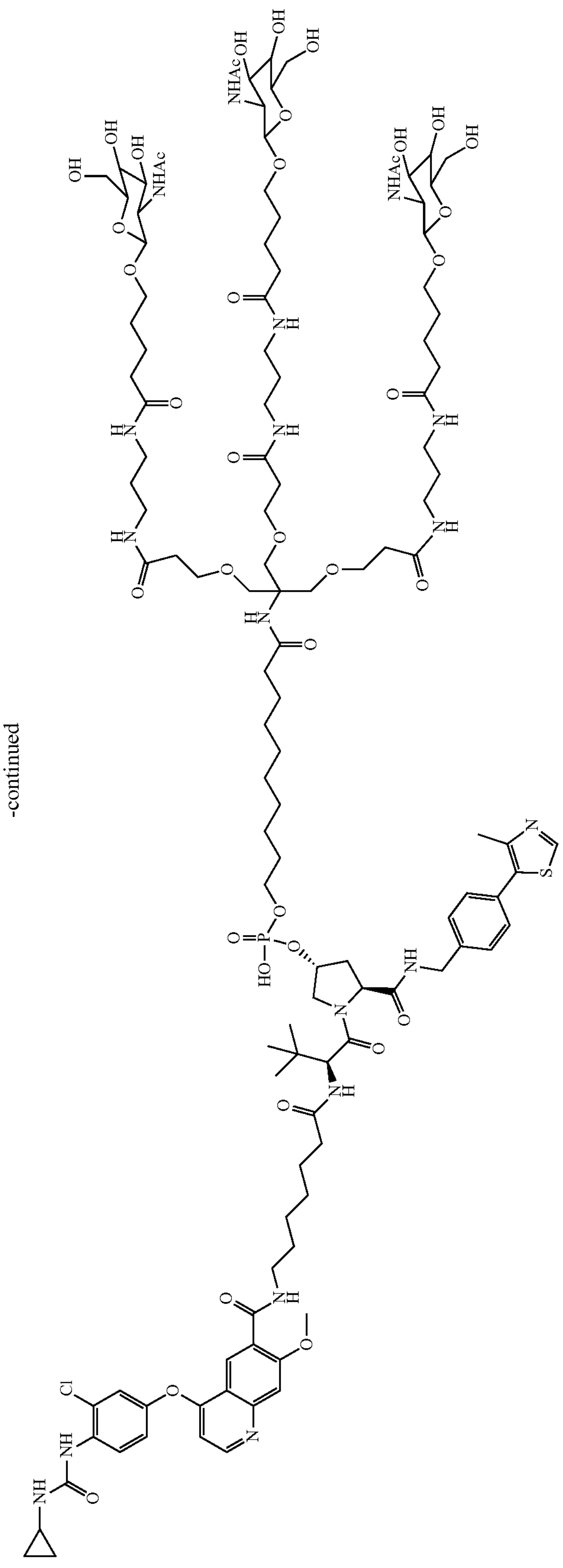
WG.1(00300639)

In comparison with compound WG-1 (00300639), the corresponding WGint4 is WGint4 (003006). The synthesis route of WGint4 (003006) is as follows:
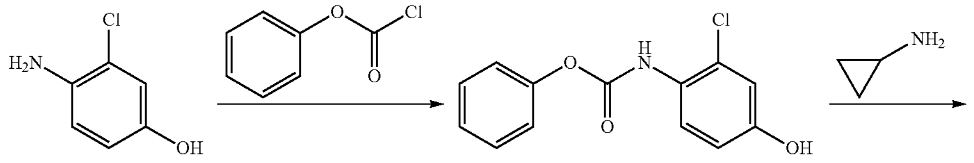
003006int1 003006int2
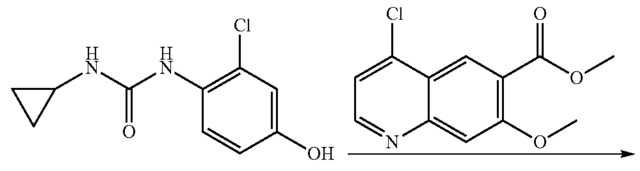
003006int3
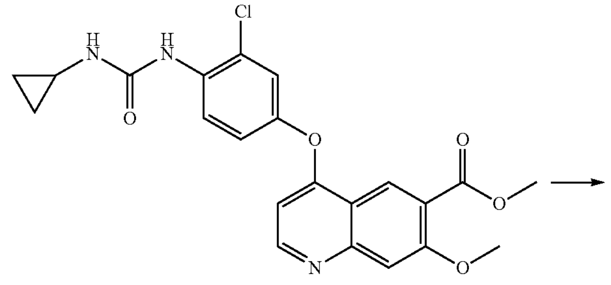
003006int4
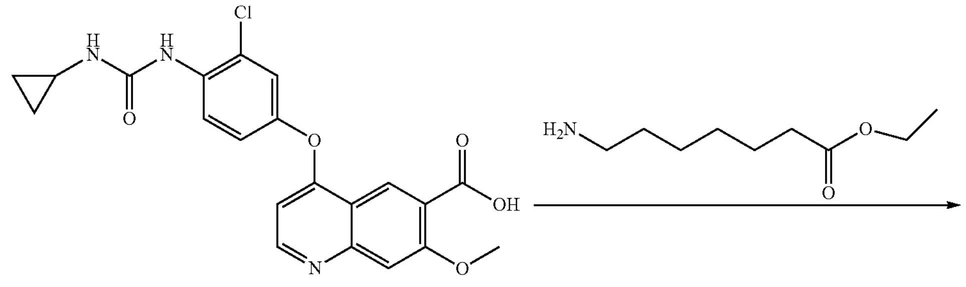
003006int5
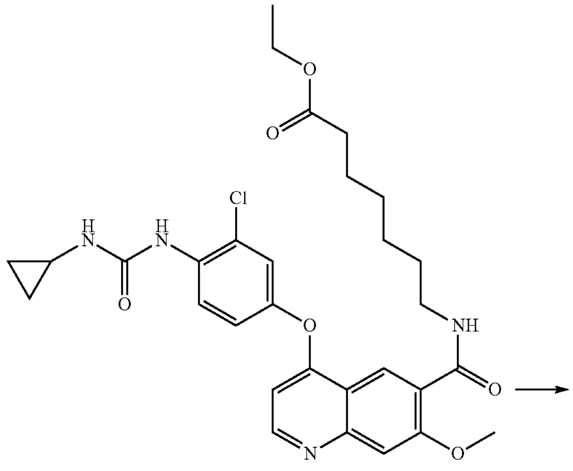
003006int6

-continued
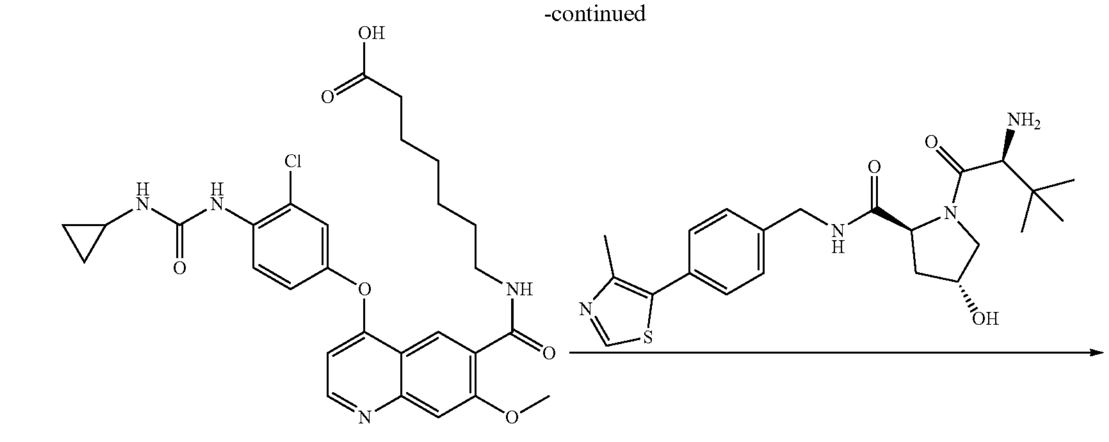
003006int7
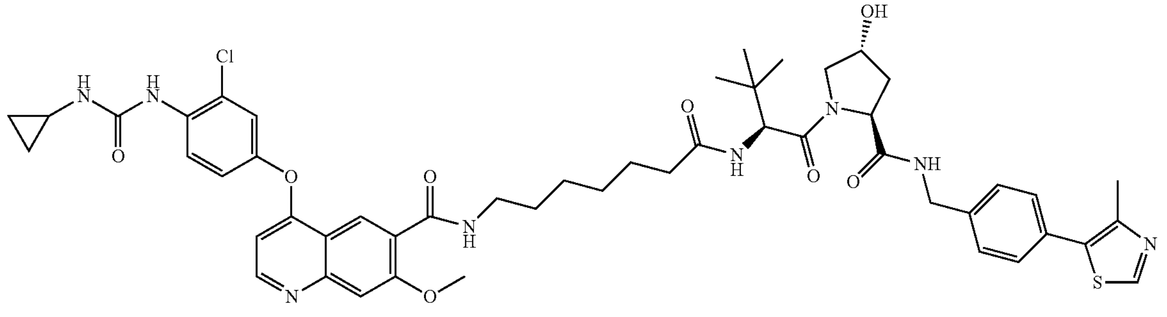
WGInt4(003006)
In comparison with compounds WG-4 (00500639) and WG-5 (00600639), the corresponding WGint4 are WGint4 (005000) and WGint4 (006000). The synthetic method is as follows:
(1) Synthesis of Compound Side 1
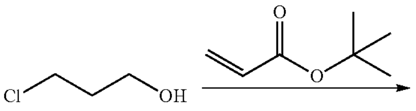
005000int1
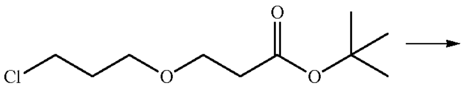
005000int2
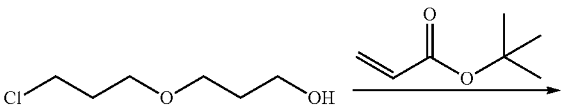
005000int3
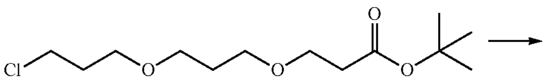
005000int4
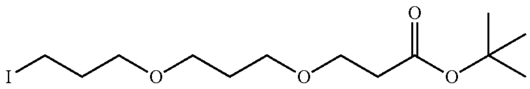
side 1
(2) Synthesis of Compound Core 1
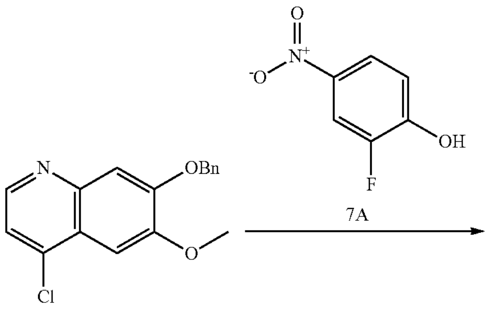
005000int7
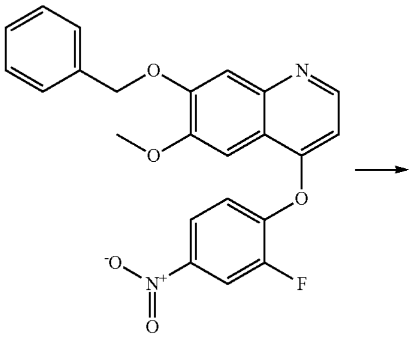
005000int8

-continued
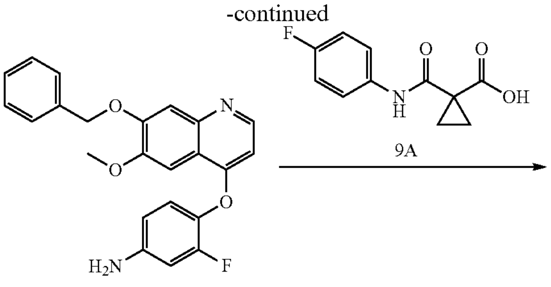
005000int9
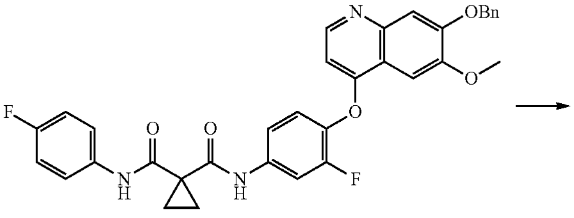
005000int10
-continued
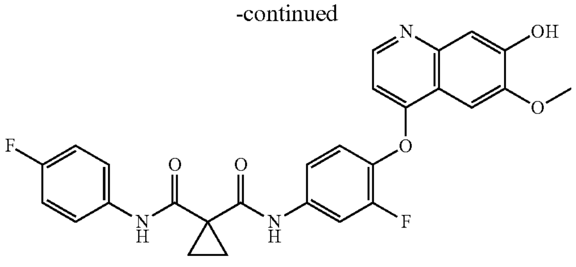
Core 1
(3) Synthesis of Compound WGint4 (006000)
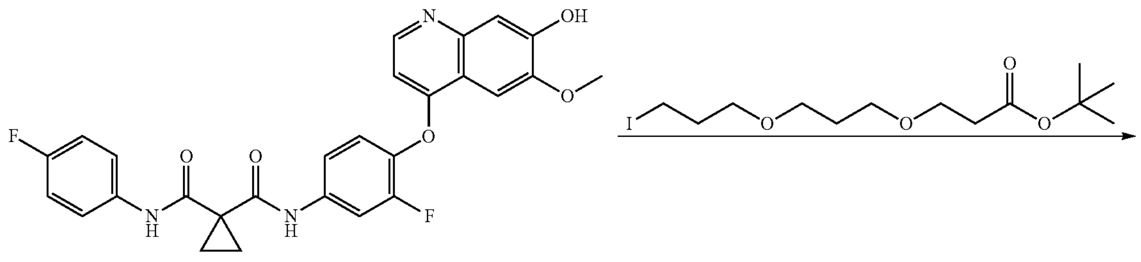
Core 1
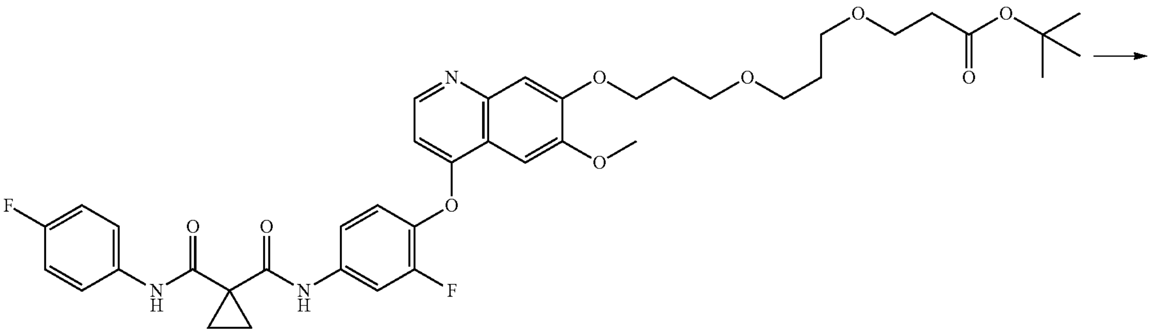
006000int11
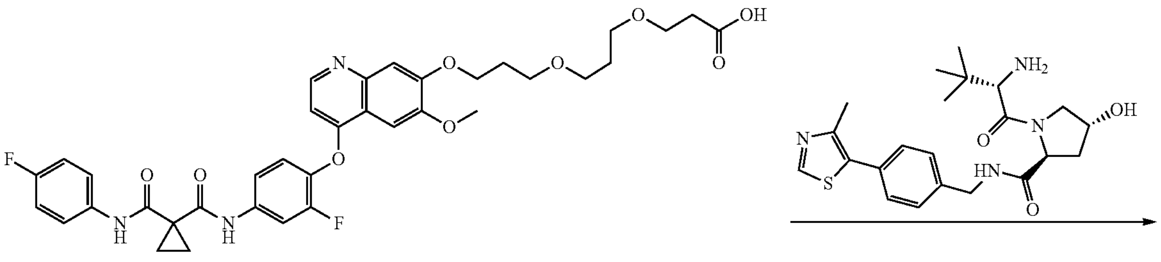
006000int12

-continued
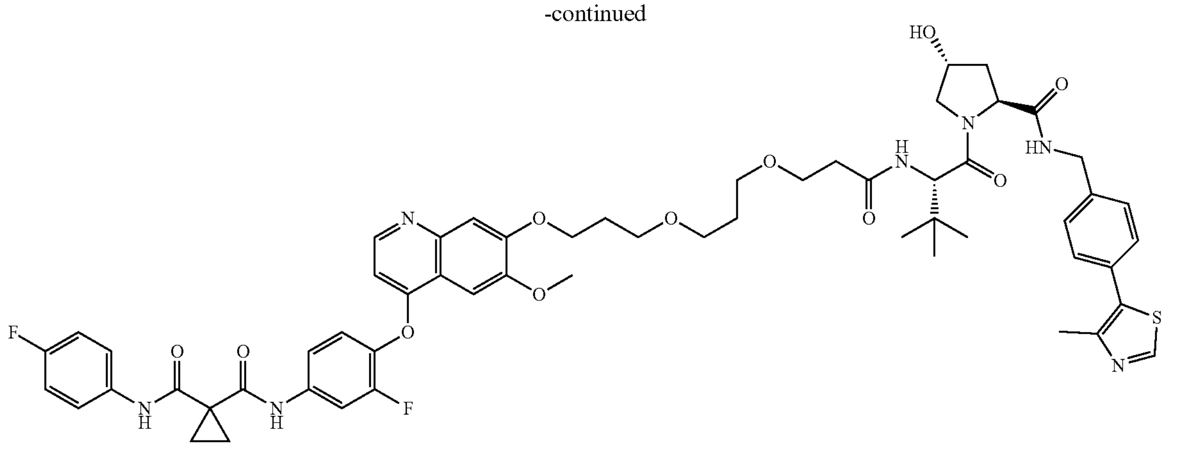
WGint4(006000)
(4) Synthesis of Compound WGint4 (005000)
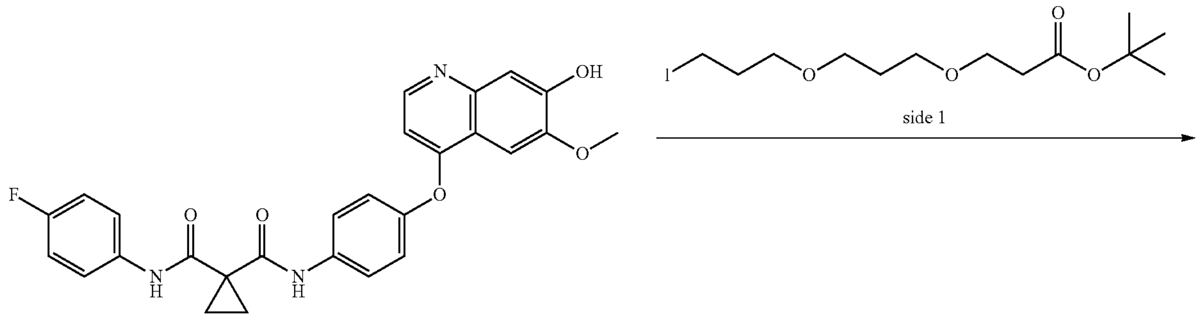
Core 2
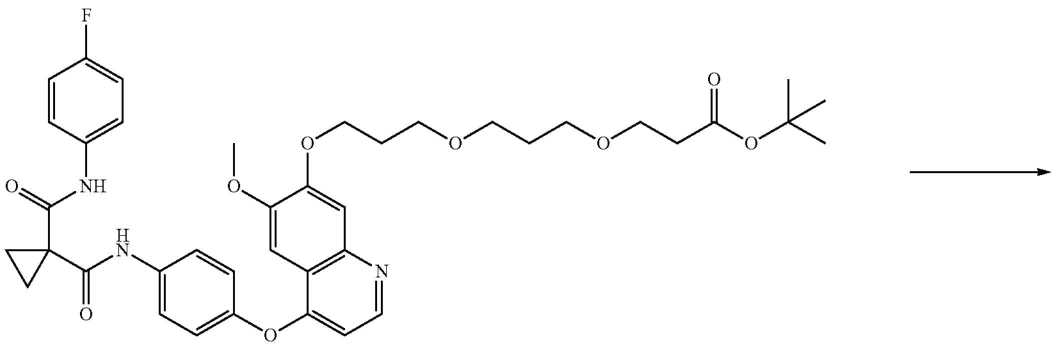
005000int13

-continued

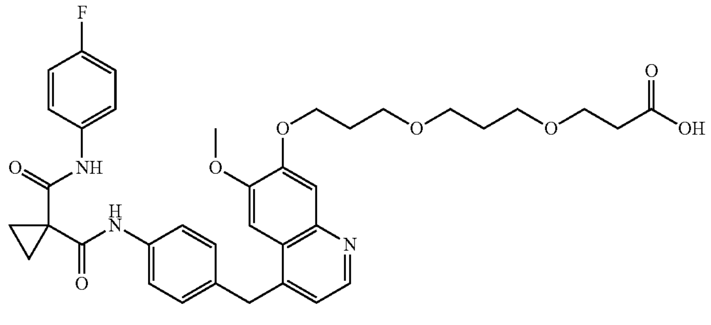

005000int14

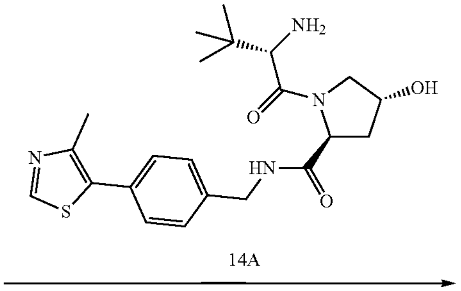

14A

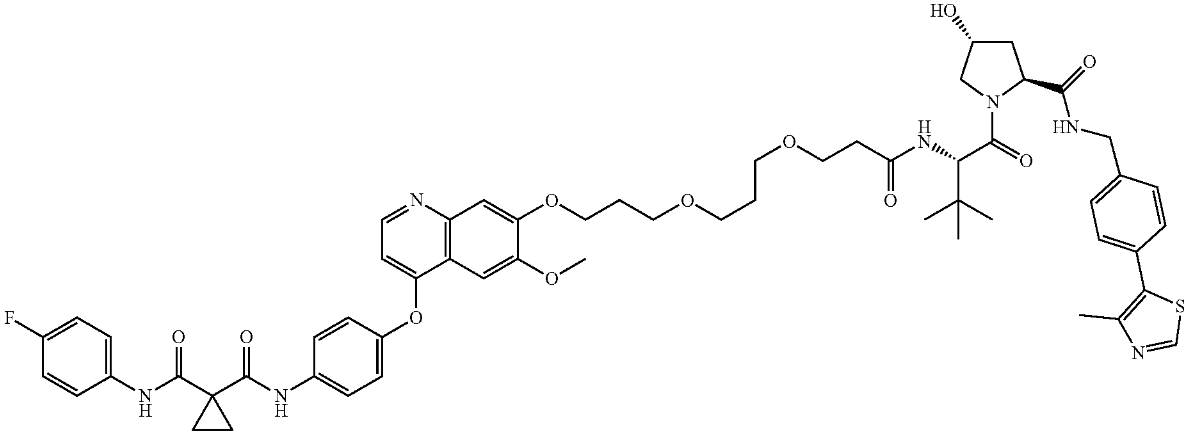

005000

The synthesis of other compounds within the scope of this application can be achieved following the route mentioned above and selecting corresponding raw materials.

Example 1 Synthesis of Compound WGint2

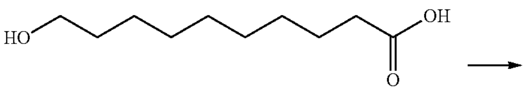

WGint1

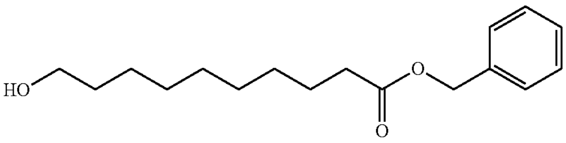

WGint2

A solution of 10-hydroxydecanoic acid (10.0 g, 53.2 mmol) in DMF (250 mL) was treated with potassium bicarbonate (5.32 g, 53.2 mmol) followed by benzyl bromide (9.10 g, 53.2 mmol) and was then stirred for 18 h at room temperature under argon. The solvent was evaporated and the residue was partitioned between EA and water. The aqueous layer was washed with EA and the combined organic extracts were dried over anhydrous magnesium sulfate. The resulting crude material was purified with silica gel flash chromatography to give compound WGint2 (8.0 g) as a white solid: LC/MS (ESI) m/z: $[M+H]^+$ 279.

Example 2 Synthesis of Compound WGint3

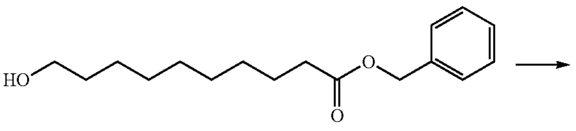

WGint2

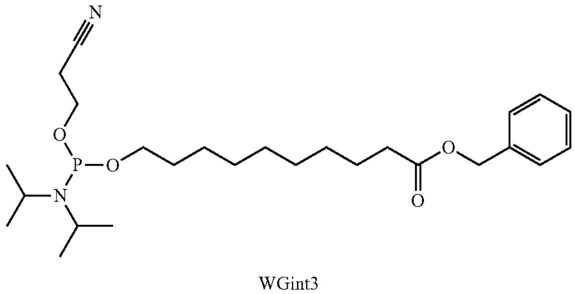

WGint3

To a solution of compound WGint2 (5.0 g, 18.0 mmol) in 100 mL of anhydrous dichloromethane containing diisopropylammonium tetrazolide (4.6 g, 27.0 mmol) was added 2-cyanoethoxy-N,N,N,N-tetraisopropyl phosphorodiamidite (9.0 mL, 27.0 mmol), and the mixture was stirred for 6 h at room temperature, until TLC revealed complete reaction. Dichloromethane was then removed by evaporation and the product was taken up in ethyl acetate, washed with 5% sodium bicarbonate solution and brine, dried over anhydrous sodium sulfate and evaporated to a small volume. The product was chromatographed on a silica gel column eluted with 10-35% ethyl acetate in hexane+2% triethylamine to give compound WGint3 (2.5 g). The intermediate is directly used in the next reaction.

Example 3 Synthesis of Compound WGint6

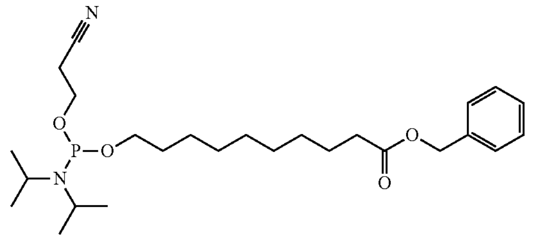

WGint3

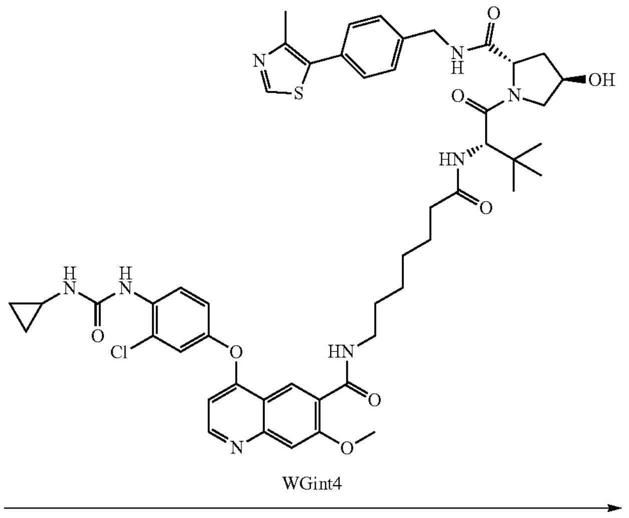

WGint4

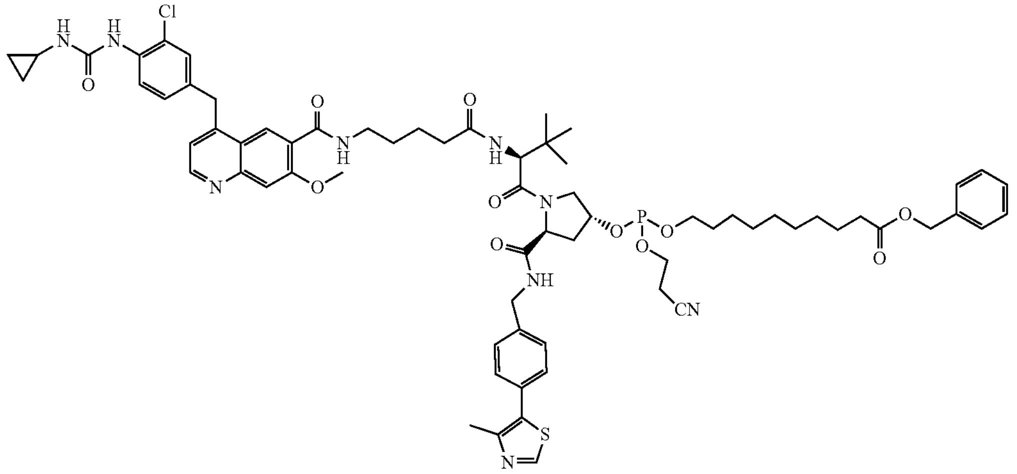

WGint5

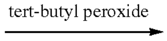

-continued

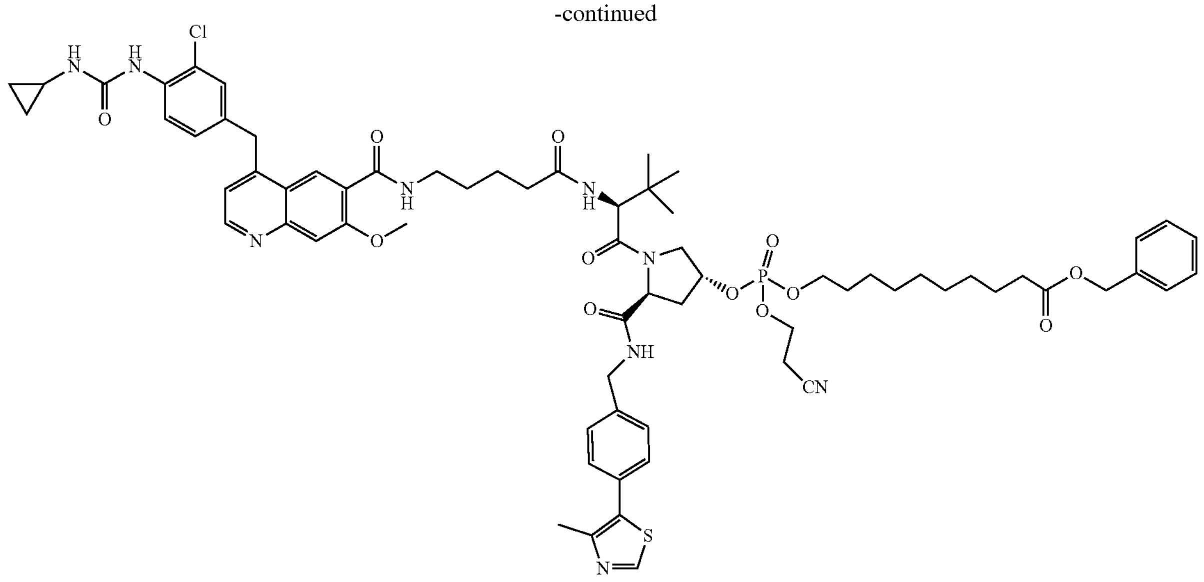

WGint6

The mixture of the compound WGint3 (2.5 g, 5.2 mmol) and compound WGint4 (0.5 g, 0.52 mmol) in ACN (25 mL) was added in tetrazoler (145 mg, 2.1 mmol) and stirred overnight. Tert-butyl peroxide in decane (2 mL, 5 M) was added dropwise at 0° C. and the mixture was stirred for 6 h at room temperature. The reaction is monitored by TLC. After completion of the reaction, the reaction mixture is concentrated at 40° C. and diluted with EA and washed with water and brine solution. Organic layer was dried over anhydrous $Na_2SO_4$ and filtered and the solvent was evaporated to give crude compound WGint6. LC/MS (ESI) m/z: $[M+H]^+$ 1360.

Example 4 Synthesis of Compound WGint7

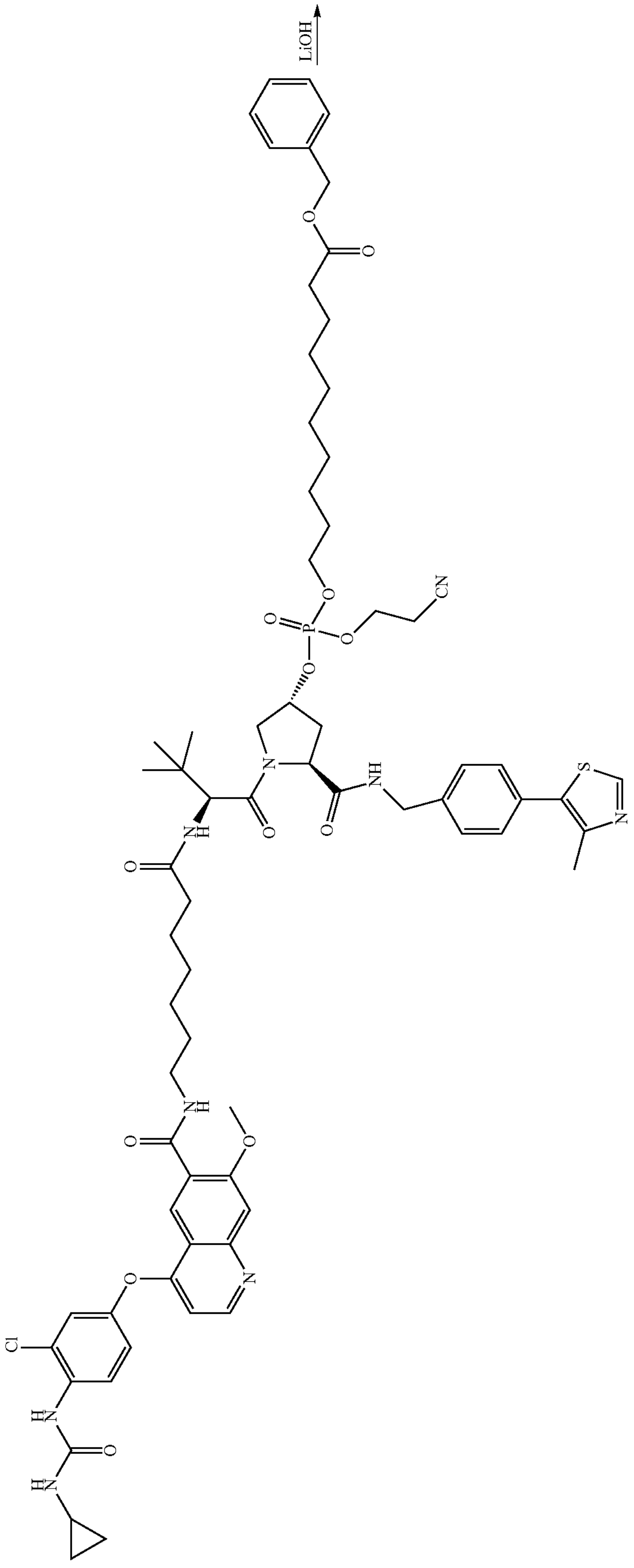
WGint6

-continued
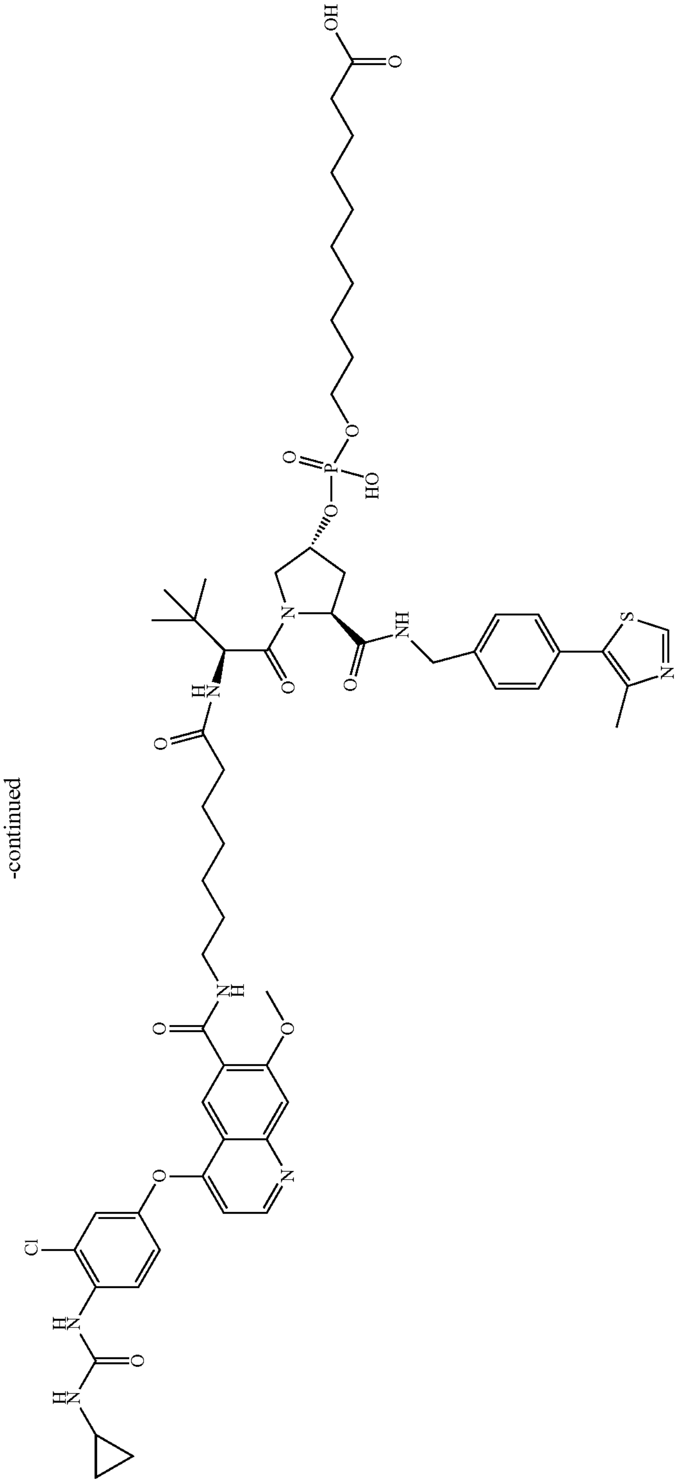
WGint7

The crude compound WGint6 from above step was dissolved in THF (8 mL). Then 0.5 M LiOH (8 mL) was added. The mixture was stirred for 6 h at room temperature and evaporated to give crude which was purified with prep-HPLC to give compound WGint7 (85 mg). LC/MS (ESI) m/z: $[M+H]^+$ 1218.

Example 5 Synthesis of Compound WGint9

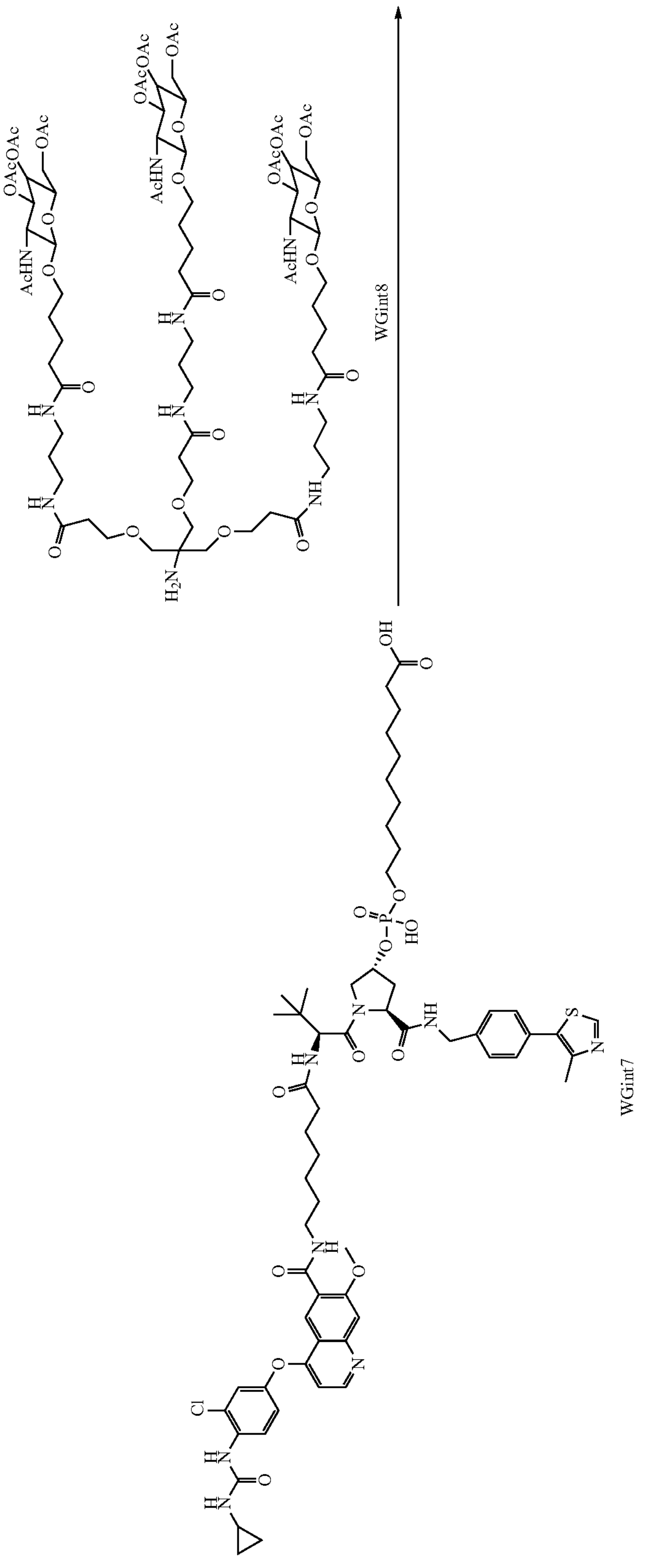
WGint7
WGint8

-continued
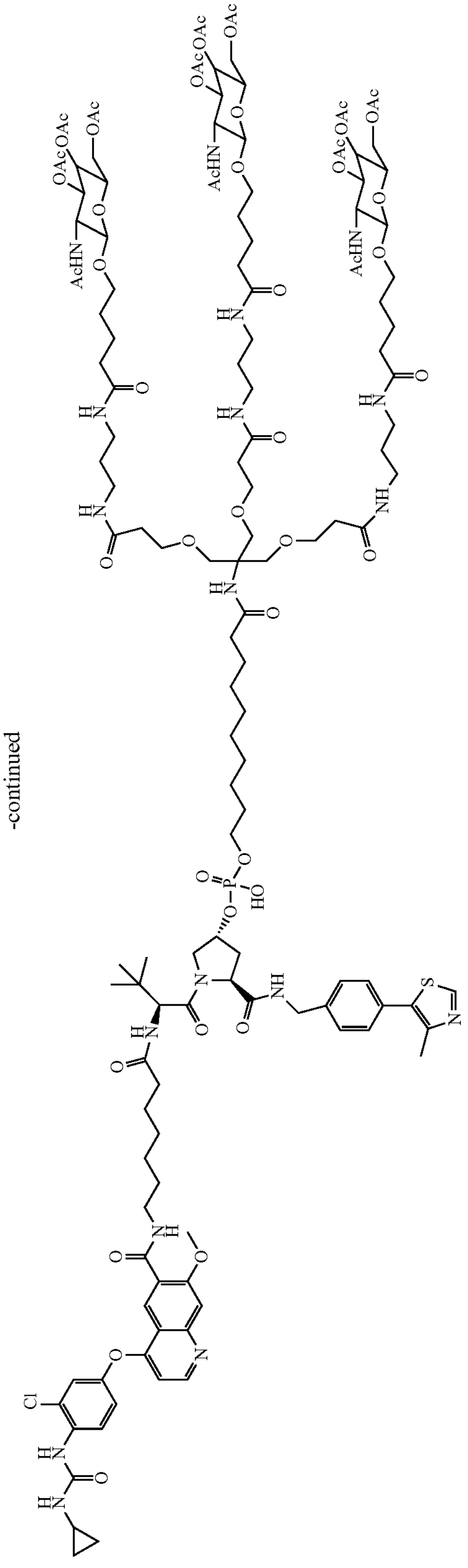
WGint9

To a solution of compound WGint7 (40 mg, 0.033 mmol) in DMF (1 mL) were added HBTU (13.8 mg, 0.036 mmol) and DIEA (4.7 mg, 0.036 mmol), and the resulting mixture was stirred for few minutes. A solution of compound WGint8 (40 mg, 0.022 mmol) in DMF (0.5 mL) was added and stirred at room temperature overnight. Solvents and volatiles were removed under reduced pressure, and the residue was purified with prep-HPLC to give compound WGint9 (8 mg). LC/MS (ESI) m/z: $[M+H]^+$ 2993.

Example 6 Synthesis of Compound WG-1 (00300639)

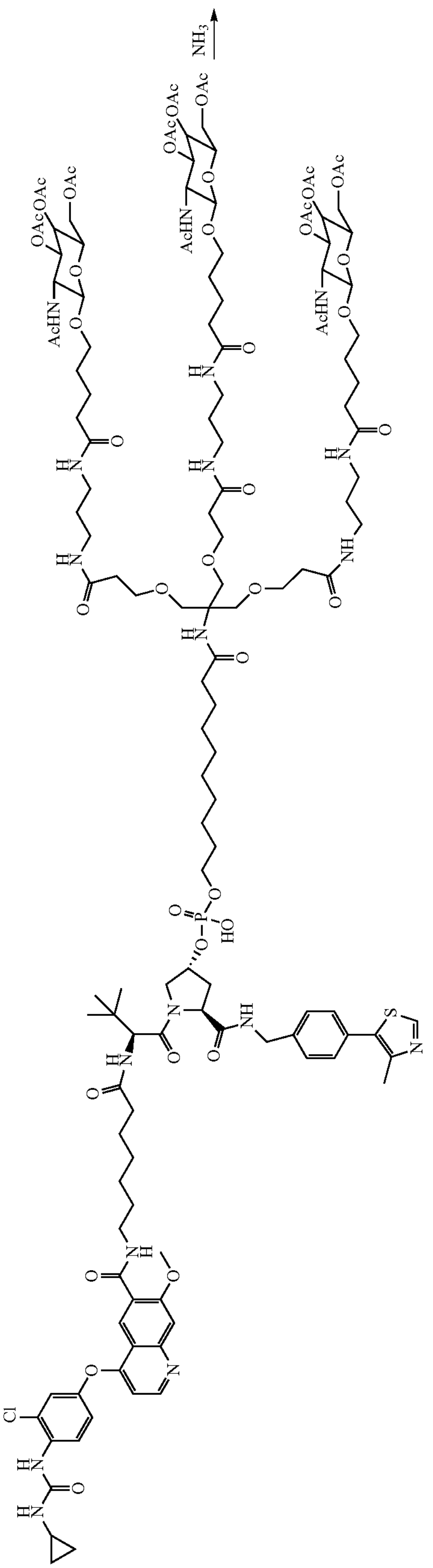
WGint9

-continued
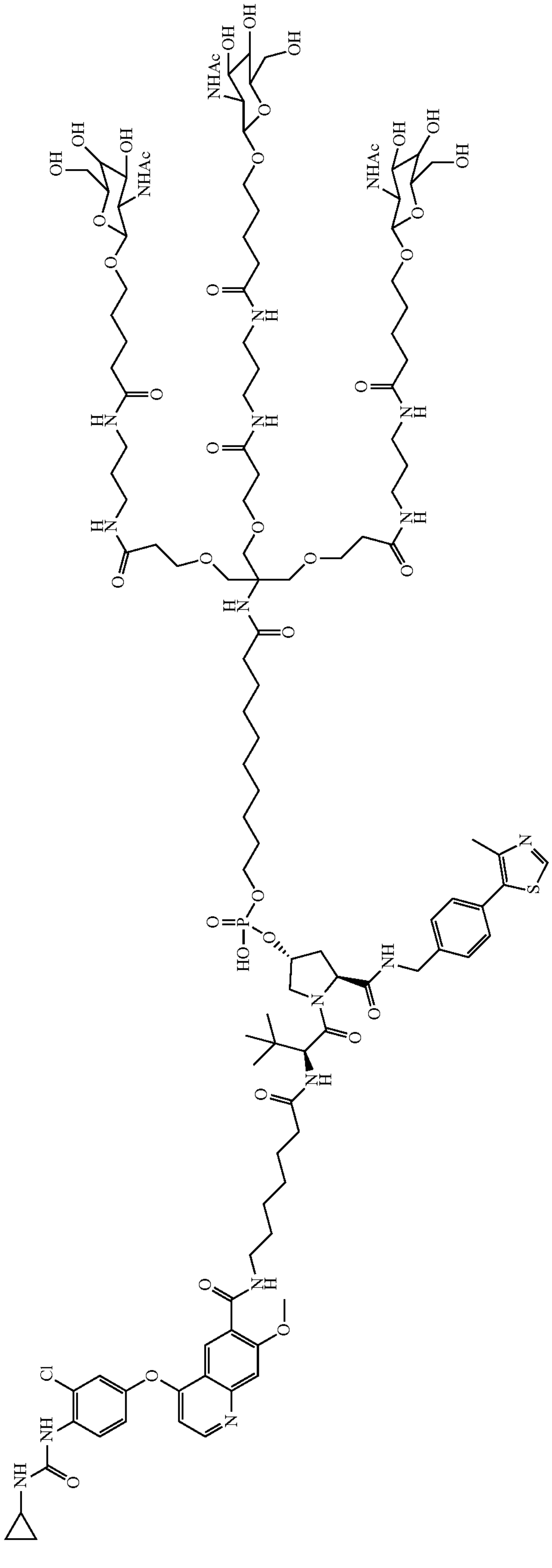
WG-1(00300639)

A solution of compound WGint9 (8 mg) in MeOH (0.5 mL) was treated with 40% $NH_3 \cdot H_2O$ (0.5 mL) and stirred for 4 h at room temperature. The mixture was evaporated and poured into water and DCM, and organic layer was evaporated to give the compound WG-1(00300639) (6 mg). LC/MS (ESI) m/z: $[M+H]^+$:2614, [M/2+1]+:1308; $^1$HNMR ($CD_3OD$, 400 MHZ): δ 8.887 (s, 1H), 8.779 (s, 1H), 8.638-8.651 (d, J=5.2 Hz, 1H), 8.206-8.228 (d, J=8.8 Hz, 1H), 7.388-7.509 (m, 5H), 7.201-7.280 (m, 2H), 6.608-6.622 (d, J=5.6 Hz, 1H), 4.537-4.682 (m, 3H), 4.358-4.398 (t, J=16.0 Hz, 3H), 4.086-4.113 (t, J=10.8 Hz, 3H), 3.456-3.973 (m, 36H), 3.217-3.366 (m, 10H), 2.092-2.712 (m, 22H), 1.954-2.000 (m, 13H), 1.307-1.718 (m, 43H), 0.575-1.048 (m, 16H); $^{31}$PNMR ($CD_3OD$, 162 MHZ): δ 0.709 (P).

Example 7 Synthesis of Compound 003006int2

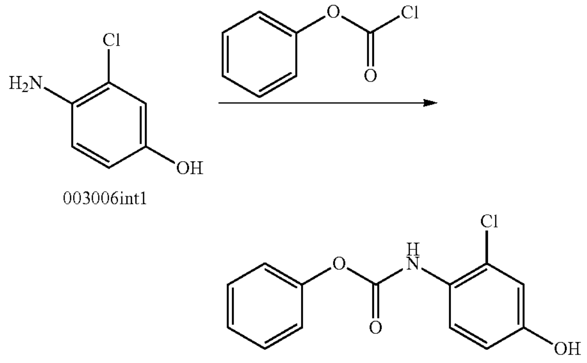

003006int1

003006int2

To a solution of compound 003006int1 (20 g, 0.14 mol) and Py (17 g, 0.2 mol) in DMF (200 mL) was added dropwise phenyl carbonochloridate (22 g, 0.14 mmol). The mixture was stirred overnight at 0° C. The above solution was poured into ice-water (500 mL) and extracted with EtOAc (200 mL×3). The combined organic layers were dried over $Na_2SO_4$ and concentrated to give compound 003006int2 (25 g, crude) as brown solid. LC/MS (ESI) m/z: $[M+H]^+$ 264.

Example 8 Synthesis of Compound 003006int3

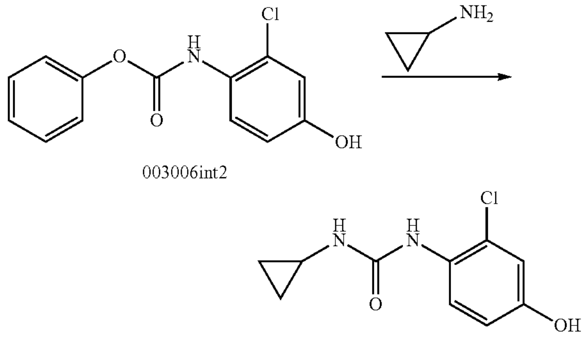

003006int2

003006int3

The solution of compound 003006int2 (25 g, 0.13 mmol), TEA (13 g, 0.13 mol) and cyclopropanamine (15 g, 0.26 mol) in DCM (300 mL) was stirred overnight at room temperature. The mixture washed with water and under reduced pressure to give compound 006003int3 (12 g, 57%) as brown solid. LC/MS (ESI) m/z: $[M+H]^+$ 227.

Example 9 Synthesis of Compound 003006int4

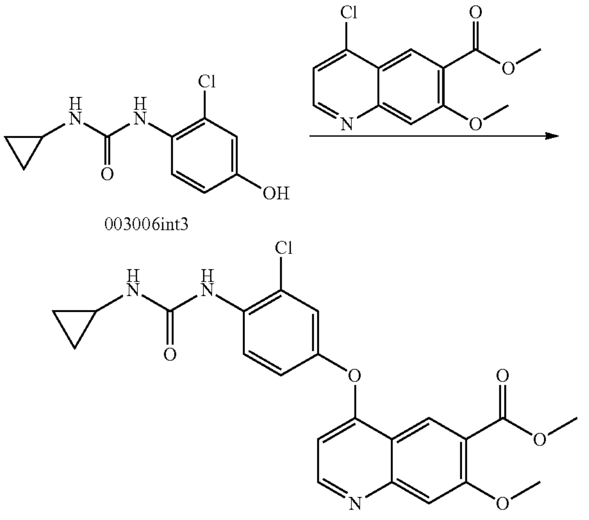

003006int3

003006int4

The solution of compound 003006int3 (12 g, 52.9 mmol), $K_2CO_3$ (13 g, 106 mmol) and methyl 4-chloro-7-methoxyquinoline-6-carboxylate (16 g, 63.5 mol) in DMF (120 mL) was stirred overnight at 80° C. The mixture was poured into ice-water and filtered, and the filter cake was washed with water and dried to give compound 003006int4 (14 g, 59.8%) as brown solid. LC/MS (ESI) m/z: $[M+H]^+$ 442.

Example 10 Synthesis of Compound 003006int5

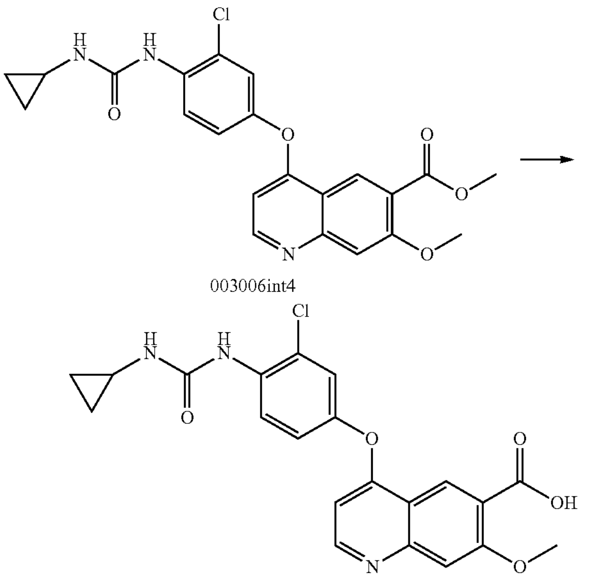

003006int4

003006int5

The solution of compound 003006int4 (14 g, 31.7 mmol) and LiOH (2.5 g, 63.4 mmol) in MeOH/$H_2O$ (140 mL) was stirred overnight at room temperature. The reaction solution was pH-adjusted to 2-3 by the addition of 1N hydrochloric acid and filtered to give compound 003006int5 (10 g, 73.5%) as yellow solid. LC/MS (ESI) m/z: $[M+H]^+$ 428.

Example 11 Synthesis of Compound 003006int6

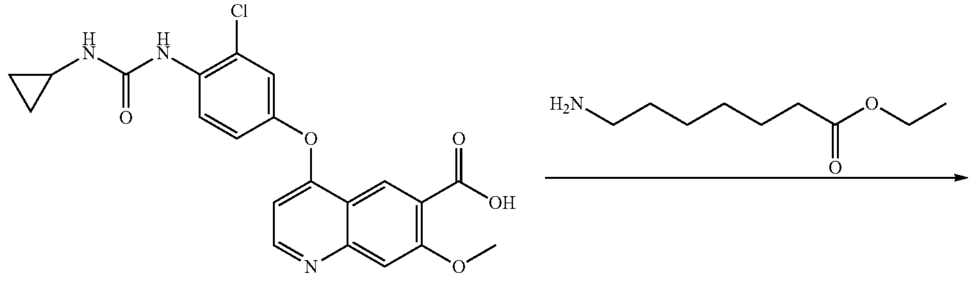

003006int5

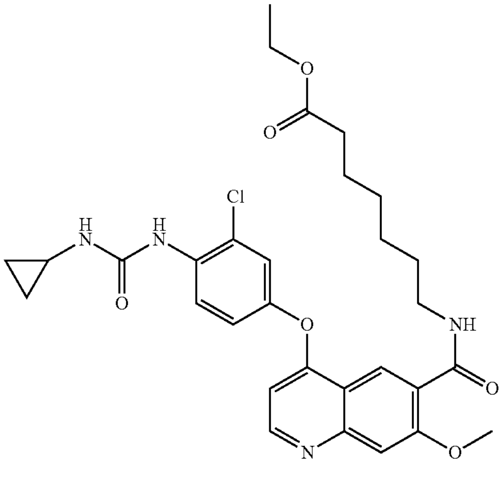

003006int6

To a solution of compound 003006int5 (1 g, 2.3 mmol) and ethyl 7-aminoheptanoate (485 mg, 2.8 mmol) in DCM (10 mL) was added reaction solution HOBT (474 mg, 3.5 mmol) EDCI (672 mg, 3.5 mmol) DIEA (755 mg, 5.8 mmol). The mixture was stirred overnight at room temperature. The reaction was extracted with DCM (10 mL×2). The combined organic layers were dried over $Na_2SO_4$ and concentrated to give the crude product which was purified by silica gel to give compound 003006int6 (700 mg, 51.5%) as yellow liquid. LC/MS (ESI) m/z: $[M+H]^+$ 583.

Example 12 Synthesis of Compound 003006int7

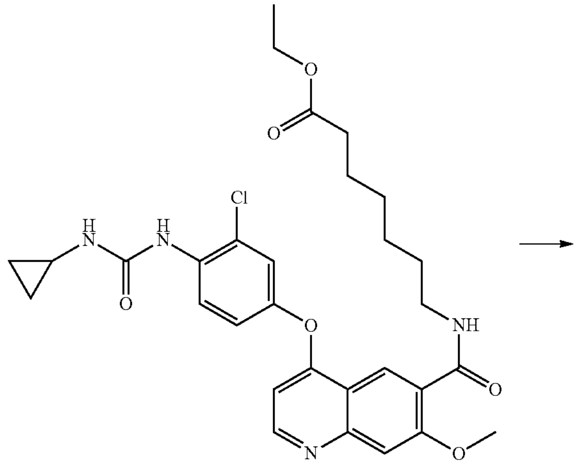

003006int6

-continued

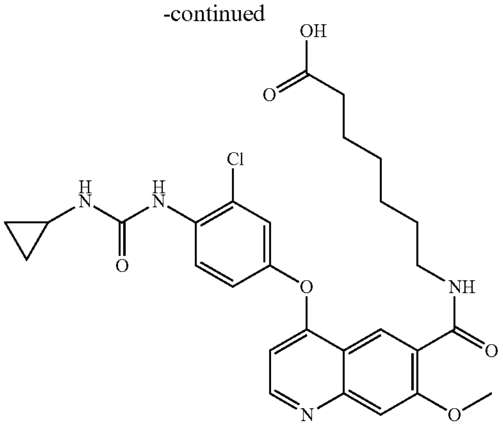

003006int7

The solution of compound 003006int6 (700 mg, 1.2 mmol) and LiOH (96 mg, 2.4 mmol) in $MeOH/H_2O$ (10 mL) was stirred for reaction overnight. The reaction solution was pH-adjusted to 2-3 by the addition of 1N hydrochloric acid and filtered to give compound 003006int7 (300 mg, 45%) as yellow solid. LC/MS (ESI) m/z: $[M+H]^+$ 555.

Example 13 Synthesis of Compound 003006

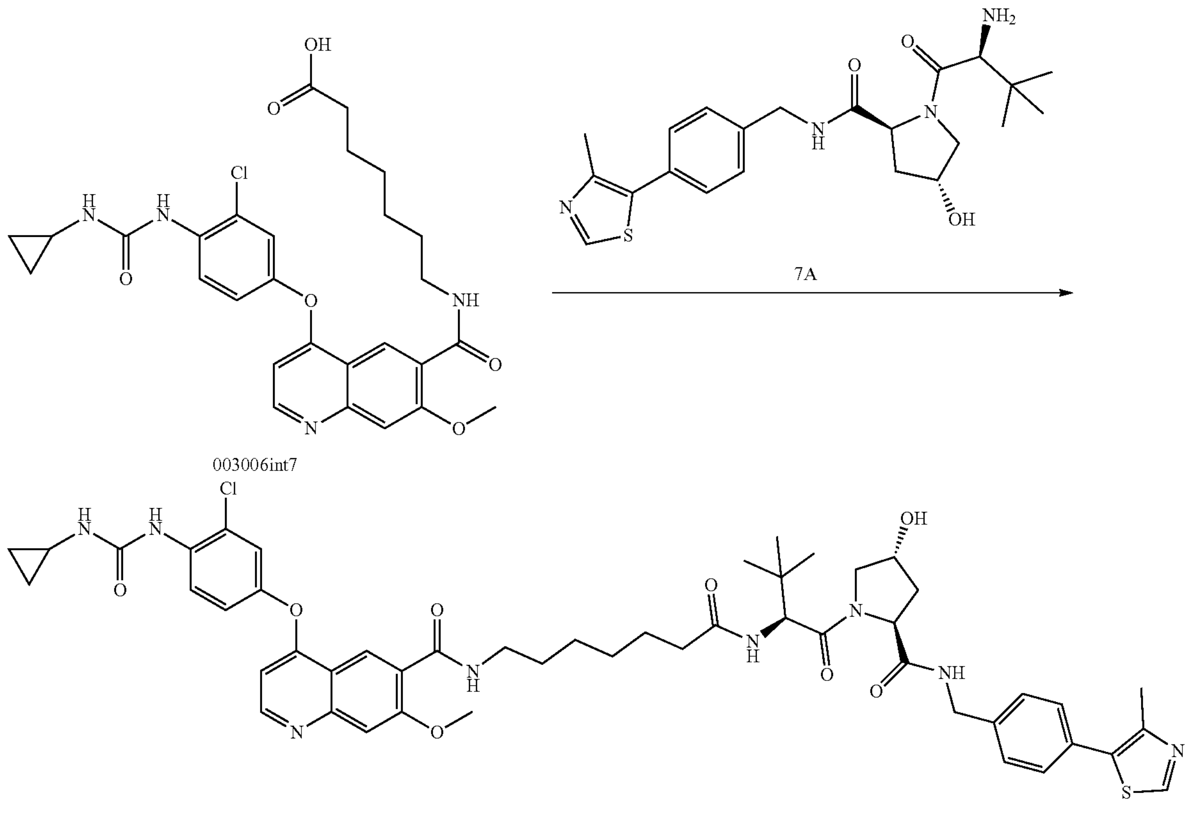

003006int7

7A

WGint4(003006)

To a solution of compound 003006int7 (300 mg, 0.54 mmol) and 7A (279 mg, 0.65 mmol) in DCM (5 mL) was added HOBT (110 mg, 0.81 mmol), EDCI (155 mg, 0.81 mmol) and DIEA (175 mg, 1.3 mmol). The mixture was stirred overnight for reaction. The reaction mixture was extracted with DCM (10 mL×2). The combined organic layers were dried over $Na_2SO_4$ and concentrated to give the crude product which was purified by prep-HPLC to give WGint4(003006) (120 mg, 22.9%) as white solid. LC/MS (ESI) m/z: $[M+H]^+$ 967.

Example 14 Synthesis of Compound 005000int2

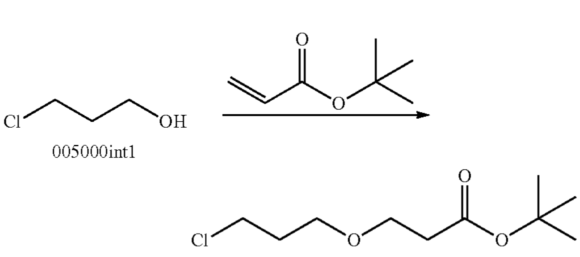

005000int1

005000int2

The solution of compound 005000int1 (10 g, 0.11 mol), tert-Butyl acrylate (18 g, 0.14 mol) and potassium tert-butoxide (0.16 g, 1.4 mmol) in THF (100 mL) was stirred overnight at room temperature. The mixture was quenched with 1N HCl (50 mL), and extracted with EA (50 mL*2). The combined organic layers were dried over $Na_2SO_4$ and concentrated to give the compound 005000int2 (20 g, 81.9%) without further purification. LC/MS (ESI) m/z: $[M+H]^+$ 223.

Example 15 Synthesis of Compound 005000int3

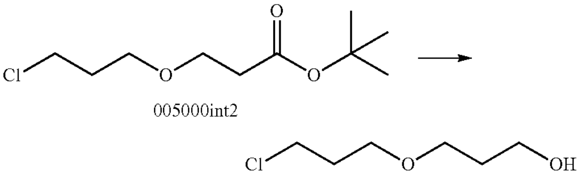

005000int2

005000int3

To a solution of compound 005000int2 (10 g, 0.045 mol) in THF (100 mL) was added edLAH (2.6 g, 0.068 mol) in three portions at 0° C. The mixture was stirred at room temperature for 3 hours. The reaction was quenched with $Na_2SO_4 \cdot 10H_2O$. The mixture was filtered and the filtrate was evaporated to give compound 005000int3 (6 g, 88.2%). LC/MS (ESI) m/z: $[M+H]^+$ 153.

Example 16 Synthesis of Compound 005000int4

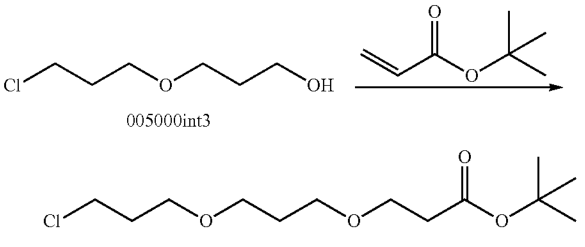

005000int3

005000int4

The solution of compound 005000int3 (6 g, 0.039 mol), tert-Butyl acrylate (6.6 g, 0.052 mol) and potassium tert-butoxide (0.22 g, 0.002 mol) in THF (100 mL) was stirred overnight. The mixture was quenched with 1N HCl (50 mL), and extracted with EA (30 mL*2). The combined organic layers were dried over $Na_2SO_4$ and concentrated to give the compound 005000int4 (10 g, 90.7%) without further purification. LC/MS (ESI) m/z: $[M+H]^+$ 281.

Example 17 Synthesis of Compound Side 1

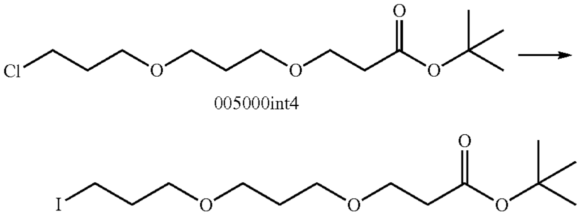

005000int4 side 1

Compound 005000int4 (5 g, 0.018 mmol) and sodium iodide (13.5 g, 0.09 mol) in acetone (50 mL) was stirred at 50° ° C. for 48 hours. After cooling, solvent were evaporated in vacuum and washed with water (20 mL*2) to obtain side 1 (5 g, 74.9%). LC/MS (ESI) m/z: $[M+H]^+$ 373.

Example 18 Synthesis of Compound 005000int8

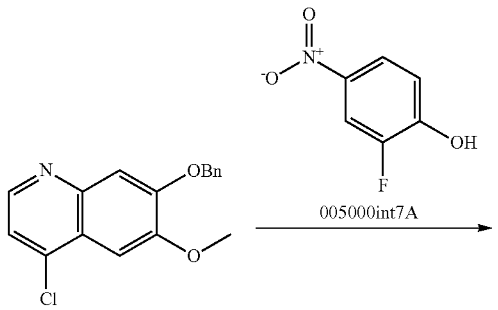

005000int7A

005000int7

-continued

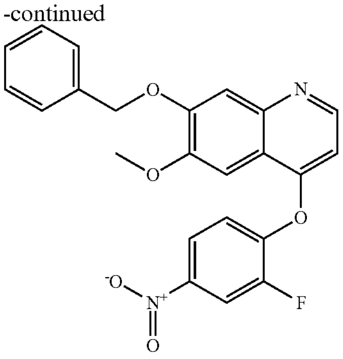

005000int8

The solution of compound 005000int7 (10 g, 0.033 mol), 7A (5.6 g, 0.037 mol) and DIEA (0.28 g, 0.01 mol) in NMP (100 mL) was stirred overnight at 130° ° C. The mixture was purified by prep-HPLC to give compound 005000int8 (5 g, 35.7%). LC/MS (ESI) m/z: $[M+H]^+$ 421.

Example 19 Synthesis of Compound 005000int9

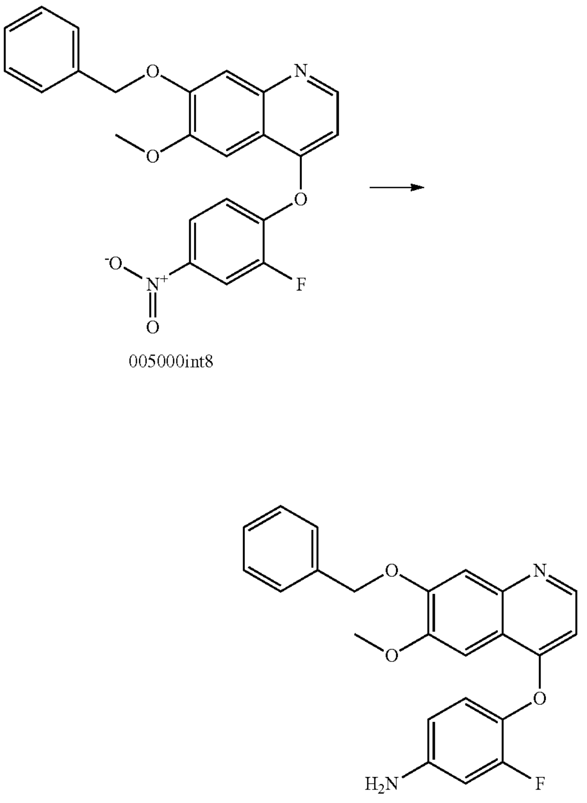

005000int8

005000int9

To a solution of compound 005000int8 (4 g, 9.5 mmol) and $NH_4Cl$ (10 g, 0.19 mol) in EtOH (20 mL) and $H_2O$ (20 mL) was added Zn (10 g, 0.15 mol). The mixture was stirred at 80° C. for 2 hours. The reaction was filtered and evaporated, and the residue was purified by silica gel to give compound 005000int9 (3.2 g, 86.5%). LC/MS (ESI) m/z: $[M+H]^+$ 391.

Example 20 Synthesis of Compound 005000int10

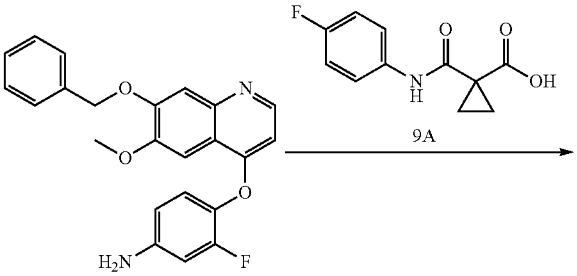

005000int9

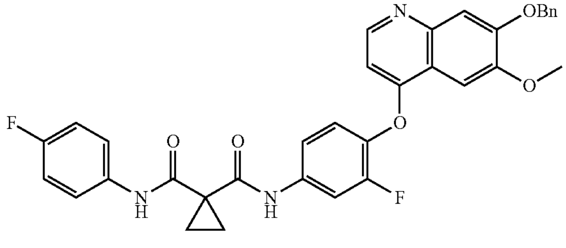

005000int10

To a solution of compound 005000int9 (3.9 g, 10 mmol), compound 9A (2.7 g, 12 mmol) and TEA (1.5 g, 15 mmol) in DMF (40 mL) was added HOBT (2 g, 15 mmol) and EDCI (573 mg, 3 mmol). The mixture was stirred at room temperature overnight. The reaction was quenched with $Na_2CO_3$ aqueous, and extracted with EA. The combined organic layers was evaporated and purified by silica gel to give compound 005000int10 (3 g, 50.4%). LC/MS (ESI) m/z: $[M+H]^+$ 596.

Example 21 Synthesis of Compound Core 1

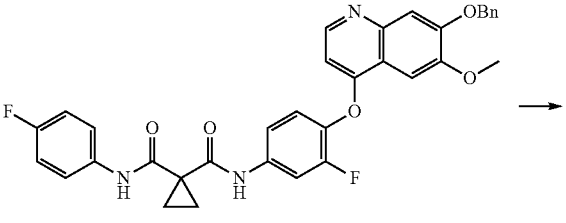

005000int10

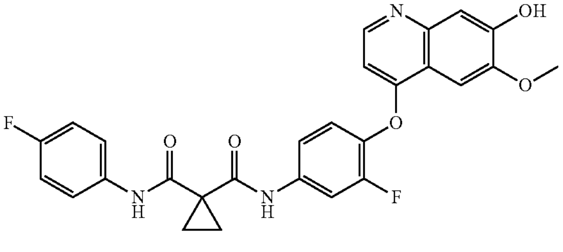

Core 1

The solution of compound 005000int10 (1.5 g, 7.2 mmol) and Pd/C (200 mg) in MeOH (20 mL) was stirred at room temperature overnight under $H_2$ balloon. The reaction was filtered and evaporated to give Core 1 (1 g, 78.7%). LC/MS (ESI) m/z: $[M+H]^+$ 506.

Example 22 Synthesis of Compound 006000 int11

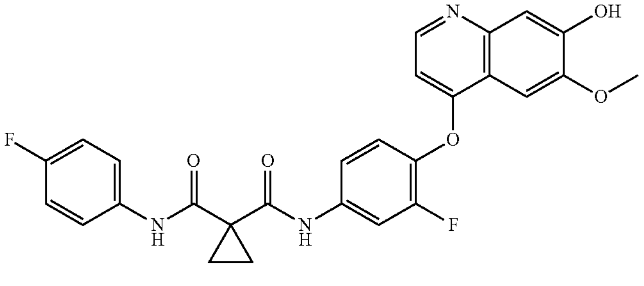

Core 1

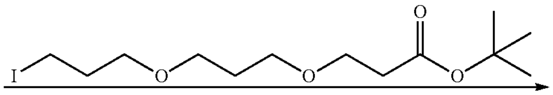

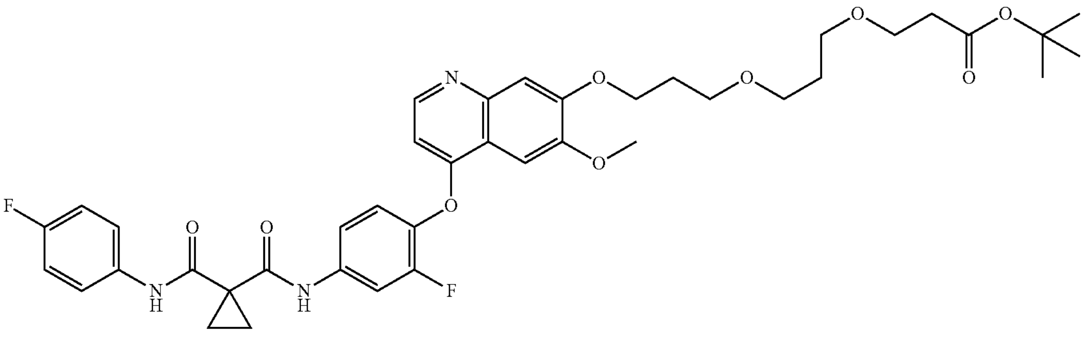

006000int11

The solution of core 1 (500 mg, 0.99 mmol), side 1 (447 mg, 1.28 mmol) and cesium carbonate (980 mg, 3 mmol) in DMF (5 mL) was stirred at 30° C. overnight. The reaction was poured into water and extracted with EA (10 mL×2). The combined organic layers were dried over $Na_2SO_4$ and concentrated to give the crude product which was purified by silica gel to give compound 006000int11 (350 mg, 47.2%) as white solid. LC/MS (ESI) m/z: $[M+H]^+$ 750.

Example 23 Synthesis of Compound 006000 int12

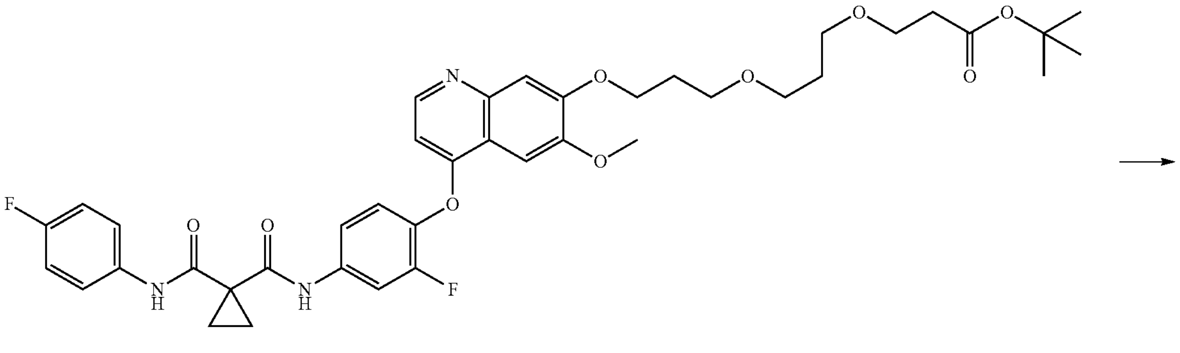

006000int11

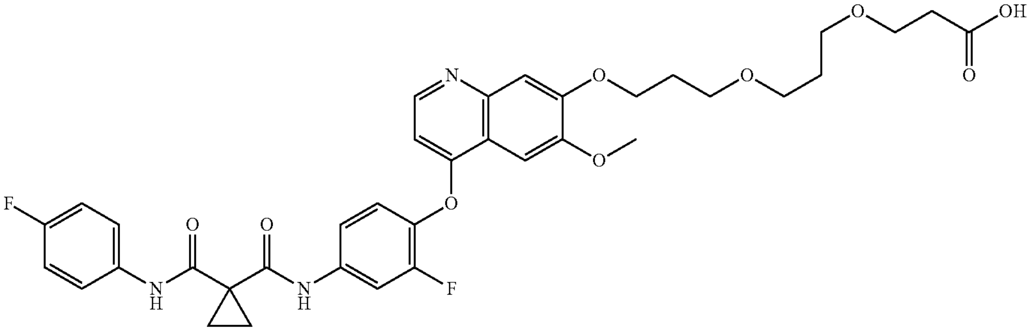

006000int12

To a solution of compound 006000int11 (300 mg, 0.4 mmol) was added TFA (0.3 mL). The mixture was stirred at room temperature overnight. The solvent was evaporated to give compound 006000int12 (200 mg, 72.2%). LC/MS (ESI) m/z: $[M+H]^+$ 694.

Example 24 Synthesis of Compound WGint4 (006000)

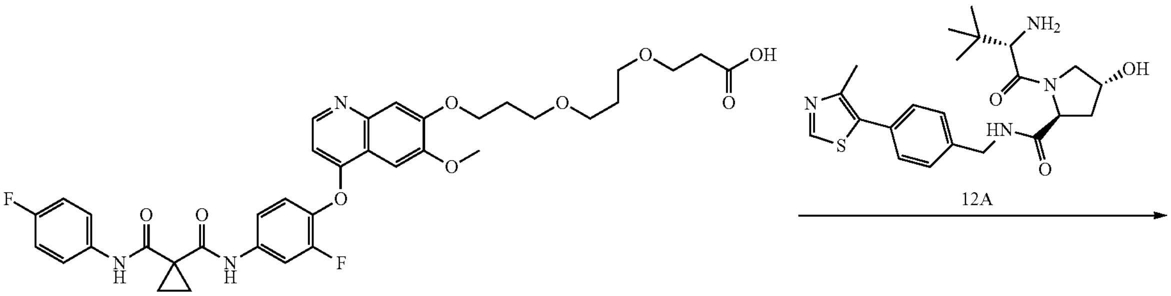

006000int12

-continued

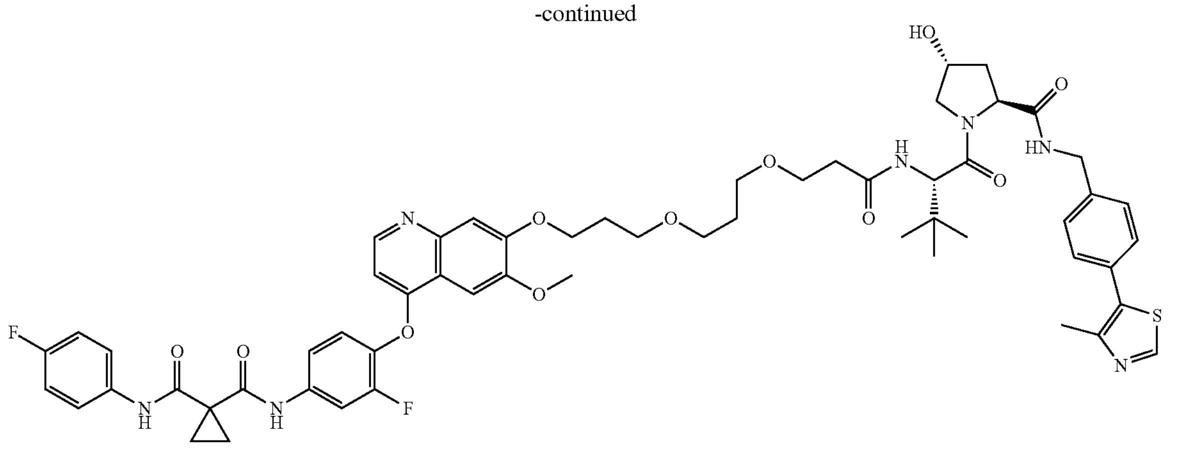

006000

To a solution of compound 006000int12 (100 mg, 0.14 mmol) and 12A (75 mg, 0.17 mmol) in DCM (1 mL) was added HOBT (30 mg, 0.22 mmol), EDCI (43 mg, 0.22 mmol) and DIEA (65 mg, 0.5 mmol). The mixture was stirred overnight at room temperature. The reaction mixture was added into water and extracted with DCM (10 mL×2). The combined organic layers were dried over $Na_2SO_4$ and concentrated to give the crude product which was purified by prep-HPLC to give WGint4(006000) (20 mg, 13%) as white solid. LC/MS (ESI) m/z: $[M+H]^+$ 1106.

Example 25 Synthesis of Compound 005000int13

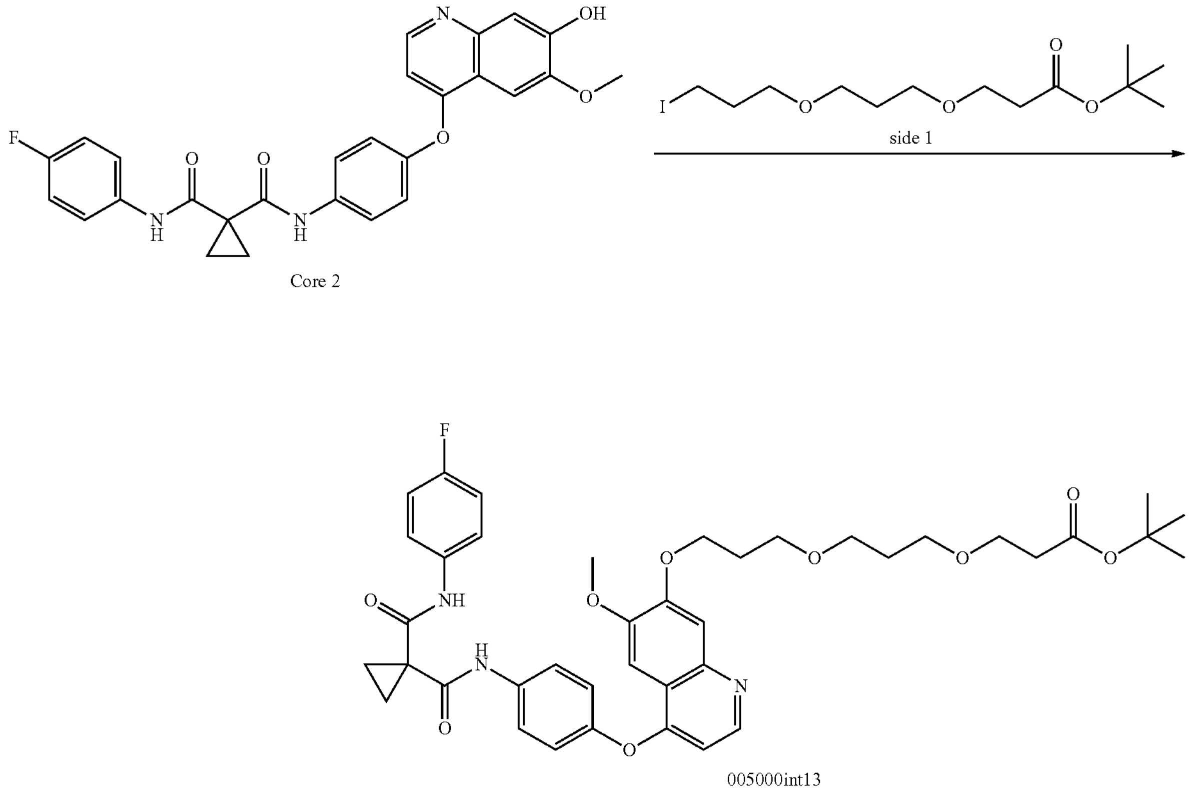

Core 2

005000int13

The solution of core 2 (600 mg, 1.23 mmol), side 1 (584 mg, 1.57 mmol) and cesium carbonate (980 mg, 3 mmol) in DMF (5 mL) was stirred at 30° ° C. overnight. The reaction solution was poured into water and extracted with EA (10 mL×2). The combined organic layers were dried over $Na_2SO_4$ and concentrated to give the crude product which was purified by silica gel to give compound 005000int13 (200 mg, 22.2%) as white solid. LC/MS (ESI) m/z: $[M+H]^+$ 732.

Example 26 Synthesis of Compound 005000int14

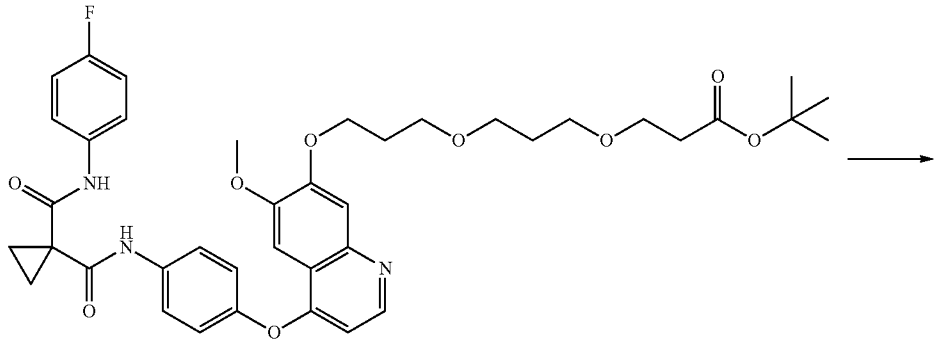

005000int13

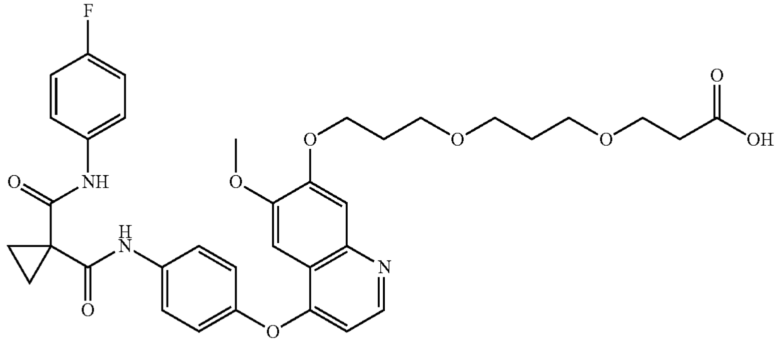

005000int14

To a solution of compound 005000int13 (300 mg, 0.4 mmol) was added TFA (0.3 mL). The mixture was stirred at room temperature overnight. The solvent was evaporated to give compound 005000int14 (200 mg, 72.2%). LC/MS (ESI) m/z: $[M+H]^+$ 676.

Example 27 Synthesis of Compound WGint4 (005000)

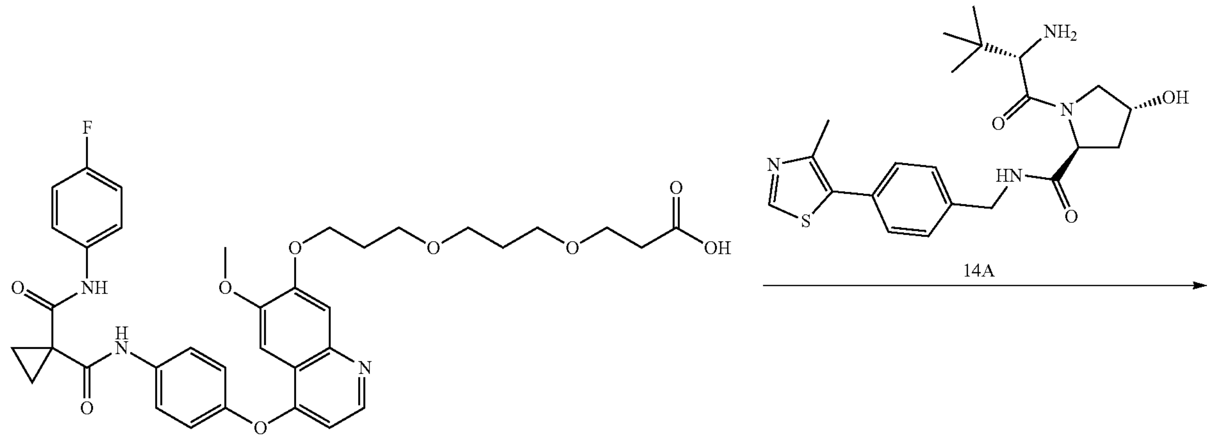

005000int14

-continued

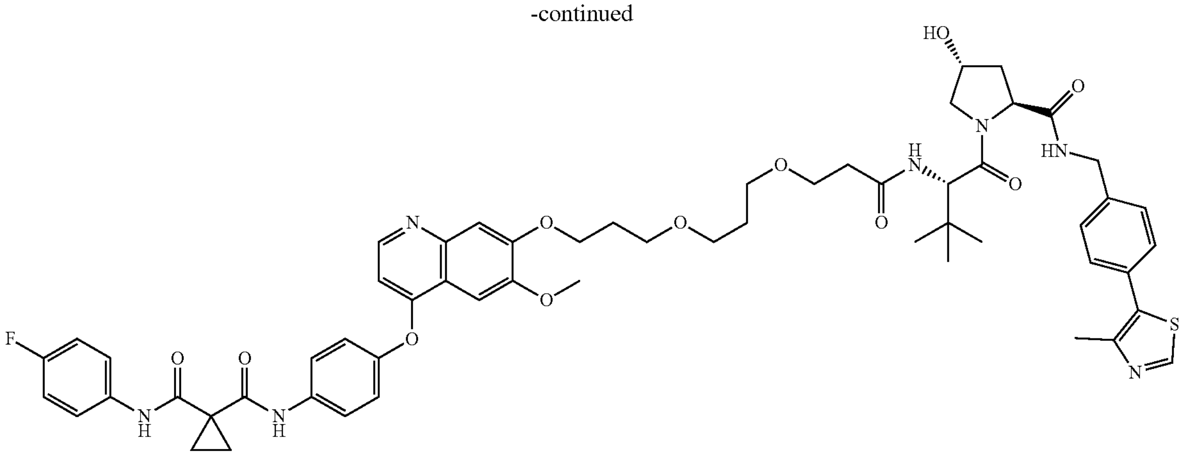

WGint4(005000)

To a solution of compound 005000int14 (100 mg, 0.14 mmol) and 14A (75 mg, 0.17 mmol) in DCM (1 mL) was added HOBT (30 mg, 0.22 mmol), EDCI (43 mg, 0.22 mmol) and DIEA (65 mg, 0.5 mmol). The mixture was stirred overnight at room temperature. The reaction mixture was added into water and extracted with DCM (10 mL×2). The combined organic layers were dried over $Na_2SO_4$ and concentrated to give the crude product which was purified by prep-HPLC to give WGint4(005000) (16 mg, 8%) as white solid. LC/MS (ESI) m/z: $[M+H]^+$ 1088.

Example 28 Synthesis of Compounds WG-2-WG-25

Furthermore, compounds WG-2-WG-25 were synthesized with the identical or similar methods described in the examples 1-27. The structures were confirmed with LC/MS and the data were shown in the following table:

TABLE 1

Structural confirmation data of compounds WG-2-WG-25

| Compound | LC/MS (ESI) $[M + H]^+$ | Theoretical value of HRMS $[M + H]^+$ | Measured values of HRMS $[M + H]^+$ |
|---|---|---|---|
| WG-2 | 1950 | 1950.9023 | 1950.9006 |
| WG-3 | 2614 | 2614.2350 | 2614.2379 |
| WG-4 | 2736 | 2735.3010 | 2735.3002 |
| WG-5 | 2753 | 2753.2915 | 2753.2896 |
| WG-6 | 2646 | 2646.2748 | 2646.2712 |
| WG-7 | 2760 | 2760.3326 | 2760.3370 |
| WG-8 | 2736 | 2735.3010 | 2735.2995 |
| WG-9 | 2838 | 2838.3769 | 2838.3801 |
| WG-10 | 2760 | 2759.3486 | 2759.3511 |
| WG-11 | 2800 | 2799.3799 | 2799.3810 |
| WG-12 | 2799 | 2799.3799 | 2799.3805 |
| WG-13 | 2723 | 2723.2489 | 2723.2527 |
| WG-14 | 2722 | 2722.2649 | 2722.2673 |
| WG-15 | 2756 | 2756.3125 | 2756.3158 |
| WG-16 | 2617 | 2617.2692 | 2617.2716 |
| WG-17 | 2582 | 2581.2146 | 2581.2190 |
| WG-18 | 2630 | 2629.1973 | 2629.2004 |
| WG-19 | 2740 | 2739.2998 | 2739.3017 |
| WG-20 | 2620 | 2619.2074 | 2619.2115 |
| WG-21 | 2760 | 2760.2832 | 2760.2773 |

TABLE 1-continued

Structural confirmation data of compounds WG-2-WG-25

| Compound | LC/MS (ESI) $[M + H]^+$ | Theoretical value of HRMS $[M + H]^+$ | Measured values of HRMS $[M + H]^+$ |
|---|---|---|---|
| WG-22 | 2509 | 2509.1616 | 2509.1587 |
| WG-23 | 2744 | 2743.3007 | 2743.2992 |
| WG-24 | 2692 | 2692.3125 | 2692.3083 |
| WG-25 | 2624 | 2623.3074 | 2623.3112 |

Example 29 Solubility Test

Series solutions of 1 nM/10 nM/100 nM/100 nM/1 uM/10 uM/100 uM/1 mM were prepared according to following steps: WG compounds to be tested in the present application and corresponding compounds of structure A were respectively weighed, dissolved in deionized water, and oscillated at 37° C. for 12 hours to reach dissolution equilibrium. The resulted solutions were filtered 3 times with a filter membrane, and filtrates were collected. Actual concentrations of the compounds in the solutions were determined with HPLC. A curve of actual concentration of the solution—planned concentration of the solution was drawn, and the turning point of the curve indicated the equilibrium concentration of the compounds.

Example 30 Transmembrane Test

Liver cancer cells (HUH-7) were seeded in a 6-well plate at a concentration of $4*10^5$ cells/mL, 2 mL per well, and cultured overnight until the cells were adherent to the wall.

The next day, compound solutions were prepared as follows: WG compounds of present application and corresponding compounds of structure A were respectively weighed, prepared with pure DMSO into mother solutions of high concentration, then gradiently diluted to obtain compound solutions of 10 uM/30 uM/100 uM/150 uM/300 uM in 10% DMSO, and shaken to mix well.

When the cells were adherent to the wall under microscope observation, 200 uL of compound solutions were added to each well with a ratio of compound solution to culture medium at 1:10.

After culture for 24 hours, the culture medium was sucked out with a pipette, and the wells were then washed five times with phosphate buffer, 2 mL each time for 30 seconds, to ensure there were no compound residues in the environment of the cells. Solutions in the wells were thoroughly sucked up, and 150 uL RIPA Lysis Buffer was added into each well. Then the culture was continued on ice for 30 min to lyse the cells. Lysates were collected and centrifuged at 100000 rpm for 1 h, and supernatants were collected and characterized with HPLC to determine the concentration of the compounds therein.

The solubility and changes of transmembrane efficiency of WG compounds relative to corresponding compounds of structure A were analyzed and calculated. An arithmetic mean value of transmembrane efficiency changes under different concentrations was calculated, thereby obtaining a reference value of the difference of transmembrane efficiency between two groups of compounds.

Example 31 Cell Growth Inhibition Test

Liver cancer cells (HUH-7) were seeded in a 96-well plate at a concentration of $2*10^4$ cells/mL, 100 uL per well, and cultured overnight.

The next day, the cells were observed microscope to ensure adherence. Compound solutions were prepared as follows: WG compounds of present application and corresponding compounds of structure A were respectively weighed, prepared with pure DMSO into mother solutions of high concentration, then gradiently diluted to obtain compound solutions of 10 nM/100 nM/300 nM/1000 nM/3000 nM in 10% DMSO, and shaken to mix well.

Positive drug solutions in the control group were prepared with the same solvent and method, and only a single dosage was required. In this test, the positive drug solution is 1 uM lenvatinib.

After solution preparation was completed, 10 uL of compound solutions were added into each well of the 96-well plate, three duplicates for each dosage. The plate was gently shaken to allow the cells to repeatedly contact with the compound solutions, and then the plate was placed in an incubator to culture for 72 hours. 72 hours later, the plate was taken out and 10 uL cck-8 reagent was added into each well and shaken gently to mix well. Then the plate was placed in an incubator to culture for two hours. Two hours later, the plate was taken out and analyzed with a microplate reader to measure the absorbance of each well at a wavelength of 450 nm. The inhibition ability of the compounds on the growth of liver cancer cells at the current dosages and time can be calculated according to the formula as below:

Cell growth inhibition rate=[1−(absorbance of experimental group−absorbance of culture medium control group)/(absorbance of blank control group−absorbance of culture medium control group)]×100%.

A graph can be drawn according to the gradient of concentrations, and the results can be compared directly.

Example 32 Proteolysis Test

Liver cancer cells (HUH-7) were seeded in a 6-well plate at a concentration of $4*10^5$ cells/mL, 2 mL per well, and cultured overnight until the cells were adherent to the wall.

The next day, compound solutions were prepared as follows: WG compounds of present application and corresponding compounds of structure A were respectively weighed, prepared with pure DMSO into mother solutions of high concentration, then gradiently diluted to obtain compound solutions of 10 nM/30 nM/100 nM/300 nM/1000 nM/3000 nM in 10% DMSO, and shaken to mix well. 200 uL of compound solutions were added to each well with a ratio of compound solution to culture medium at 1:10.

After culture for 24 hours, the culture medium was sucked out with a pipette, and then the wells were washed 3 times with PBS. Solutions in the wells were thoroughly sucked up, and 150 uL RIPA Lysis Buffer was added into each well. Then the culture was continued on ice for 30 min to lyse the cells.

Lysates were collected and centrifuged at 16000 rpm for 10 minutes. Supernatants were collected and the total protein content was normalized with a BCA kit to determine target protein contents with Western blot.

The results were analyzed with ImageJ. Blackness of each strip was measured and the protein was quantified for comparison analysis according to formula: Protein content=blackness value of the experimental group/blackness value of the blank control group.

Comparative tests of five compounds were carried out according to the method of Example 29 to Example 32:

WGint4 (003006)/WG-1 (00300639) were discussed as an example, where WGint4 (003006) was the compound of structure A corresponding to WG-1 (00300639).

(1) Solubility (Equilibrium Solubility)

The solubility was 31 uM for WGint4 (003006) and 677 uM for WG-1 (00300639), indicating the solubility was increased by about 22 times.

(2) Transmembrane Efficiency

Figure 5:
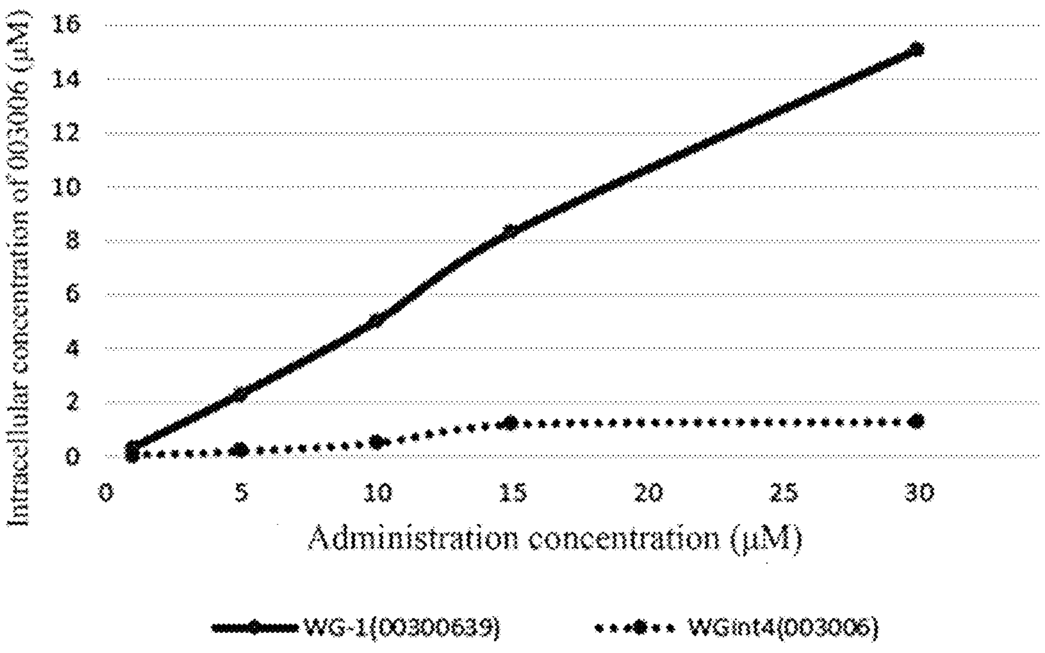
FIG. 5 shows transmembrane test results of WG-1 (00300639) and WGint4 (003006)

Data in FIG. 5 showed that the transmembrane efficiency of WG-1 (00300639) was about 9.2 times that of WGint4 (003006).

(3) Inhibition Effect on Cancer Cell Growth

Figure 6:
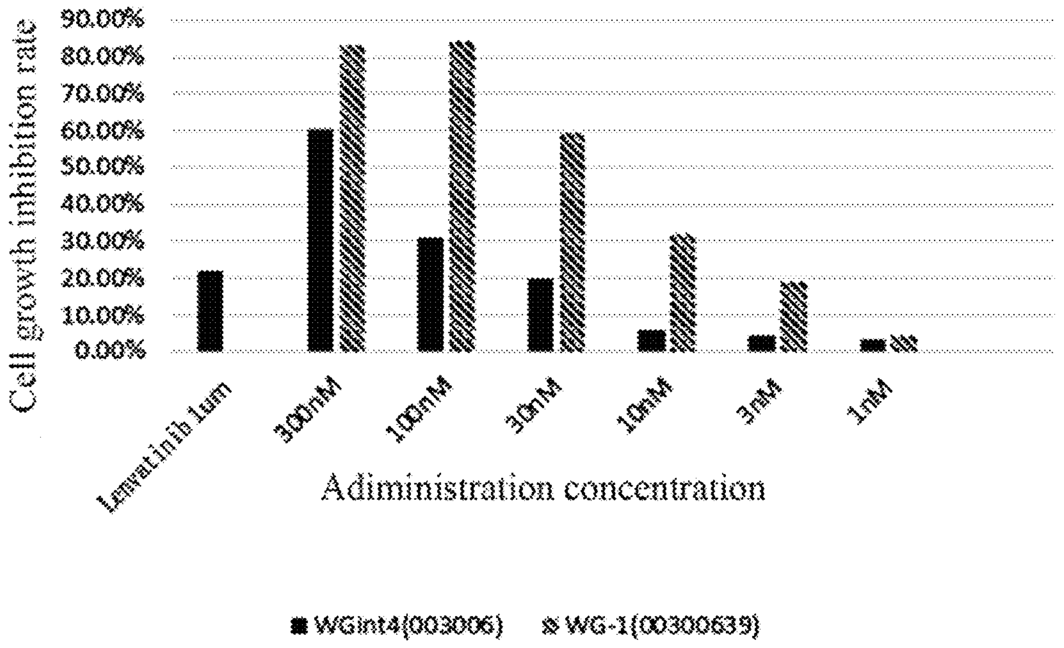
FIG. 6 shows growth inhibition test results on cancer cells by WG-1 (00300639), WGint4 (003006) and positive drug lenvatinib.

FIG. 6 showed that WG-1 (00300639) inhibited the growth of liver cancer cells significantly stronger than WGint4 (003006). It was calculated that the IC50 was 21.3 nM for WG-1 (00300639) and 210.7 nM for WGint4 (003006).

(4) Proteolysis

Figure 7:
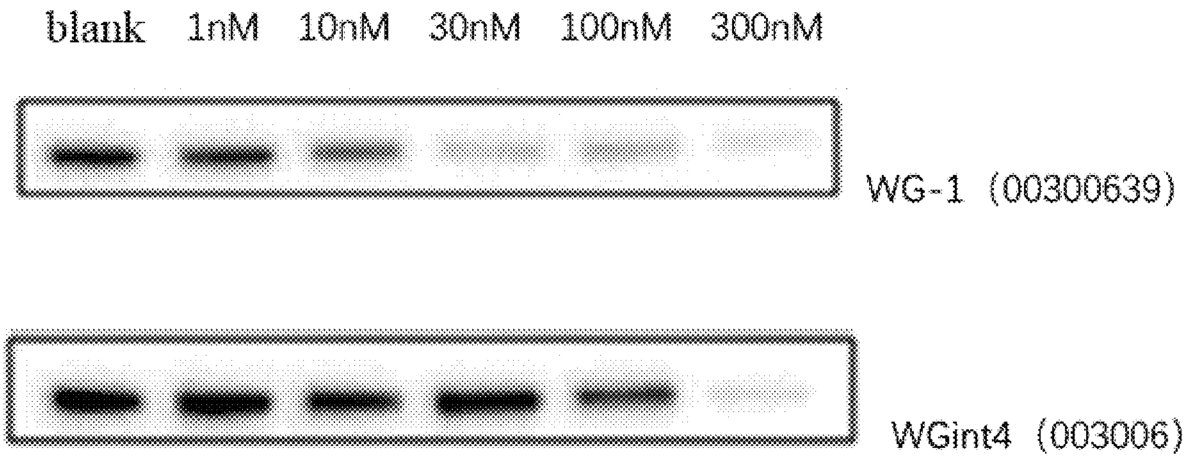
FIG. 7 shows proteolysis test results of WG-1 (00300639) and WGint4 (003006).

The results were shown in FIG. 7, and the test values were shown in the following table:

| | Dosage | | | | | |
|---|---|---|---|---|---|---|
| Compounds | Blank | 1 nM | 10 nM | 30 nM | 100 nM | 300 nM |
| WGint4(003006) | 1 | 0.97 | 0.97 | 0.84 | 0.65 | 0.22 |
| WG-1(00300639) | 1 | 0.93 | 0.72 | 0.31 | 0.16 | 0.13 |

It was calculated that WG-1 (00300639) DC50=18.0 nM, and WGint4 (003006) DC50=150.2 nM.

Data for Other Compounds were Listed as Follows:

| | Effects | | | |
|---|---|---|---|---|
| Compounds | Solubility | Transmembrane efficiency | Inhibition on cell growth | Proteolysis |
| WGint4(003006) | 31 uM | WG-2 is about 8.3 times higher than 003006 | IC50 = 210.7 nM | DC50 = 150.2 nM |
| WG-2(00300629) | 603 uM | | IC50 = 29.5 nM | DC50 = 21.4 nM |

-continued

| | Effects | | | |
|---|---|---|---|---|
| Compounds | Solubility | Transmembrane efficiency | Inhibition on cell growth | Proteolysis |
| WGint4(004006) | 19 uM | WG-3 is about 15 | IC50 = 568.0 nM | DC50 = 788.4M |
| WG-3(00400639) | 255 uM | times higher than 004006 | IC50 = 79.9 nM | DC50 = 81.4 nM |
| WGint4(005006) | 23 uM | WG-4 is about 17.1 | IC50 = 255.8 nM | DC50 = 219.1 nM |
| WG-4(00500639) | 476 uM | times higher than 005006 | IC50 = 15 nM | DC50 = 38.1 nM |
| WGint4(006006) | 40 uM | WG-5 is about 11.5 | IC50 = 410.1 nM | DC50 = 366.2 nM |
| WG-5(00600639) | 731 uM | times higher than 006006 | IC50 = 35.3 nM | DC50 = 12.0 nM |

It should be understood that the above examples and technical solutions are only for exemplary illustrations of the present invention, rather than limitations to the present invention. Any changes or alterations derived from the spirit of the present invention are still within the protection scope of the present invention.

The invention claimed is:

1. A compound of following formula or a pharmaceutically acceptable salt, stereoisomer, solvate or polymorph thereof, wherein the compound is represented by the following formula:

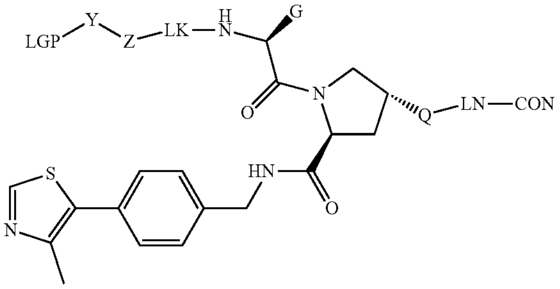

wherein Q is selected from the group consisting of:

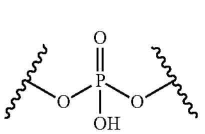, wherein LN is selected from the group consisting of:

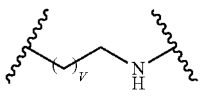, wherein V is an integer of 3-15,

G in the formula is selected from the group consisting of C1-C10 alkyl, C3-C10 cycloalkyl, and 3-10 membered heterocyclic alkyl containing 1-3 heteroatoms selected from O, N and S, LGP is a target protein binding ligand selected from the group consisting of:

LGP-1

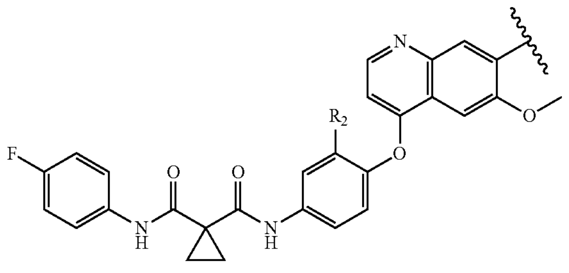

LGP-2

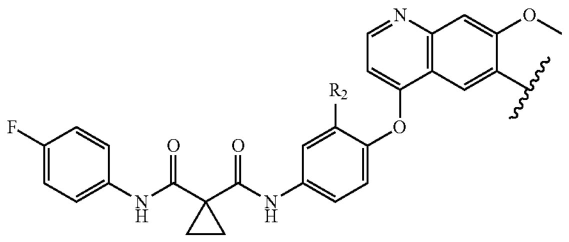

LGP-4

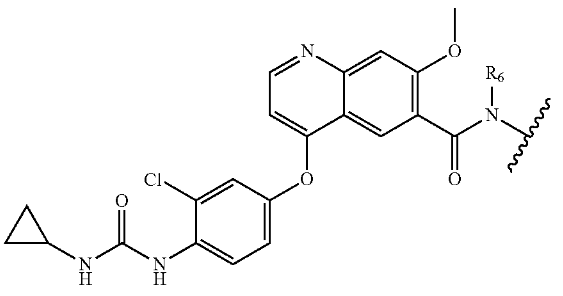

LGP-5

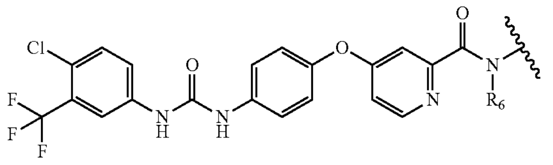

-continued

LGP-7

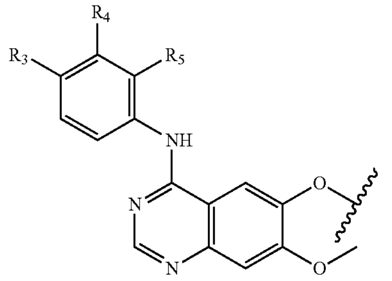

LGP-8

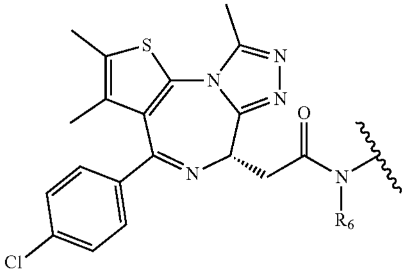

LGP-9

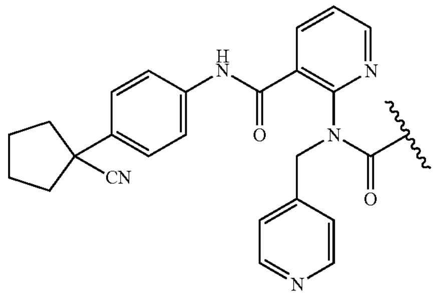

LGP-10

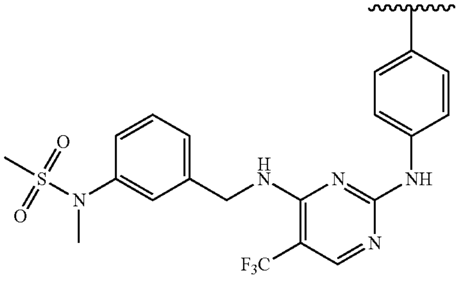

LGP-11

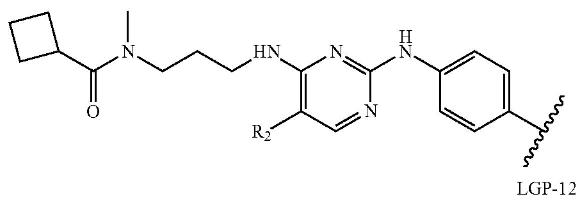

LGP-12

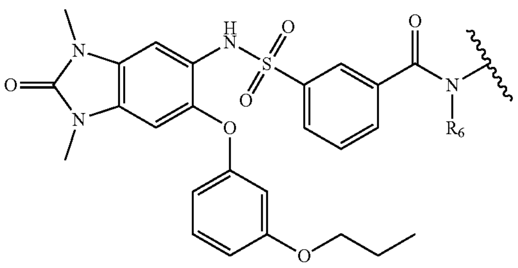

-continued

LGP-13

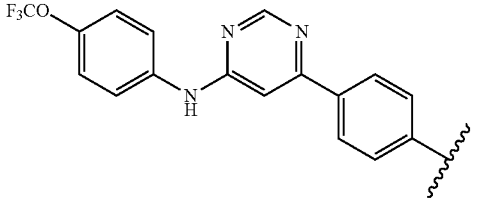

LGP-14

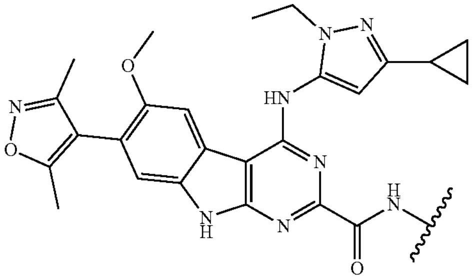

and

LGP-15

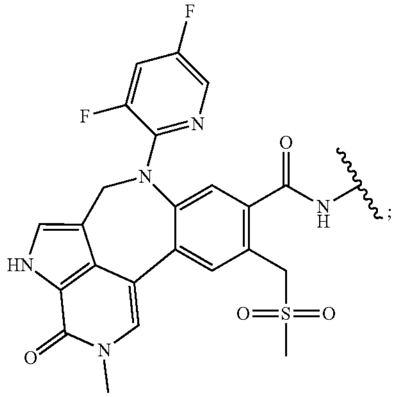

;

Y and Z are independently selected from the group consisting of a covalent bond, $CH_2$, and O; and Z is selected from the group consisting of a covalent bond and $CH_2$ when Y is selected from the group consisting of O; or Y is selected from the groups consisting of a covalent bond and $CH_2$ when Z is selected from the group consisting of O;

LK is connected with LGP through Y—Z at one end thereof and is connected with LGE through covalent bond at the other end thereof, and LK is selected from the group consisting of:

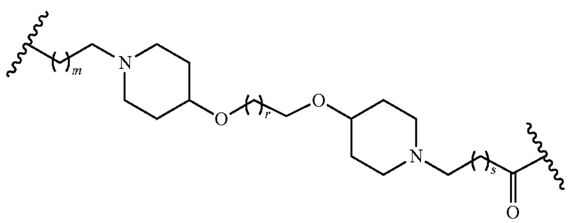

-continued

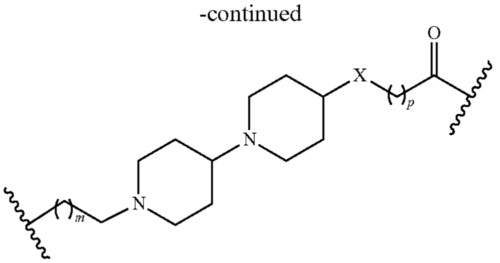

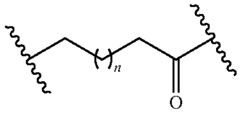

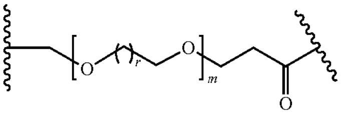

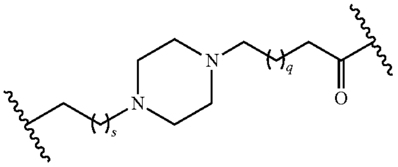

and

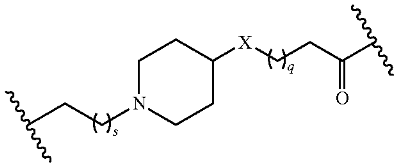

-continued

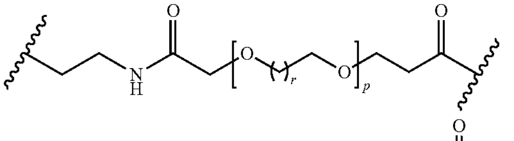

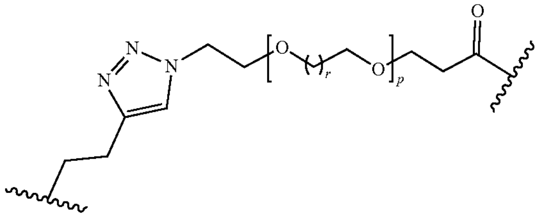

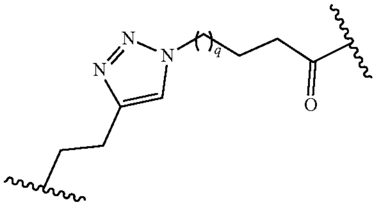

where m is an integer of 0-5; n is an integer of 0-20; p is an integer of 0-4; q is an integer of 0-20; r is an integer of 1-3; and s is an integer of 1-5; and X is selected from the groups consisting of $CH_2$, O, S and $NR^1$, wherein $R^1$ is selected from the group consisting of H, C1-6 alkyl, C1-6 haloalkyl, and C1-6 alkoxy substituted C1-6 alkyl;

wherein CON is a ligand of asialoglycoprotein receptor (ASGPR) selected from the group consisting of

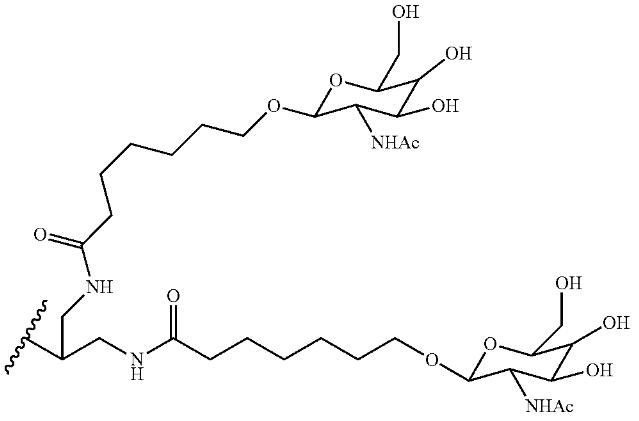

and

-continued

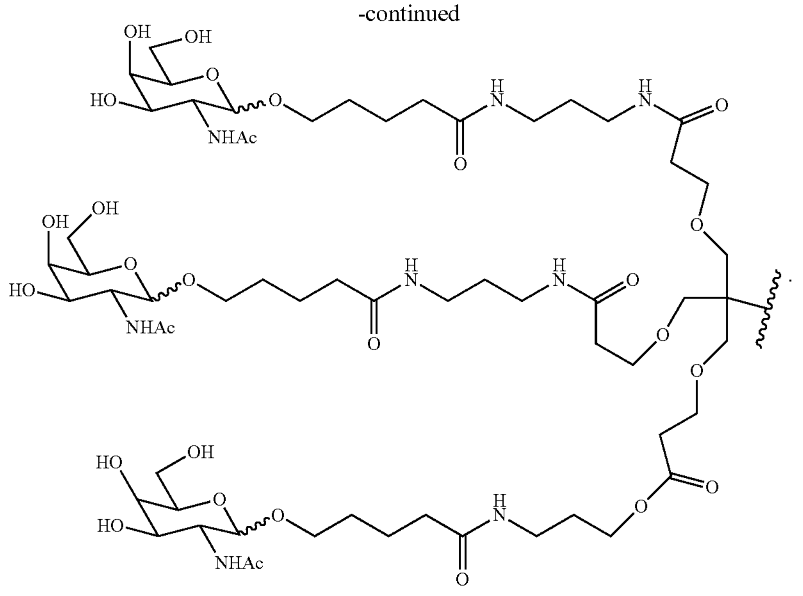

2. The compound according to claim 1, wherein a binding target of LGP is selected from the group consisting of EGFR, VEGFR, FGFR, PDGFR, Raf, Braf, RET, FLT, c-Kit, and MET.

3. The compound according to claim 1, wherein V is an integer of 5-12.

4. The compound according to claim 1, wherein G is isopropyl, tertiary butyl, cyclohexyl or tetrahydropyran.

5. The compound according to claim 4, wherein G is tertiary butyl.

6. The compound according to claim 1, wherein the compound is selected from the following structures:

WG-1
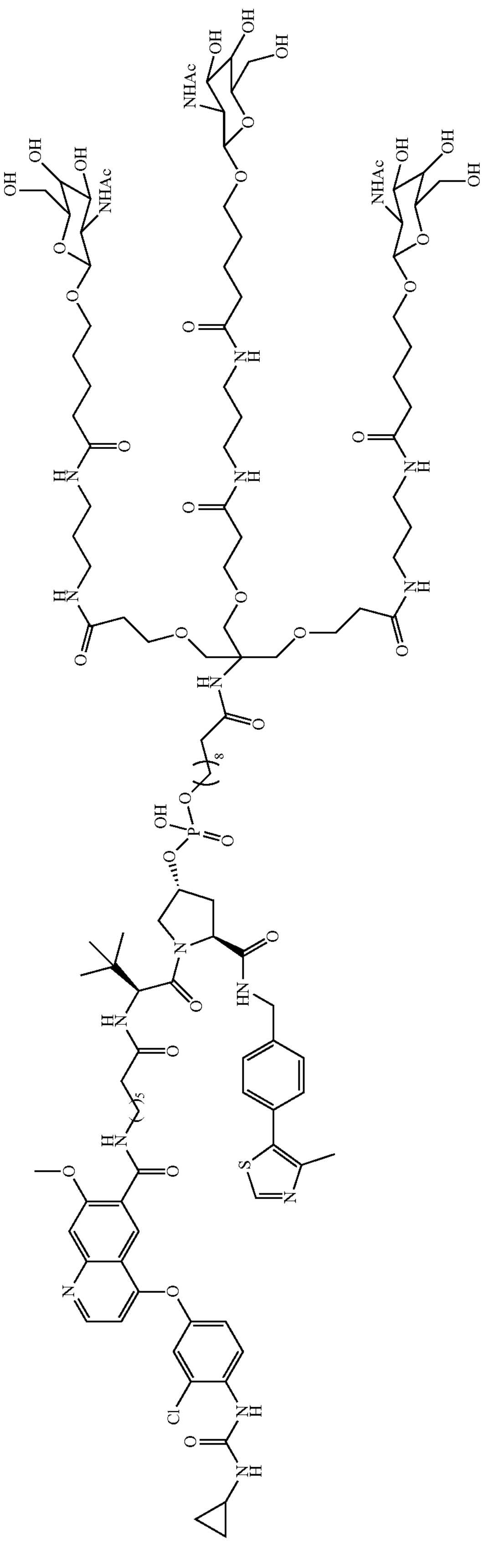
WG-2
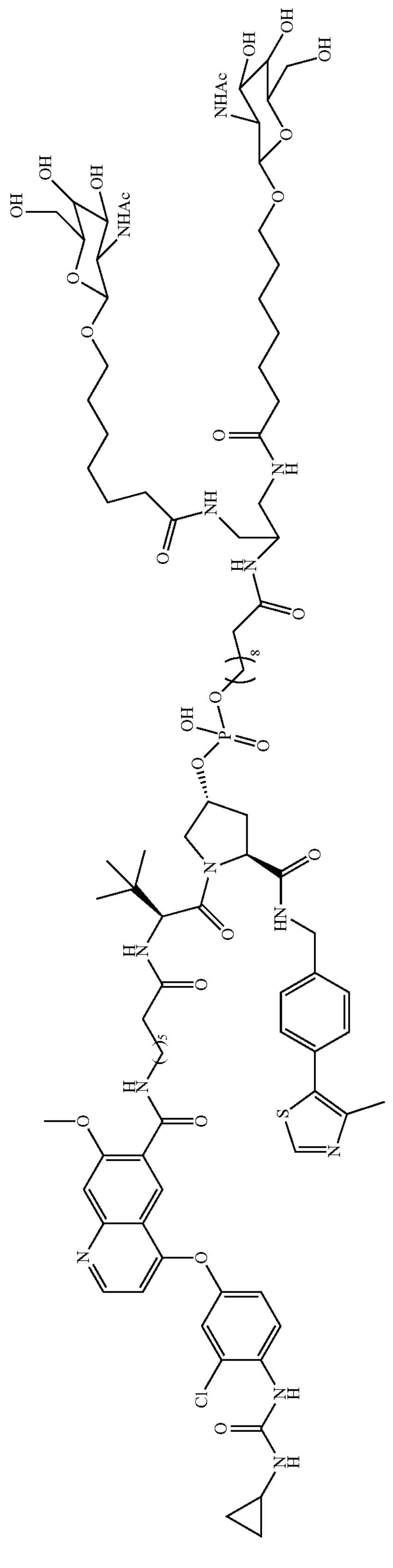

-continued
WG-3
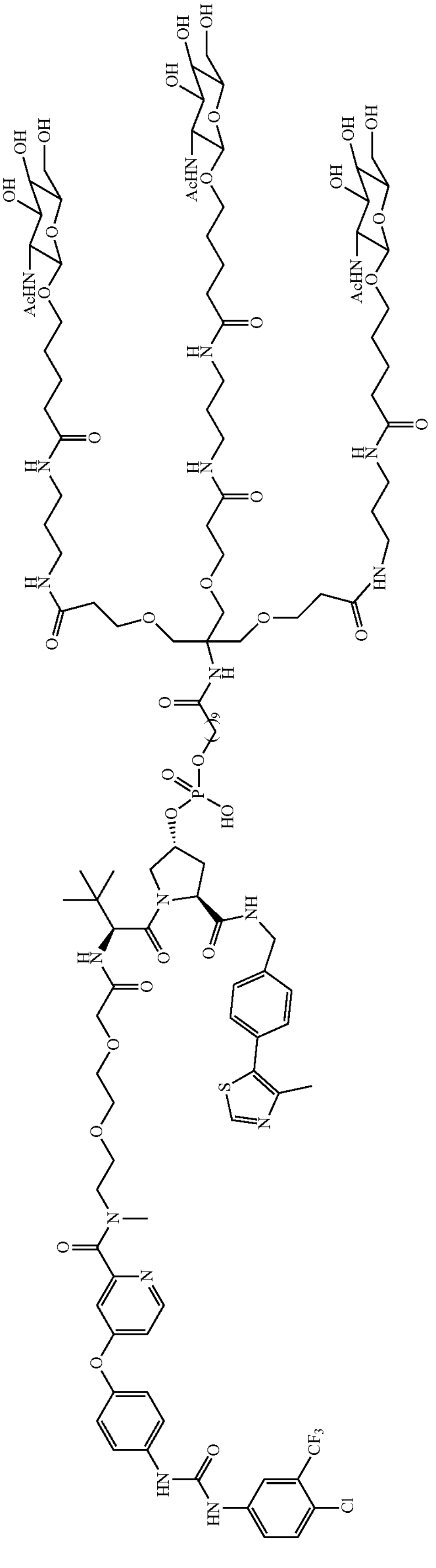

-continued
WG-4
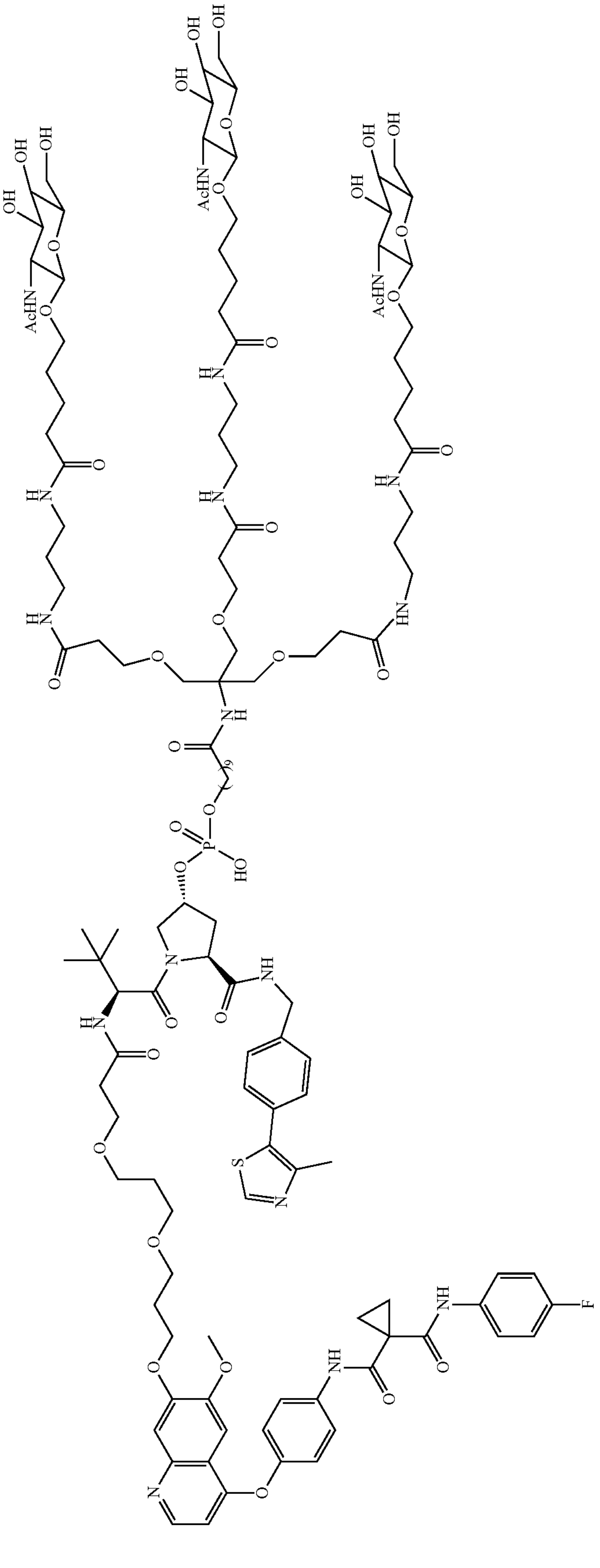

-continued
WG-5
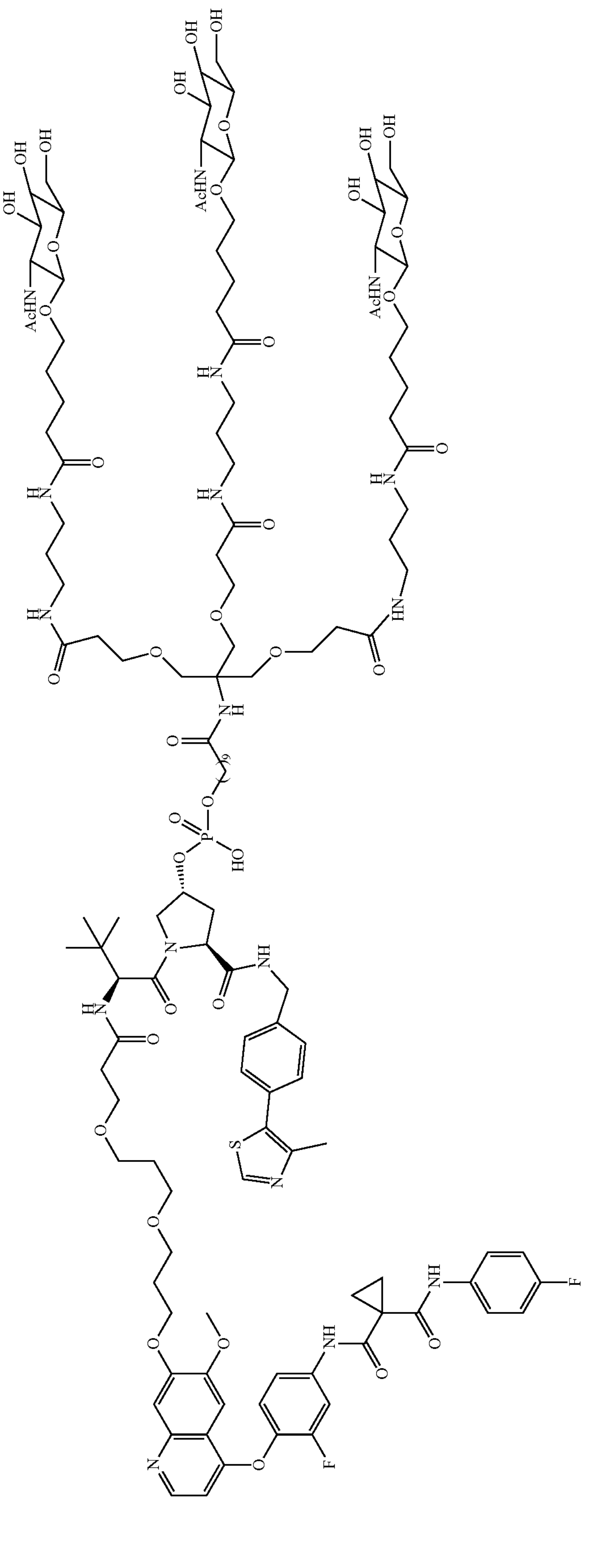

-continued
WG-6
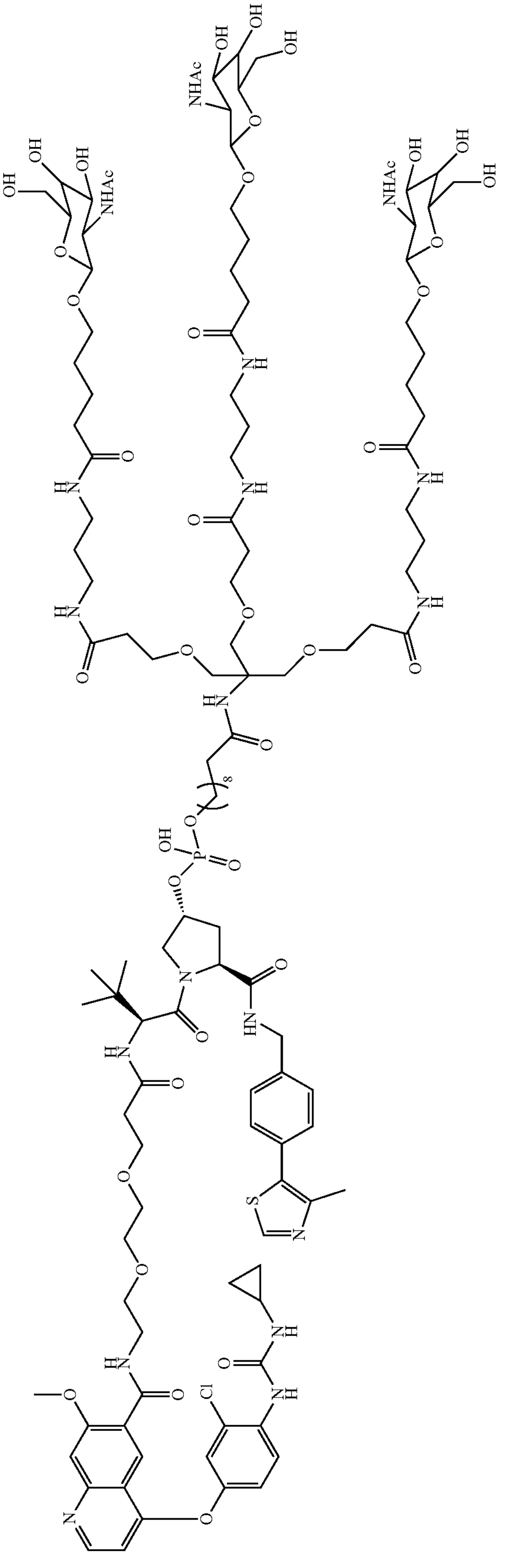
WG-7
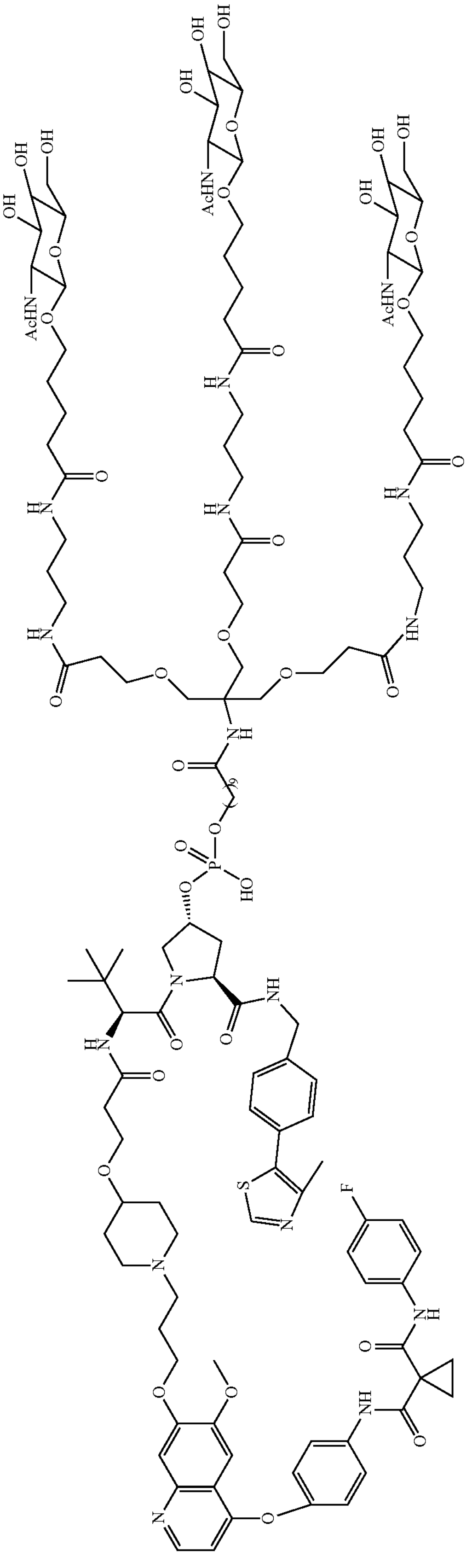

-continued
WG-8
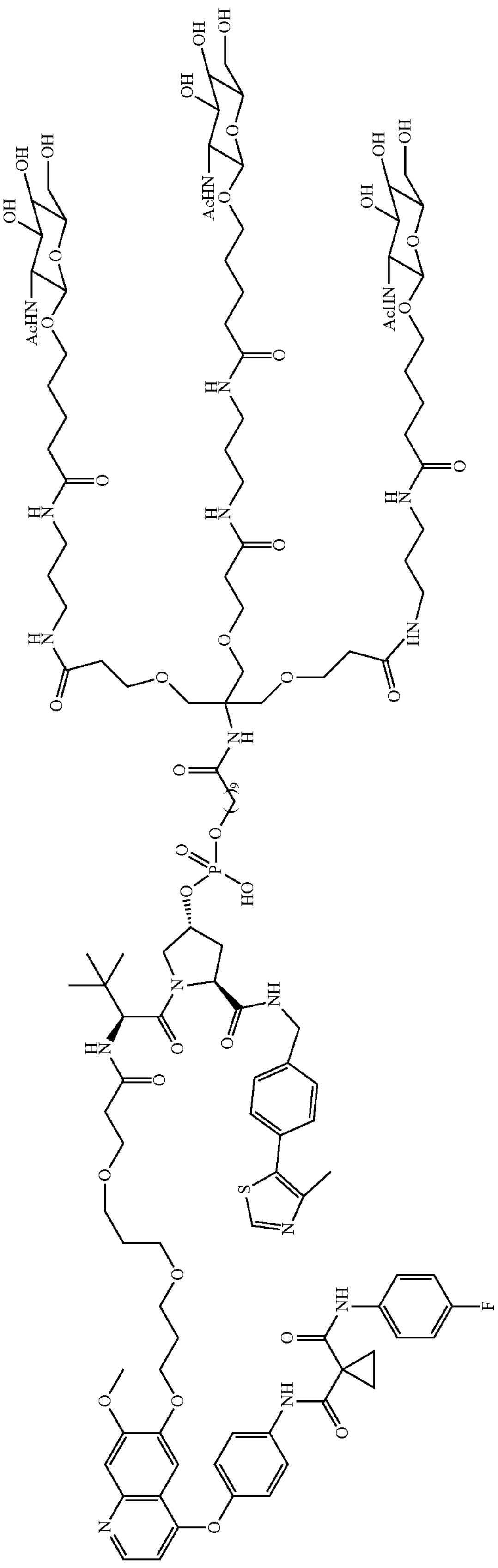

-continued
WG-9
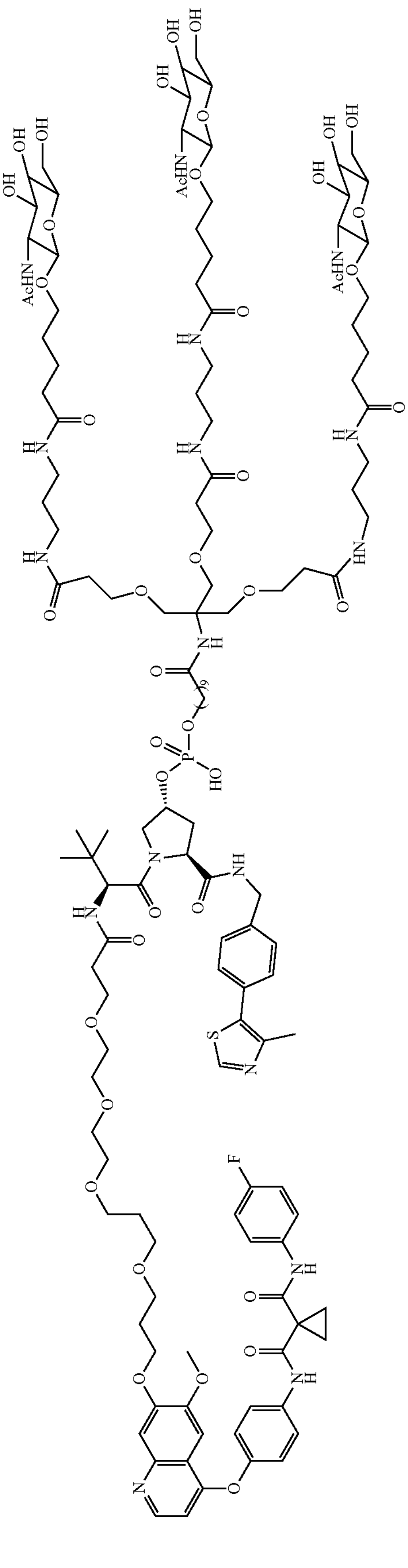
WG-10
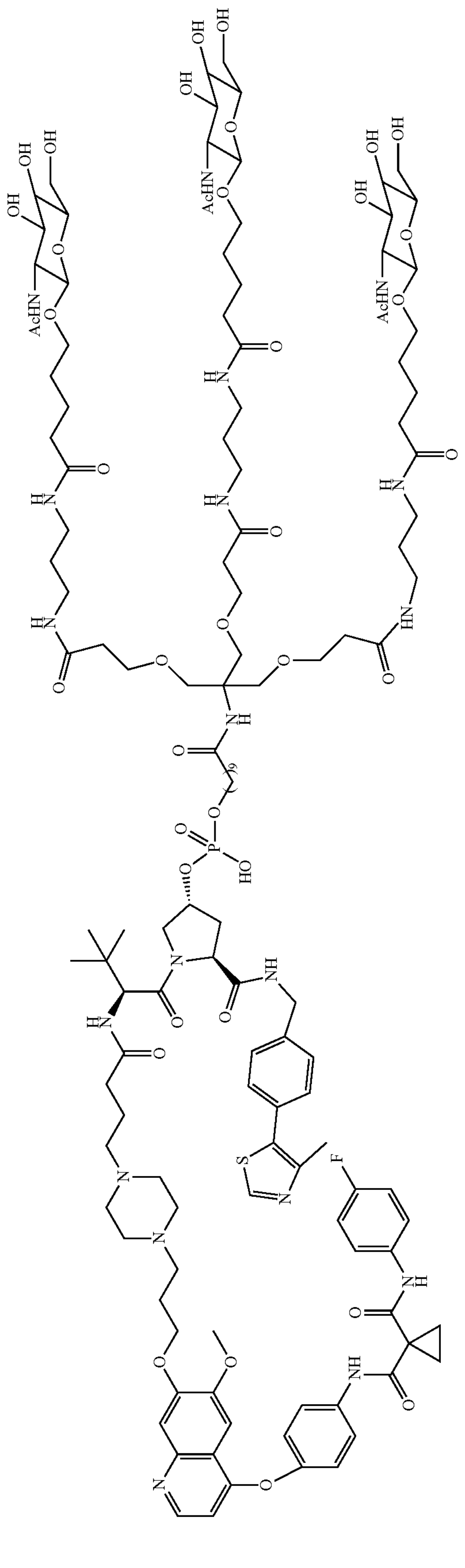

-continued
WG-11
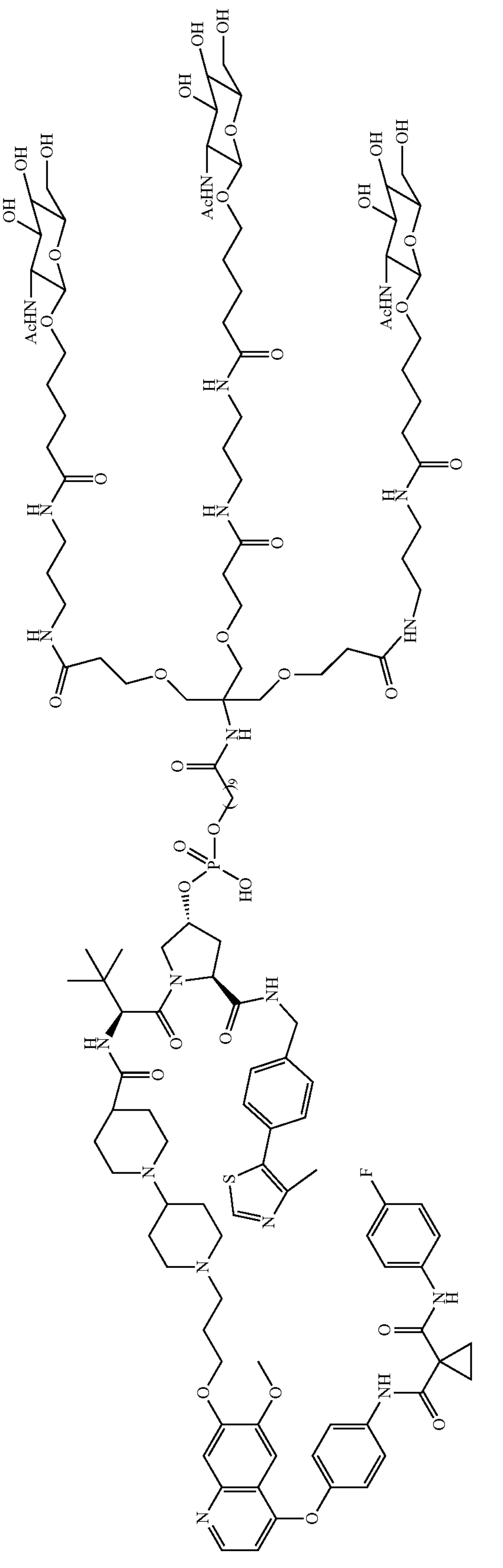

-continued
WG-12
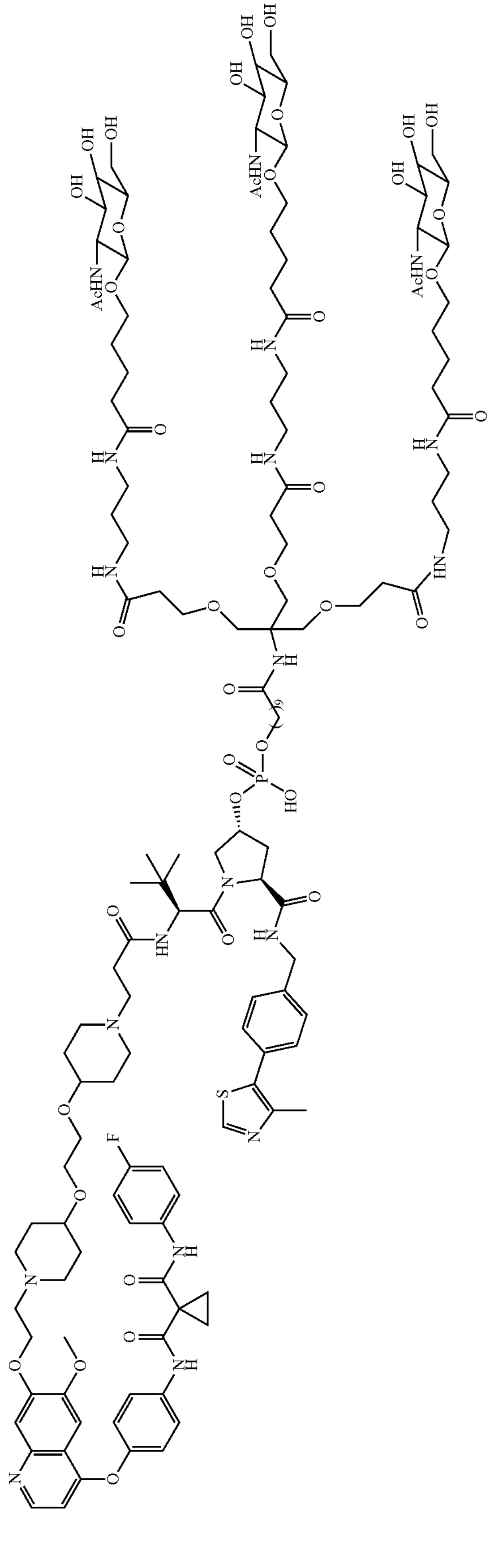
WG-13
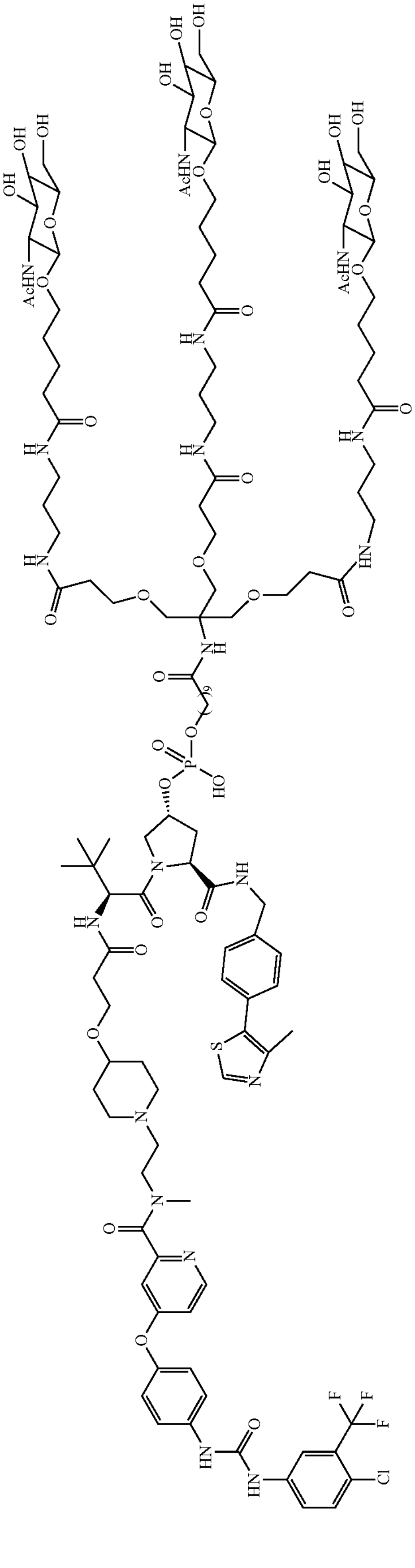

-continued
WG-14
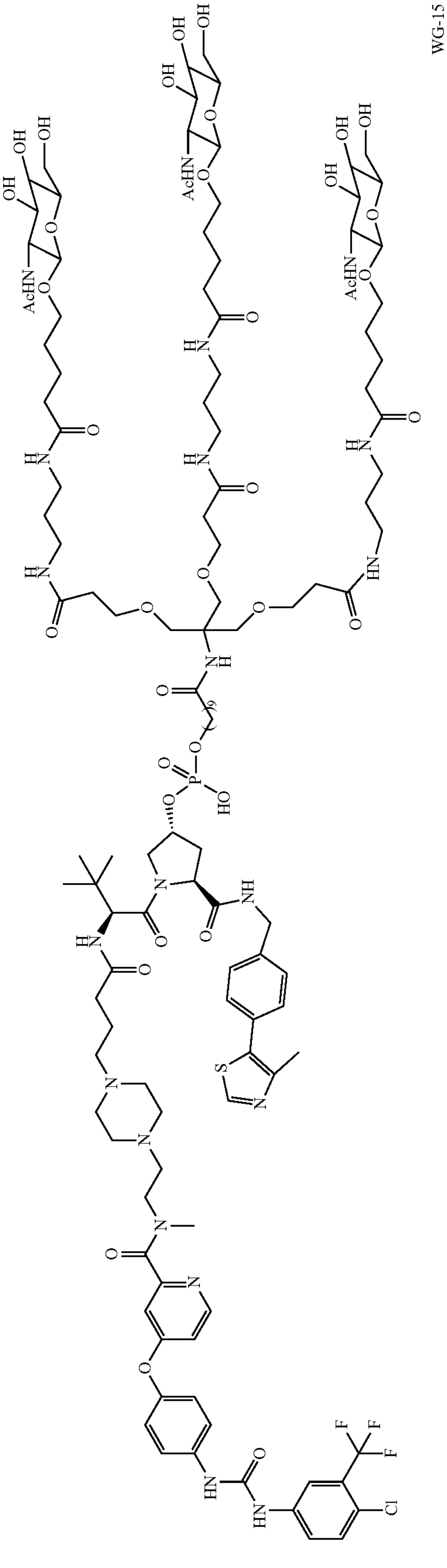
WG-15
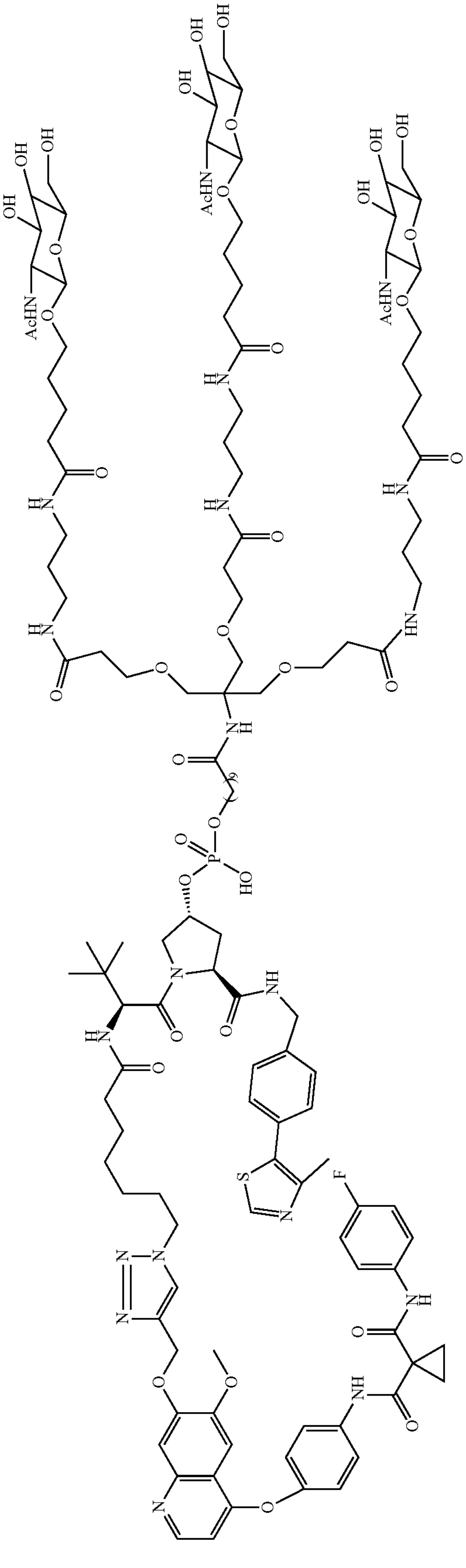

-continued
WG-16
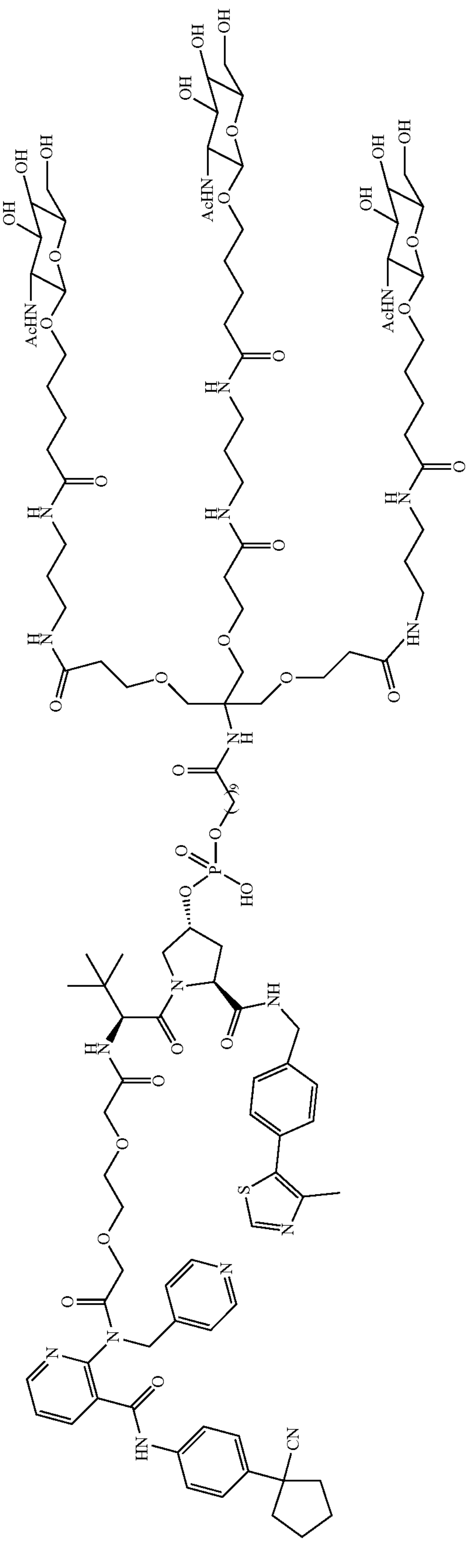
WG-17
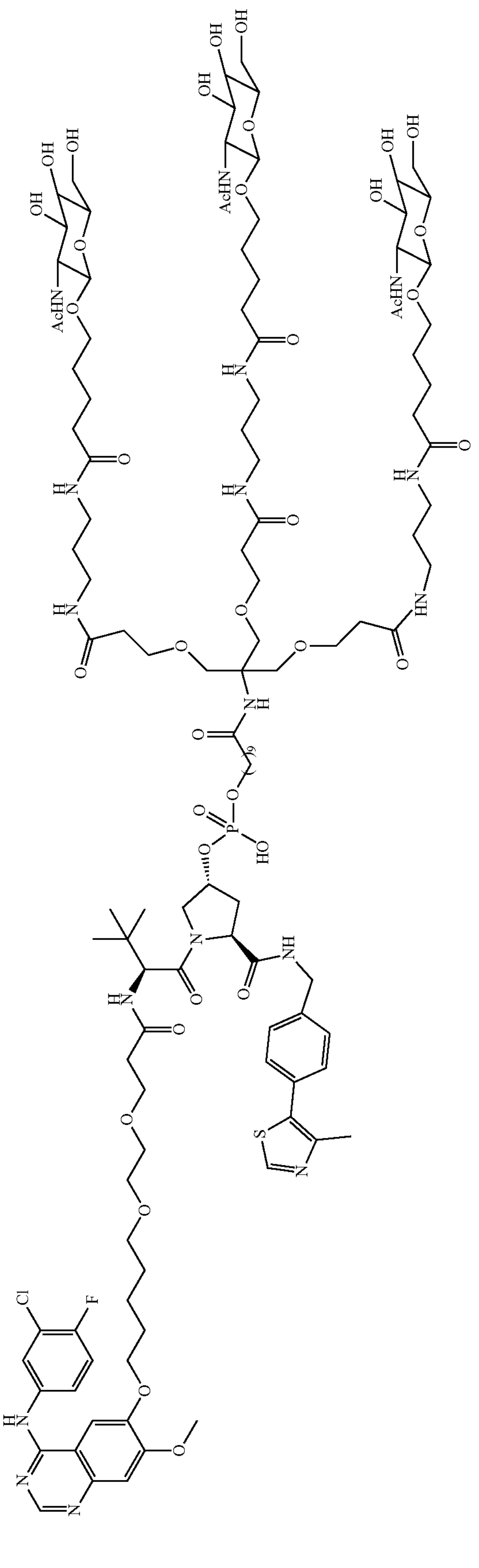

-continued
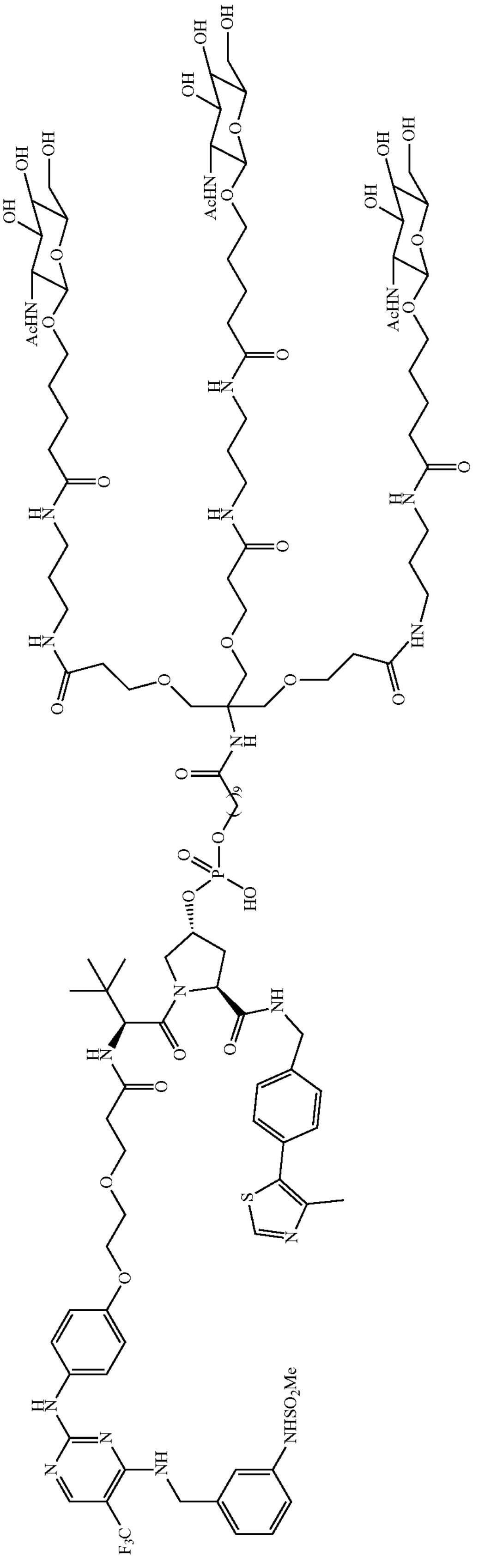
WG-18

-continued
WG-19
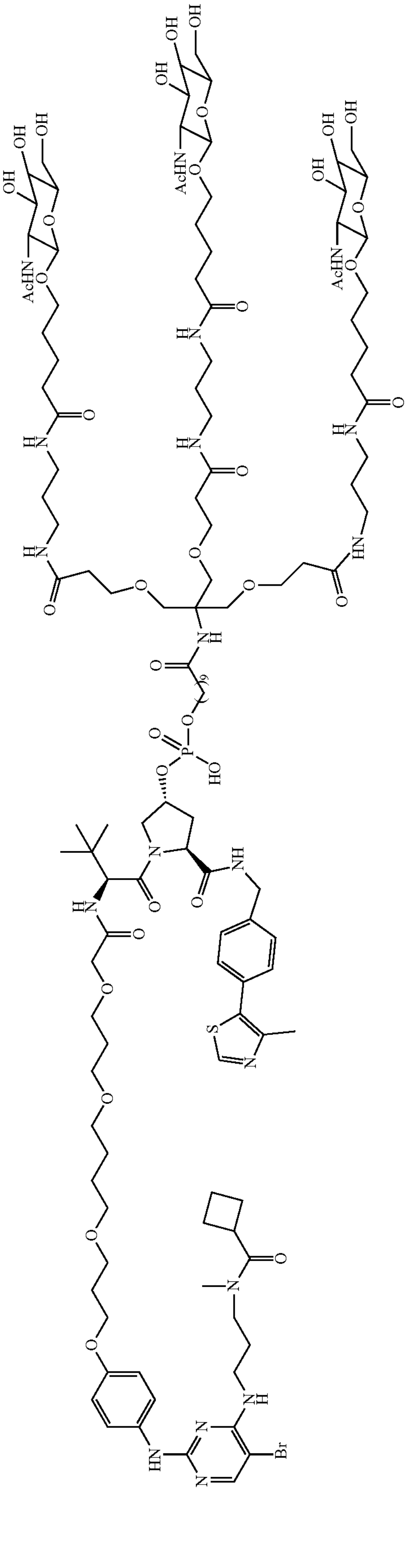
WG-20
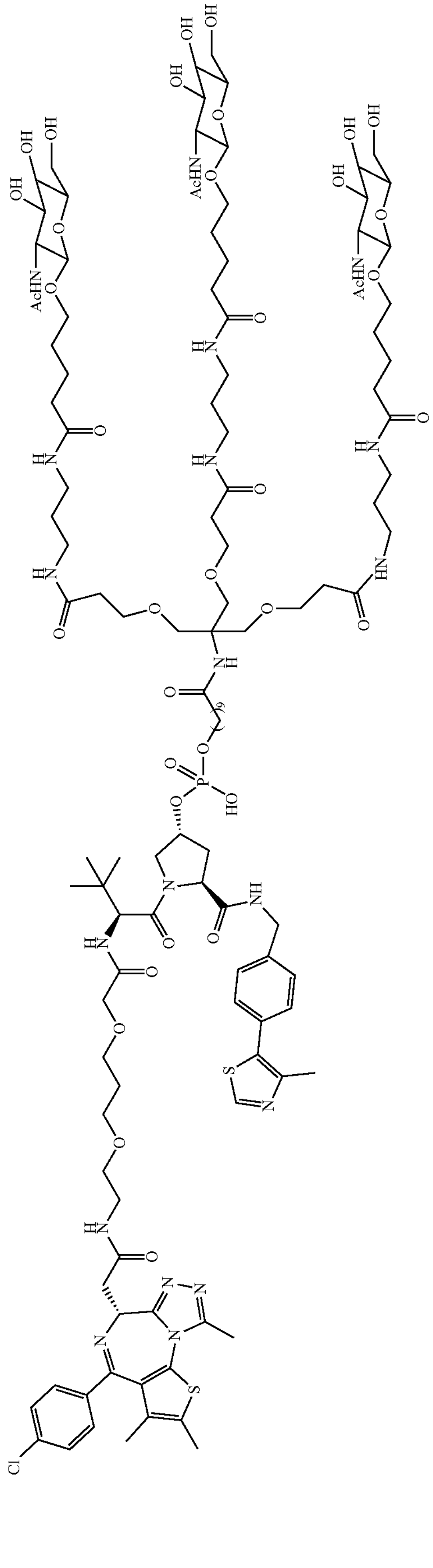

-continued
WG-21
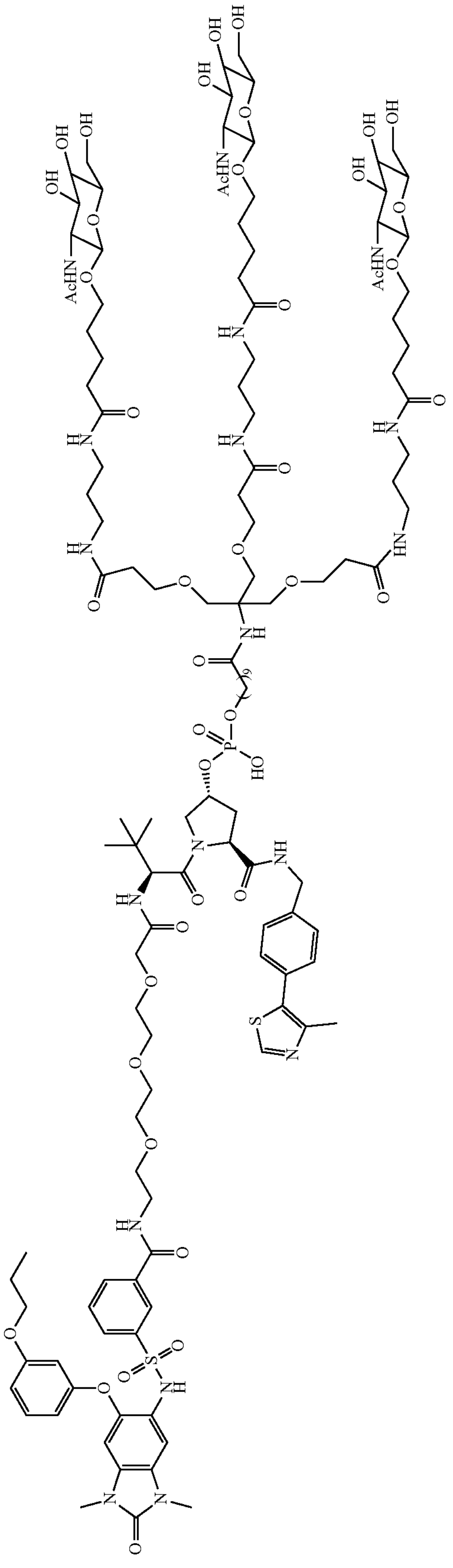
WG-22
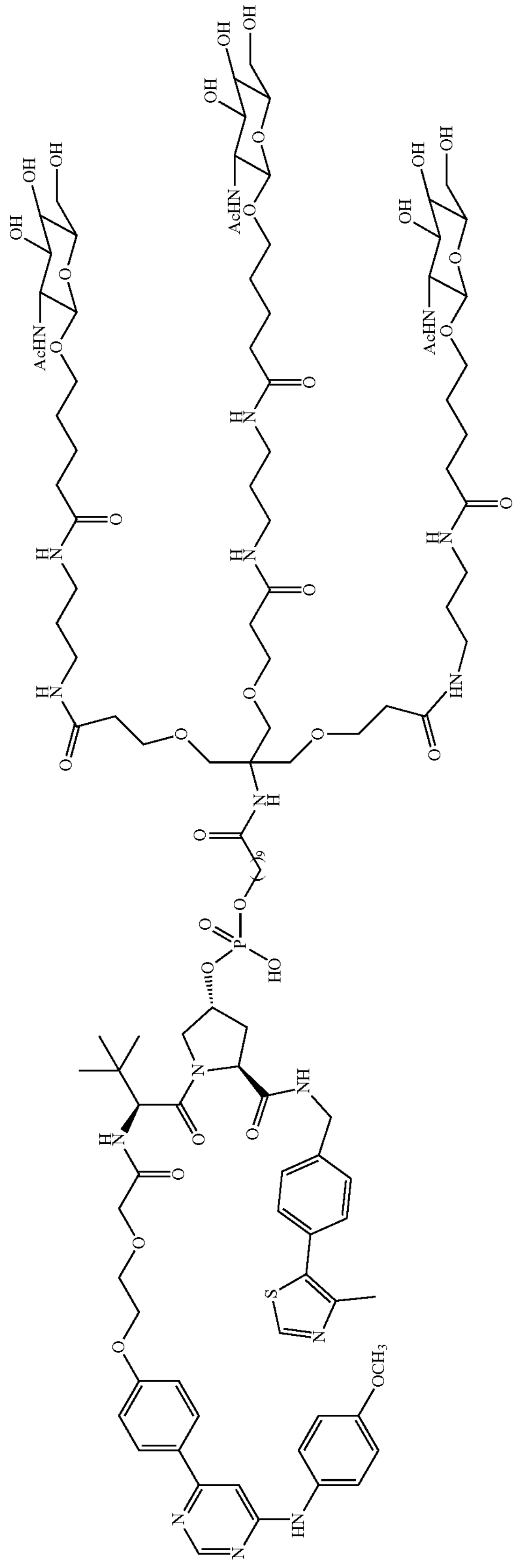

-continued
WG-23
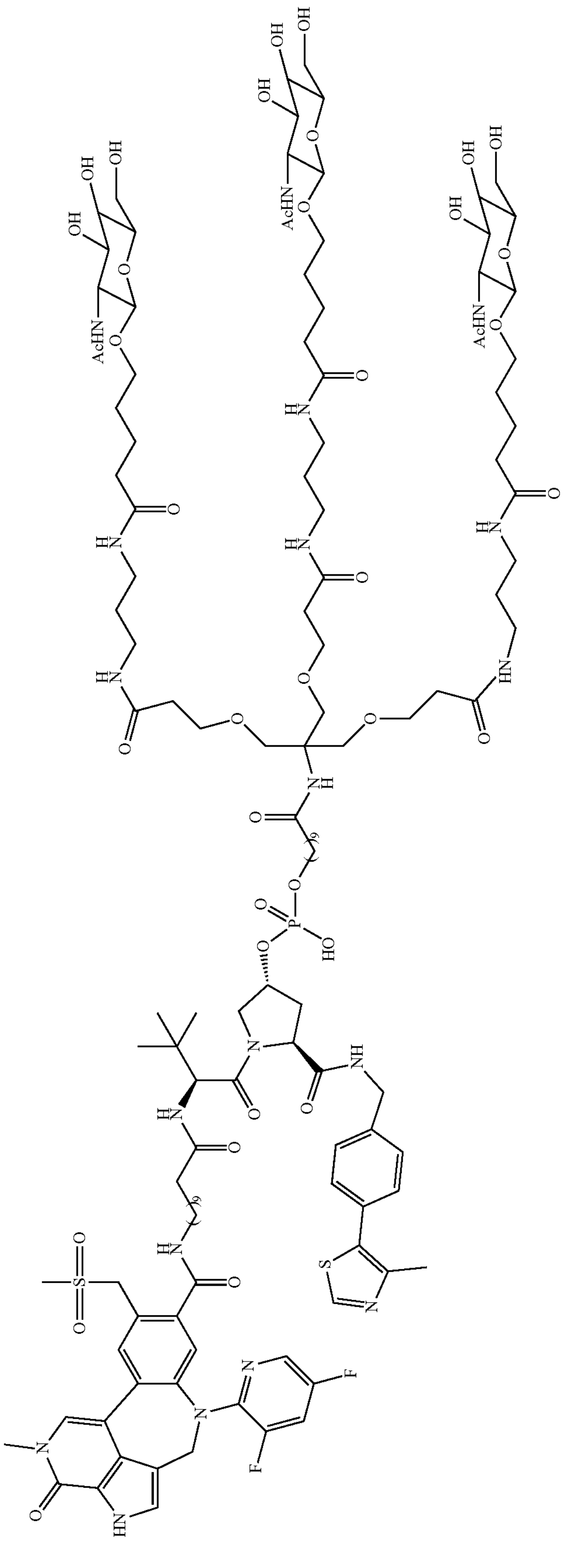

-continued
WG-24
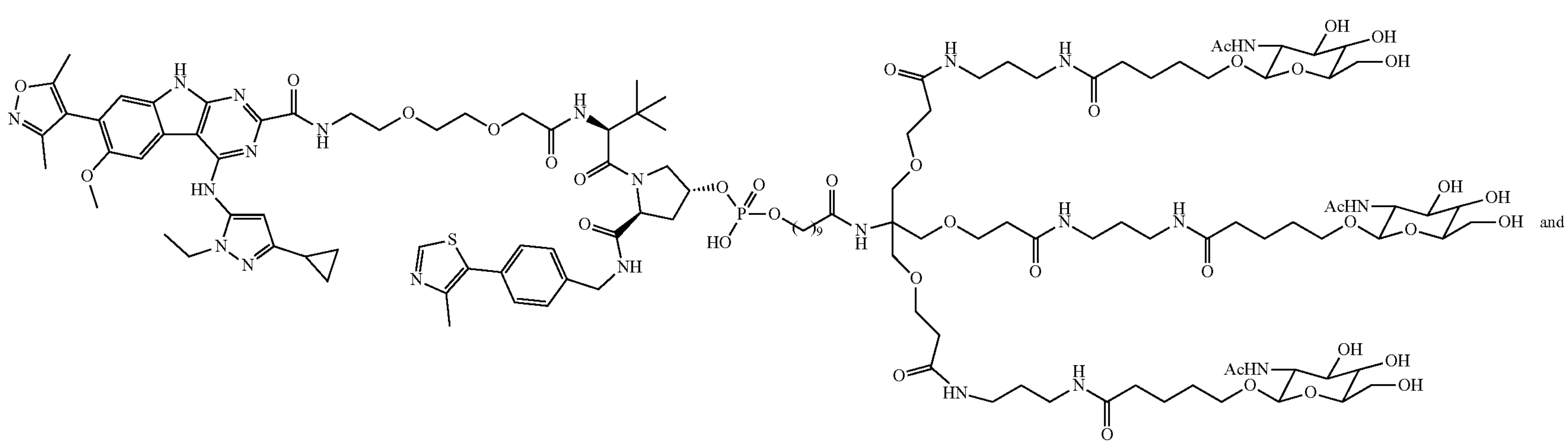
and
WG-25
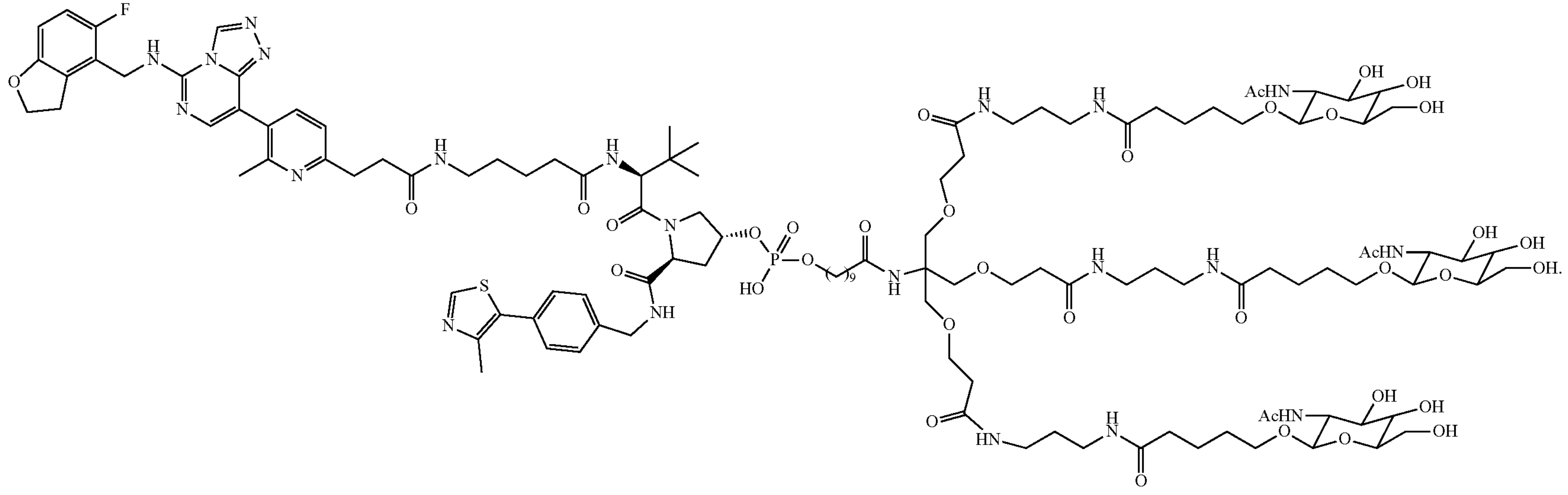

-continued
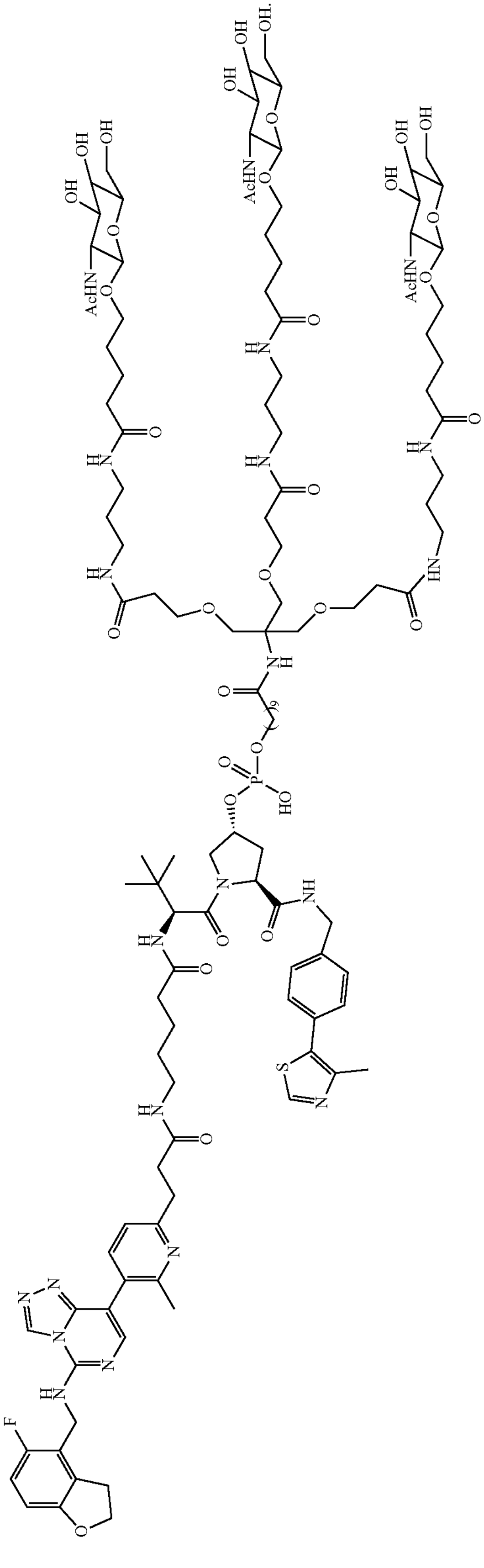
WG-25

7. The compound according to claim 6, wherein the compound is selected from WG-1, WG-2, WG-3, WG-4, WG-5, and WG-6.

8. A pharmaceutical composition, comprising the compound according to claim 1.

9. A method for treating tumors or liver diseases, comprising administering the compound according to claim 1 to a subject in need.

10. The method according to claim 9, wherein the tumor is liver cancer.

11. The method according to claim 9, wherein the liver disease is hepatitis.

* * * * *